US010398768B2

United States Patent
Baric et al.

(10) Patent No.: US 10,398,768 B2
(45) Date of Patent: Sep. 3, 2019

(54) METHODS AND COMPOSITIONS FOR RECOMBINANT DENGUE VIRUSES FOR VACCINE AND DIAGNOSTIC DEVELOPMENT

(71) Applicant: The University of North Carolina at Chapel Hill, Chapel Hill, NC (US)

(72) Inventors: Ralph Baric, Haw River, NC (US); Douglas Widman, Carrboro, NC (US); Boyd Yount, Hillsborough, NC (US); Emily Gallichotte, Carrboro, NC (US); Scott Royal, Carrboro, NC (US); Aravinda Desilva, Chapel Hill, NC (US); Jesica Swanstrom, Morrisville, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/523,899

(22) PCT Filed: Nov. 2, 2015

(86) PCT No.: PCT/US2015/058610
§ 371 (c)(1),
(2) Date: May 2, 2017

(87) PCT Pub. No.: WO2016/070178
PCT Pub. Date: May 6, 2016

(65) Prior Publication Data
US 2017/0333548 A1 Nov. 23, 2017

Related U.S. Application Data

(60) Provisional application No. 62/074,053, filed on Nov. 2, 2014.

(51) Int. Cl.
| | |
|---|---|
| *A61K 39/12* | (2006.01) |
| *C07K 14/005* | (2006.01) |
| *C12N 7/00* | (2006.01) |
| *C07K 16/10* | (2006.01) |
| *G01N 33/569* | (2006.01) |
| *A61K 39/00* | (2006.01) |

(52) U.S. Cl.
CPC .......... *A61K 39/12* (2013.01); *C07K 14/005* (2013.01); *C07K 16/1063* (2013.01); *C12N 7/00* (2013.01); *G01N 33/56983* (2013.01); *A61K 2039/5258* (2013.01); *A61K 2039/575* (2013.01); *C07K 2317/21* (2013.01); *C07K 2319/40* (2013.01); *C12N 2770/24122* (2013.01); *C12N 2770/24123* (2013.01); *C12N 2770/24134* (2013.01); *C12N 2770/24171* (2013.01); *G01N 2333/18* (2013.01); *G01N 2333/185* (2013.01); *G01N 2469/20* (2013.01); *Y02A 50/386* (2018.01); *Y02A 50/53* (2018.01)

(58) Field of Classification Search
None
See application file for complete search history.

(56) References Cited

U.S. PATENT DOCUMENTS

| | | | |
|---|---|---|---|
| 4,501,729 | A | 2/1985 | Boucher et al. |
| 4,708,871 | A | 11/1987 | Geysen |
| 7,862,829 | B2 | 1/2011 | Johnston et al. |

FOREIGN PATENT DOCUMENTS

| | | |
|---|---|---|
| WO | WO 94/00153 A1 | 1/1994 |
| WO | WO 95/17210 A1 | 6/1995 |
| WO | WO 96/33739 A1 | 10/1996 |
| WO | WO 2013/151764 A1 | 10/2013 |
| WO | WO 2014/210358 A1 | 12/2014 |

OTHER PUBLICATIONS

Bielefeldt-Ohmann et al. "Analysis of a recombinant dengue-2 virus-dengue-3 virus hybrid envelope protein expressed in a secretory baculovirus system" *Journal of General Virology* 78:2723-2733 (1997).

Chen et al. "Construction of Intertypic Chimeric Dengue Viruses Exhibiting Type 3 Antigenicity and Neurovirulence for Mice" *Journal of Virology* 69(8):5186-5190 (1995).

Extended European Search Report corresponding to European Patent Application No. 15854399.1 (13 pages) (dated Mar. 26, 2018).

Hiramatsu et al. "Mutational Analysis of a Neutralization Epitope on the Dengue Type 2 Virus (DEN2) Envelope Protein: Monoclonal Antibody Resistant DEN2/DEN4 Chimeras Exhibit Reduced Mouse Neurovirulence" *Virology* 224:437-445 (1996).

Khanam et al. "Induction of Neutralizing Antibodies Specific to Dengue Virus Serotypes 2 and 4 by a Bivalent Antigen Composed of Linked Envelope Domains III of These Two Serotypes" *American Journal of Tropical Medicine & Hygiene* 74(2):266-277 (2006).

Messer et al. "Dengue virus envelope protein domain I/II hinge determines long-lived serotype-specific dengue immunity" *Proceedings of the National Academy of Sciences* 111(5):1939-1944 (2014).

(Continued)

*Primary Examiner* — Stacy B Chen
(74) *Attorney, Agent, or Firm* — Myers Bigel, P.A.

(57) ABSTRACT

The present invention provides compositions and methods of use comprising a chimeric dengue virus E glycoprotein comprising a dengue virus E glycoprotein backbone, which comprises amino acid substitutions that introduce an epitope that is recognized by an antibody from a dengue virus serotype that is different from the dengue virus serotype of the dengue virus E glycoprotein backbone.

14 Claims, 36 Drawing Sheets

Specification includes a Sequence Listing.

(56) References Cited

OTHER PUBLICATIONS

Huang et al. "Chimeric Dengue Type 2 (Vaccine Strain PDK-53)/Dengue Type 1 Virus as a Potential Candidate Dengue Type 1 Virus Vaccine" *Journal of Virology* 74(7):3020-3028 (2000).
International Search Report and the Written Opinion of the International Searching Authority corresponding to International Patent Application No. PCT/US2015/058610 (12 pages) (dated Mar. 31, 2016).
Messer et al. "Development and Characterization of a Reverse Genetic System for Studying Dengue Virus Serotype 3 Strain Variation and Neutralization" *PLoS Neglected Tropical Diseases* 6(2):e1486 (2012).
De Alwis et al. "Identification of human neutralizing antibodies that bind to complex epitopes on dengue virions" *Proceedings of the National Academy of Sciences* 109(19):7439-7444 (2012).
Fibriansah et al. "Potent anti-dengue human antibody preferentially recognizes the confirmation of E protein monomers assembled on the virus surface" *EMBO Molecular Medicine* 6(3):358-371 (2014).
Gallichotte et al. "Use of chimeric recombinant dengue viruses to map the serotype 2 neutralizing human antibody response" *Poster presented at the Pan-American Dengue Research Network Meeting* (1 page) (Oct. 20, 2014).
Gallichotte et al. "A New Quaternary Structure Epitope on Dengue Virus Serotype 2 Is the Target of Durable Type-Specific Neutralizing Antibodies" *mBio* 6(5):e01461-15 (2015).
GenBank Accession No. DQ211652 "West Nile virus strain NY99, complete genome" *NCBI* (5 pages) (Jun. 7, 2006).
GenBank Accession No. JX503529 "Yellow fever virus strain" *NCBI* (5 pages) (Sep. 16, 2012).
GenBank Accession No. U14163 "Japanese encephalitis virus SA14 polyprotein mRNA, complete cds" *NCBI* (5 pages) (Sep. 13, 1994).
Geysen et al. "Use of peptide synthesis to probe viral antigens for epitopes to a resolution of a single amino acid" *Proceedings of the National Academy of Sciences* 81:3998-4002 (1984).
Geysen et al. "A Priori Delineation of a Peptide Which Mimics a Discontinuous Antigenic Determinant" *Molecular Immunology* 23(7)709-715 (1986).
Hopp et al. "Prediction of protein antigenic determinants from amino acid sequences" *Proceedings of the National Academy of Sciences* 78(6):3824-3828 (1981).
International Preliminary Report on Patentability corresponding to International Patent Application No. PCT/US2015/058610 (8 pages) (dated May 11, 2017).
Kaufmann et al. "Neutralization of West Nile virus by cross-linking of its surface proteins with Fab fragments of the human monoclonal antibody CR4354" *Proceedings of the National Academy of Sciences* 107(44):18950-18955 (2010).
Kyte et al. "A Simple Method for Displaying the Hydropathic Character of a Protein" *Journal of Molecular Biology* 157(1):105-132 (1982).
Meloen et al. "Mimotopes: realization of an unlikely concept" *Journal of Molecular Recognition* 13:352-359 (2000).
Mukherjee et al. "Mechanism and Significance of Cell Type-Dependent Neutralization of Flaviviruses" *Journal of Virology* 88(13):7210-7220 (2014).
Pal et al. "Immunization with the chlamydia trachomatis major outer membrane protein, using adjuvants developed for human vaccines, can induce partial protection in a mouse model against a genital challenge" *Vaccine* 24(6):766-775 (2005) (Abstract Only).
Tyle, Praveen "Iontophoretic Devices for Drug Delivery" *Pharmaceutical Research* 3(6):318-326 (1986).
Wahala et al. "Dengue virus neutralization by human immune sera: Role of envelope protein domain III-reactive antibody" *Virology* 392:103-113 (2009).
Whitehead et al. "Prospects for a dengue virus vaccine" *Nature Reviews Microbiology* 5(7):518-528 (2007) (Abstract Only).

FIG. 1

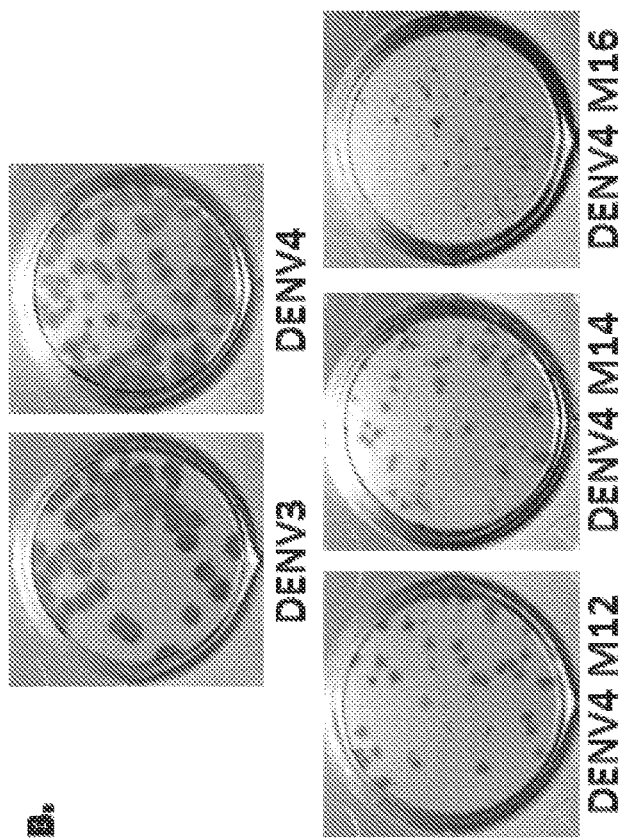
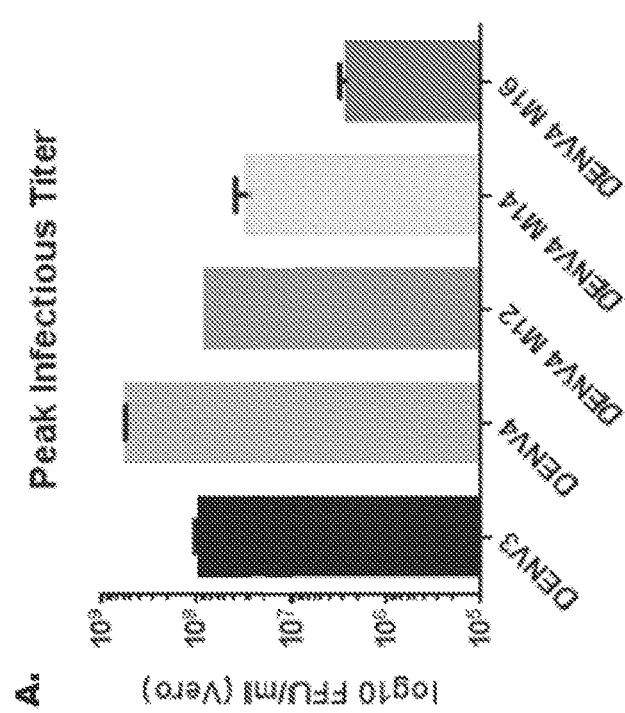
FIG. 2

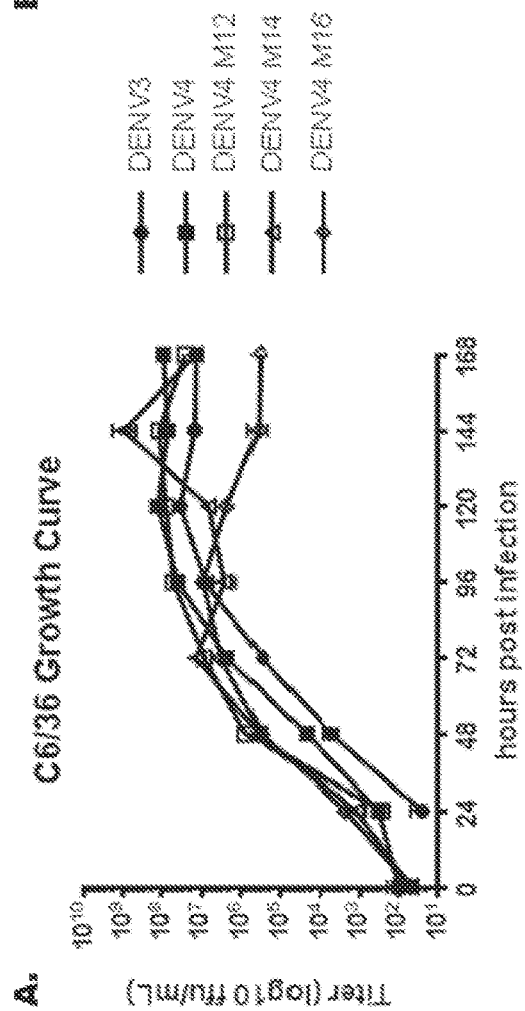
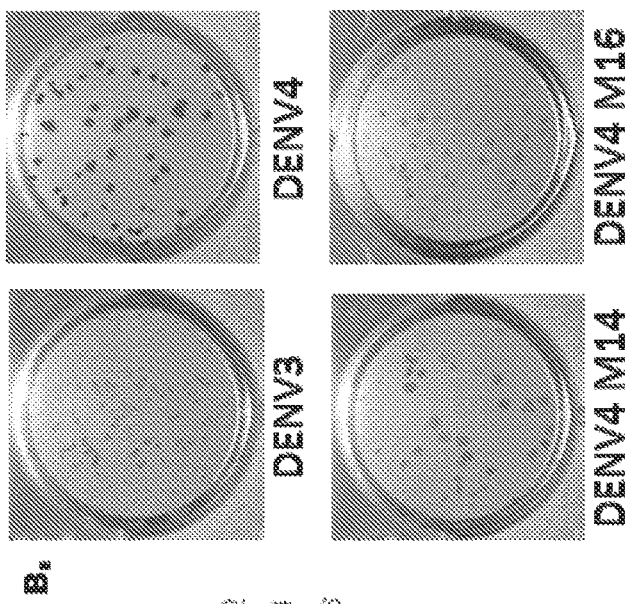
FIG. 3

| | |
|---|---|
| DENV2 | GMSYSMCTGKFKIVKEIAETQHGTIVIRVQYEGDGSPCKIPFEITDLEKR |
| DENV4 | GMSYTMCSGKFSIDKEMAETQHGTTVVKVKYEGAGAPCKVPIEIRDVNKE |
| DENV4/2 | GMSYSMCTGKFKIVKEIAETQHGTIVIRVQYEGDGSPCKIPFEITDLEKR |
| | |
| DENV2 | HVLGRLITVNPIVTEKDSPVNIEAEPPFGDSYIIIGVEPGQLKLNWFKK |
| DENV4 | KVVGRVISSTPLAENTNSVTNIELEPPFGDSYIVIGVGNSALTLHWFRK |
| DENV4/2 | HVLGRLITVNPIVTEKDSPVNIEAEPPFGDSYIIIGVEPGQLKLNWFKK |

B

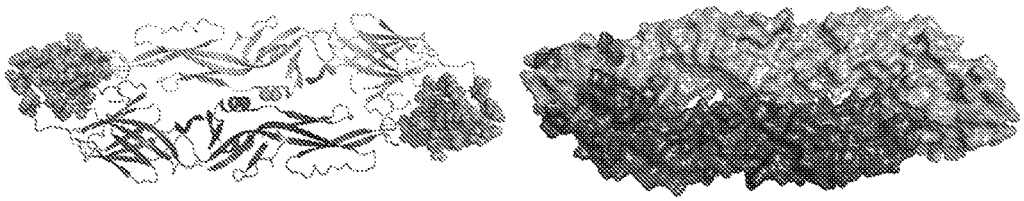

C

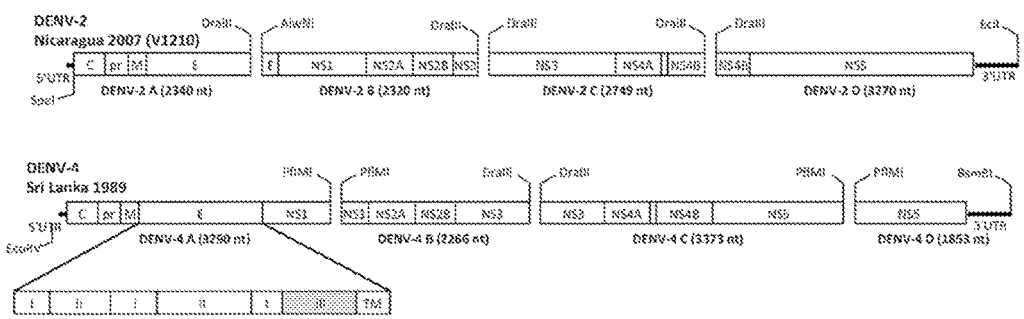

```
                          20                              40
                           |                               |
Parent WT DENV2   MRCIGISNRD FVEGVSGGSW VDIVLEHGSC VTTMAKNKPT LDFELIKTEA 50
DV4-EDIII-DV2     MRCVGVGNRD FVEGVSGGAW VDLVLEHGGC VTTMAQGKPT LDFELTKTTA 50
Parent WT DENV4   MRCVGVGNRD FVEGVSGGAW VDLVLEHGGC VTTMAQGKPT LDFELTKTTA 50
Consensus         MRCVGVGNRD FVEGVSGGAW VDLVLEHGGC VTTMAQGKPT LDFELTKTTA
Conservation 60                  80                     100
                           |                   |                       |
Parent WT DENV2   KQPATLRKYC IEAKLTNTTT ESRCPTQGEP SLNEEQDKRF ICKHSMVDRG 100
DV4-EDIII-DV2     KEVALLRTYC IEASISNITT ATRCPTQGEP YLKEEQDQQY ICRRDVVDRG 100
Parent WT DENV4   KEVALLRTYC IEASISNITT ATRCPTQGEP YLKEEQDQQY ICRRDVVDRG 100
Consensus         KEVALLRTYC IEASISNITT ATRCPTQGEP YLKEEQDQQY ICRRDVVDRG
Conservation 120                             140
                           |                               |
Parent WT DENV2   WGNGCGLFGK GGIVTCAMFT CKKNMEGKVV QPENLEYTIV ITPHSGEEHA 150
DV4-EDIII-DV2     WGNGCGLFGK GGVVTCAKFS CSGKITGNLV QIENLEYTVV VTVHNGDTHA 150
Parent WT DENV4   WGNGCGLFGK GGVVTCAKFS CSGKITGNLV QIENLEYTVV VTVHNGDTHA 150
Consensus         WGNGCGLFGK GGVVTCAKFS CSGKITGNLV QIENLEYTVV VTVHNGDTHA
Conservation 160                 180                     200
                           |                   |                       |
Parent WT DENV2   VGNDTGKHGK EIKITPQSSI TEAELTGYGT VTMECSPRTG LDFNEMVLLQ 200
DV4-EDIII-DV2     VGNDTSNHGV TATITPRSPS VEVKLPDYGE LTLDCEPRSG IDFNEMILMK 200
Parent WT DENV4   VGNDTSNHGV TATITPRSPS VEVKLPDYGE LTLDCEPRSG IDFNEMILMK 200
Consensus         VGNDTSNHGV TATITPRSPS VEVKLPDYGE LTLDCEPRSG IDFNEMILMK
Conservation 220                             240
                           |                               |
Parent WT DENV2   MEDKAWLVHR QWFLDLPLPW LPGADTQESN WIQKETLVTF KNPHAKKQDV 250
DV4-EDIII-DV2     MKKKTWLVHK QWFLDLPLPW TAGADTSEVH WNYKERMVTF KVPHAKRQDV 250
Parent WT DENV4   MKKKTWLVHK QWFLDLPLPW TAGADTSEVH WNYKERMVTF KVPHAKRQDV 250
Consensus         MKKKTWLVHK QWFLDLPLPW TAGADTSEVH WNYKERMVTF KVPHAKRQDV
Conservation 260                 280                     300
                           |                   |                       |
Parent WT DENV2   VVLGSQEGAM HTALTGATEI QMSSGNLLFT GHLKCRLRMD KLQLKGMSYS 300
DV4-EDIII-DV2     TVLGSQEGAM HSALAGATEV DSGDGNHMFA GHLKCKVRME KLRLKGMSYS 300
Parent WT DENV4   TVLGSQEGAM HSALAGATEV DSGDGNHMFA GHLKCKVRME KLRIKGMSYT 300
Consensus         TVLGSQEGAM HSALAGATEV DSGDGNHMFA GHLKCKVRME KLRLKGMSYS
Conservation 320                             340
                           |                               |
Parent WT DENV2   MCTGKFKIVK EIAETQHGTI VIRVQYEGDG SPCKIPFEIT DLEKRHVLGR 350
DV4-EDIII-DV2     MCTGKFKIVK EIAETQHGTI VIRVQYEGDG SPCKIPFEIT DLEKRHVLGR 350
Parent WT DENV4   MCSGKFSIDK EMAETQHGTT VVKVKYEGAG APCKVPIEIR DVNKEKVVGR 350
Consensus         MCTGKFKIVK EIAETQHGTI VIRVQYEGDG SPCKIPFEIT DLEKRHVLGR
Conservation 360                 380                     400
                           |                   |                       |
Parent WT DENV2   LITVNPIVTE KDSPVNIEAE PPFGDSYIII GVEPGQLKLN WFKKGSSIGQ 400
DV4-EDIII-DV2     LITVNPIVTE KDSPVNIEAE PPFGDSYIII GVEPGQLKLN WFKKGSSIGK 400
Parent WT DENV4   VISSTPLAEN TNSVTNIELE PPFGDSYIVI GVGNSALTLH WFRKGSSIGK 400
Consensus         LITVNPIVTE KDSPVNIEAE PPFGDSYIII GVEPGQLKLN WFKKGSSIGK
Conservation 420                             440
                           |                               |
Parent WT DENV2   MFETTMRGAK RMAILGDTAW DFGSLGGVFT SIGKALHQVF GAIYGAAFSG 450
DV4-EDIII-DV2     MFESTYRGAK RMAILGETAW DFGSVGGLFT SLGKAVHQVF GSVYTTMFGG 450
Parent WT DENV4   MFESTYRGAK RMAILGETAW DFGSVGGLFT SLGKAVHQVF GSVYTTMFGG 450
Consensus         MFESTYRGAK RMAILGETAW DFGSVGGLFT SLGKAVHQVF GSVYTTMFGG
Conservation 460                 480
                           |                   |
Parent WT DENV2   VSWTMKILIG VIITWIGMNS RSTSLSVSLV LVGVVTLYLG AVVQA 495
DV4-EDIII-DV2     VSWMIRILIG FLVLWIGTNS RNTSMAMTCI AVGGITLFLG FTVQA 495
Parent WT DENV4   VSWMIRILIG FLVLWIGTNS RNTSMAMTCI AVGGITLFLG FTVQA 495
Consensus         VSWMIRILIG FLVLWIGTNS RNTSMAMTCI AVGGITLFLG FTVQA
Conservation
```

*FIG. 32A*

SEQUENCE LISTING

<160> NUMBER OF SEQ ID NOS: 40

<210> SEQ ID NO 1
<211> LENGTH: 495
<212> TYPE: PRT
<213> ORGANISM: Dengue virus type 4

<400> SEQUENCE: 1

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
                195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255
```

Glu Gly Ala Met His Ser Ala Leu Ala Gly Ala Thr Glu Val Asp Ser
           260                 265                 270

Gly Asp Gly Asn His Met Phe Ala Gly His Leu Lys Cys Lys Val Arg
            275                 280                 285

Met Glu Lys Leu Arg Ile Lys Gly Met Ser Tyr Thr Met Cys Ser Gly
290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 2
<211> LENGTH: 495
<212> TYPE: PRT
<213> ORGANISM: Artificial
<220> FEATURE:
<223> OTHER INFORMATION: DENV4 M12 E glycoprotein sequence

<400> SEQUENCE: 2

Met Arg Cys Val Gly Val Gly Asn Arg Asp Phe Val Glu Gly Val Ser
1               5 10 15

Gly Gly Ala Trp Val Asp Leu Val Leu Glu His Gly Gly Cys Val Thr
20 25 30

Thr Met Ala Gln Gly Lys Pro Thr Leu Asp Phe Glu Leu Thr Lys Thr
35 40 45

Thr Ala Thr Gln Leu Ala Thr Leu Arg Lys Leu Cys Ile Glu Ala Ser
50 55 60

Ile Ser Asn Ile Thr Thr Ala Thr Arg Cys Pro Thr Gln Gly Glu Pro
65 70 75 80

Tyr Leu Lys Glu Glu Gln Asp Gln Gln Tyr Ile Cys Arg Arg Asp Val
85 90 95

Val Asp Arg Gly Trp Gly Asn Gly Cys Gly Leu Phe Gly Lys Gly Gly
100 105 110

Val Val Thr Cys Ala Lys Phe Ser Cys Ser Gly Pro Ile Glu Gly Lys
115 120 125

Val Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Leu Thr Met Lys Lys Lys Ala Trp Met Val
        195                 200                 205

His Arg Gln Trp Phe Phe Asp Leu Pro Leu Pro Trp Thr Ser Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Ile Gln Asn
            260                 265                 270

Ser Gly Gly Thr Ser Ile Phe Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
            340                 345                 350

Ser Ser Thr Pro Leu Ala Glu Asn Thr Asn Ser Val Thr Asn Ile Glu
        355                 360                 365

Leu Glu Pro Pro Phe Gly Asp Ser Tyr Ile Val Ile Gly Val Gly Asn
    370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 3
<211> LENGTH: 495
<212> TYPE: PRT
<213> ORGANISM: Artificial
<220> FEATURE:
<223> OTHER INFORMATION: DENV4 M14 E glycoprotein sequence

<400> SEQUENCE: 3

```
Met Arg Cys Val Gly Val Gly Asn Arg Asp Phe Val Glu Gly Val Ser
1               5                   10                  15
Gly Gly Ala Trp Val Asp Leu Val Leu Glu His Gly Gly Cys Val Thr
                20                  25                  30
Thr Met Ala Gln Gly Lys Pro Thr Leu Asp Phe Glu Leu Thr Lys Thr
        35                  40                  45
Glu Ala Thr Gln Leu Ala Thr Leu Arg Lys Leu Cys Ile Glu Ala Ser
50                  55                  60
Ile Ser Asn Ile Thr Thr Ala Thr Arg Cys Pro Thr Gln Gly Glu Pro
65                  70                  75                  80
Tyr Leu Lys Glu Glu Gln Asp Gln Gln Tyr Ile Cys Arg Arg Asp Val
                85                  90                  95
Val Asp Arg Gly Trp Gly Asn Gly Cys Gly Leu Phe Gly Lys Gly Gly
                100                 105                 110
Val Val Thr Cys Ala Lys Phe Ser Cys Leu Glu Pro Ile Glu Gly Lys
        115                 120                 125
Val Val Gln Tyr Glu Asn Leu Glu Tyr Thr Val Val Thr Val His
        130                 135                 140
Asn Gly Asp Thr His Ala Val Gly Asn Asp Thr Ser Asn His Gly Val
145                 150                 155                 160
Thr Ala Thr Ile Thr Pro Arg Ser Pro Ser Val Glu Val Lys Leu Pro
                165                 170                 175
Asp Tyr Gly Glu Leu Thr Leu Asp Cys Glu Pro Arg Ser Gly Ile Asp
                180                 185                 190
Phe Asn Glu Met Ile Leu Leu Thr Met Lys Lys Ala Trp Met Val
                195                 200                 205
His Arg Gln Trp Phe Phe Asp Leu Pro Leu Pro Trp Thr Ser Gly Ala
        210                 215                 220
Asp Thr Ser Glu Val His Trp Asn Tyr Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Ala Gly Ala Thr Glu Ile Gln Asn
                260                 265                 270
Ser Gly Gly Thr Ser Ile Phe Ala Gly His Leu Lys Cys Lys Val Arg
        275                 280                 285
Met Glu Lys Leu Arg Ile Lys Gly Met Ser Tyr Thr Met Cys Ser Gly
        290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Val Gly Arg Val Ile
                340                 345                 350
Ser Ser Thr Pro Leu Ala Glu Asn Thr Asn Ser Val Thr Asn Ile Glu
        355                 360                 365
Leu Glu Pro Pro Phe Gly Asp Ser Tyr Ile Val Ile Gly Val Gly Asn
370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys Arg Met Ala Ile Leu Gly
                405                 410                 415
```

```
Glu Thr Ala Trp Asp Phe Gly Ser Val Gly Leu Phe Thr Ser Leu
            420                 425                 430

```
Met Glu Lys Leu Arg Ile Lys Gly Met Ser Tyr Thr Met Cys Ser Gly
    290                 295                 300

Lys Phe Ser Ile Lys Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
                340                 345                 350

Ser Ser Thr Pro Leu Ala Glu Asn Thr Asn Ser Pro Thr Asn Ile Glu
355                 360                 365

Leu Glu Pro Pro Phe Gly Asp Ser Tyr Ile Val Ile Gly Val Gly Asn
370                 375                 380

Ser Ala Leu Thr Leu His Trp Phe Arg Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
435                 440                 445

Gly Gly Val Ser Trp Met Ile Arg Ile Leu Ile Gly Phe Leu Val Leu
450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 5
<211> LENGTH: 495
<212> TYPE: PRT
<213> ORGANISM: Artificial
<220> FEATURE:
<223> OTHER INFORMATION: DV4-EDIII-DV2 E glycoprotein sequence

<400> SEQUENCE: 5

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
                20                  25                  30

Thr Met Ala Gln Gly Lys Pro Thr Leu Asp Phe Glu Leu Thr Lys Thr
            35                  40                  45

Thr Ala Lys Glu Val Ala Leu Leu Arg Thr Tyr Cys Ile Glu Ala Ser
50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
                100                 105                 110

Val Val Thr Cys Ala Lys Phe Ser Cys Ser Gly Lys Ile Thr Gly Asn
            115                 120                 125

Leu Val Gln Ile Glu Asn Leu Glu Tyr Thr Val Val Thr Val His
        130                 135                 140

Asn Gly Asp Thr His Ala Val Gly Asn Asp Thr Ser Asn His Gly Val
145                 150                 155                 160
```

-continued

```
Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Thr Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Asp Gly Asn His Met Phe Ala Gly His Leu Lys Cys Lys Val Arg
        275                 280                 285

Met Glu Lys Leu Arg Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 6
<211> LENGTH: 495
<212> TYPE: PRT
<213> ORGANISM: Artificial
<220> FEATURE:
<223> OTHER INFORMATION: DENV2-1F4E E glycoprotein sequence

<400> SEQUENCE: 6

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30
```

```
Thr Met Ala Lys Asn Lys Pro Thr Leu Asp Phe Glu Leu Phe Lys Thr
         35                  40                  45

Glu Val Thr Asn Pro Ala Val Leu Arg Lys Tyr Cys Ile Glu Ala Lys
 50                  55                  60

Leu Thr Asn Thr Thr Thr Glu Ser Arg Cys Pro Thr Gln Gly Glu Pro
 65                  70                  75                  80

Ser Leu Asn Glu Glu Gln Asp Lys Arg Phe Ile Cys Lys His Ser Met
                 85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
            115                 120                 125

Val Val Gln Pro Glu Asn Leu Lys Tyr Ser Val Ile Val Thr Val His
        130                 135                 140

Ser Gly Glu Glu His Ala Val Gly Asn Asp Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Glu Cys Ser Pro Arg Thr Gly Leu Asp
            180                 185                 190

Phe Asn Glu Met Val Leu Leu Gln Met Glu Asp Lys Ala Trp Leu Val
            195                 200                 205

His Arg Gln Trp Phe Leu Asp Leu Pro Leu Pro Trp Leu Pro Gly Ala
        210                 215                 220

Asp Thr Gln Glu Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Leu Phe Thr Gly His Leu Lys Cys Arg Leu Arg
        275                 280                 285

Met Asp Lys Leu Gln Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
```

450 455 460

Trp Ile Gly Met Asn Ser Arg Ser Thr Ser Leu Ser Val Ser Leu Val
465 470 475 480

Leu Val Gly Val Val Thr Leu Tyr Leu Gly Ala Val Val Gln Ala
485 490 495

<210> SEQ ID NO 7
<211> LENGTH: 11
<212> TYPE: DNA
<213> ORGANISM: Artificial
<220> FEATURE:
<223> OTHER INFORMATION: PflMI restriction site

<400> SEQUENCE: 7
ccaaacagtg g 11

<210> SEQ ID NO 8
<211> LENGTH: 11
<212> TYPE: DNA
<213> ORGANISM: Artificial
<220> FEATURE:
<223> OTHER INFORMATION: PflMI restriction site

<400> SEQUENCE: 8
ccagattttg g 11

<210> SEQ ID NO 9
<211> LENGTH: 11
<212> TYPE: DNA
<213> ORGANISM: Artificial
<220> FEATURE:
<223> OTHER INFORMATION: PflMI restriction site

<400> SEQUENCE: 9
ccaccttttg g 11

<210> SEQ ID NO 10
<211> LENGTH: 11
<212> TYPE: DNA
<213> ORGANISM: Artificial
<220> FEATURE:
<223> OTHER INFORMATION: PflMI restriction site

<400> SEQUENCE: 10
ccactagctg g 11

<210> SEQ ID NO 11
<211> LENGTH: 11
<212> TYPE: DNA
<213> ORGANISM: Artificial
<220> FEATURE:
<223> OTHER INFORMATION: PflMI restriction site

<400> SEQUENCE: 11
ccaaaccatg g 11

<210> SEQ ID NO 12
<211> LENGTH: 493
<212> TYPE: PRT
<213> ORGANISM: Dengue virus type 3

<400> SEQUENCE: 12

Met Arg Cys Val Gly Ile Gly Asn Arg Asp Phe Val Glu Gly Leu Ser
1 5 10 15

-continued

Gly Ala Thr Trp Val Asp Val Val Leu Glu His Gly Gly Cys Val Thr
             20                  25                  30
Thr Met Ala Lys Asn Lys Pro Thr Leu Asp Ile Glu Leu Gln Lys Thr
         35                  40                  45
Glu Ala Thr Gln Leu Ala Thr Leu Arg Lys Leu Cys Ile Glu Gly Lys
     50                  55                  60
Ile Thr Asn Ile Thr Thr Asp Ser Arg Cys Pro Thr Gln Gly Glu Ala
65                  70                  75                  80
Val Leu Pro Glu Glu Gln Asp Gln Asn Tyr Val Cys Lys His Thr Tyr
                 85                  90                  95
Val Asp Arg Gly Trp Gly Asn Gly Cys Gly Leu Phe Gly Lys Gly Ser
            100                 105                 110
Leu Val Thr Cys Ala Lys Phe Gln Cys Leu Glu Pro Ile Glu Gly Lys
        115                 120                 125
Val Val Gln Tyr Glu Asn Leu Lys Tyr Thr Val Ile Ile Thr Val His
    130                 135                 140
Thr Gly Asp Gln His Gln Val Gly Asn Glu Thr Gln Gly Val Thr Ala
145                 150                 155                 160
Glu Ile Thr Pro Gln Ala Ser Thr Thr Glu Ala Ile Leu Pro Glu Tyr
                165                 170                 175
Gly Thr Leu Gly Leu Glu Cys Ser Pro Arg Thr Gly Leu Asp Phe Asn
            180                 185                 190
Glu Met Ile Leu Leu Thr Met Lys Asn Lys Ala Trp Met Val His Arg
        195                 200                 205
Gln Trp Phe Phe Asp Leu Pro Leu Pro Trp Thr Ser Gly Ala Thr Thr
    210                 215                 220
Glu Thr Pro Thr Trp Asn Arg Lys Glu Leu Leu Val Thr Phe Lys Asn
225                 230                 235                 240
Ala His Ala Lys Lys Gln Glu Val Val Val Leu Gly Ser Gln Glu Gly
                245                 250                 255
Ala Met His Thr Ala Leu Thr Gly Ala Thr Glu Ile Gln Asn Ser Gly
            260                 265                 270
Gly Thr Ser Ile Phe Ala Gly His Leu Lys Cys Arg Leu Lys Met Asp
        275                 280                 285
Lys Leu Glu Leu Lys Gly Met Ser Tyr Ala Met Cys Thr Asn Thr Phe
    290                 295                 300
Val Leu Lys Lys Glu Val Ser Glu Thr Gln His Gly Thr Ile Leu Ile
305                 310                 315                 320
Lys Val Glu Tyr Lys Gly Glu Asp Ala Pro Cys Lys Ile Pro Phe Ser
                325                 330                 335
Thr Glu Asp Gly Gln Gly Lys Ala His Asn Gly Arg Leu Ile Thr Ala
            340                 345                 350
Asn Pro Val Val Thr Lys Lys Glu Glu Pro Val Asn Ile Glu Ala Glu
        355                 360                 365
Pro Pro Phe Gly Glu Ser Asn Ile Val Ile Gly Ile Gly Asp Asn Ala
    370                 375                 380
Leu Lys Ile Asn Trp Tyr Lys Lys Gly Ser Ser Ile Gly Lys Met Phe
385                 390                 395                 400
Glu Ala Thr Ala Arg Gly Ala Arg Arg Met Ala Ile Leu Gly Asp Thr
                405                 410                 415
Ala Trp Asp Phe Gly Ser Val Gly Gly Val Leu Asn Ser Leu Gly Lys
            420                 425                 430
Met Val His Gln Ile Phe Gly Ser Ala Tyr Thr Ala Leu Phe Ser Gly

```
                    435                 440                 445
Val Ser Trp Val Met Lys Ile Gly Ile Gly Val Leu Thr Trp Ile
        450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490
```

<210> SEQ ID NO 13
<211> LENGTH: 495
<212> TYPE: PRT
<213> ORGANISM: Dengue virus type 2

<400> SEQUENCE: 13

```
Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
        50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Ile Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Glu Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320
```

Val Ile Arg Val Gln Tyr Glu Gly Asp Gly Ser Pro Cys Lys Ile Pro
            325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Glu Pro
        370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
            405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
        450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Ala Val Val Gln Ala
            485                 490                 495

<210> SEQ ID NO 14
<211> LENGTH: 495
<212> TYPE: PRT
<213> ORGANISM: Dengue virus type 1

<400> SEQUENCE: 14

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
            85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
            165                 170                 175

Asp Tyr Gly Ala Leu Thr Leu Asp Cys Ser Pro Arg Thr Gly Leu Asp
        180                 185                 190

Phe Asn Glu Met Val Leu Leu Thr Met Glu Lys Lys Ser Trp Leu Val
    195                 200                 205

-continued

His Lys Gln Trp Phe Leu Asp Leu Pro Leu Pro Trp Thr Ser Gly Ala
            210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
            245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Val Met Cys Thr Gly
            290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
            325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
            370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
            405                 410                 415

Asp Thr Ala Trp Asp Phe Gly Ser Ile Gly Gly Val Phe Thr Ser Val
            420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
            485                 490                 495

<210> SEQ ID NO 15
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 15

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
        50                  55                  60

Ile Ser Asn Thr Thr Thr Asp Ser Arg Cys Pro Thr Gln Gly Glu Ala
65              70                  75                  80

```
Thr Leu Val Glu Glu Gln Asp Thr Asn Phe Val Cys Arg Arg Thr Phe
                85                  90                  95
Val Asp Arg Gly Trp Gly Asn Gly Cys Gly Leu Phe Gly Lys Gly Ser
            100                 105                 110
Leu Ile Thr Cys Ala Lys Phe Lys Cys Val Thr Lys Leu Glu Gly Lys
        115                 120                 125
Ile Val Gln Tyr Glu Asn Leu Lys Tyr Ser Val Ile Val Thr Val His
    130                 135                 140
Thr Gly Asp Gln His Gln Val Gly Asn Glu Ala Thr Glu His Gly Val
145                 150                 155                 160
Thr Ala Met Ile Thr Pro Gln Ser Pro Ser Val Glu Val Lys Leu Pro
                165                 170                 175
Asp Tyr Gly Glu Leu Thr Leu Asp Cys Ser Pro Arg Thr Gly Leu Asp
            180                 185                 190
Phe Asn Glu Met Val Leu Leu Thr Met Lys Lys Lys Ser Trp Leu Val
        195                 200                 205
His Lys Gln Trp Phe Leu Asp Leu Pro Leu Pro Trp Thr Ser Gly Ala
    210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
                245                 250                 255
Glu Gly Ala Met His Thr Ala Leu Thr Gly Ala Thr Glu Ile Gln Thr
            260                 265                 270
Ser Gly Thr Thr Thr Ile Phe Ala Gly His Leu Lys Cys Arg Leu Lys
        275                 280                 285
Met Asp Lys Leu Arg Leu Lys Gly Met Ser Tyr Val Met Cys Thr Gly
    290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
                325                 330                 335
Phe Ser Ser Gln Asp Glu Lys Gly Val Thr Gln Asn Gly Arg Leu Ile
            340                 345                 350
Thr Ala Asn Pro Ile Val Thr Asp Lys Glu Lys Pro Val Asn Ile Glu
        355                 360                 365
Ala Glu Pro Pro Phe Gly Glu Ser Tyr Ile Val Val Gly Ala Gly Glu
    370                 375                 380
Lys Ala Leu Lys Leu Ser Trp Phe Lys Lys Gly Ser Ser Ile Gly Lys
385                 390                 395                 400
Met Phe Glu Ala Thr Ala Arg Gly Ala Arg Arg Met Ala Ile Leu Gly
                405                 410                 415
Asp Thr Ala Trp Asp Phe Gly Ser Ile Gly Gly Val Phe Thr Ser Val
            420                 425                 430
Gly Lys Leu Ile His Gln Ile Phe Gly Thr Ala Tyr Gly Val Leu Phe
        435                 440                 445
Ser Gly Val Ser Trp Thr Met Lys Ile Gly Ile Gly Ile Leu Leu Thr
    450                 455                 460
Trp Leu Gly Leu Asn Ser Arg Ser Thr Ser Leu Ser Met Thr Cys Ile
465                 470                 475                 480
Ala Val Gly Met Val Thr Leu Tyr Leu Gly Val Met Val Gln Ala
                485                 490                 495
```

<210> SEQ ID NO 16
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 16

| Met | Arg | Cys | Ile | Gly | Ile | Ser | Asn | Arg | Asp | Phe | Val | Glu | Gly | Val | Ser |
|---|---|---|---|---|---|---|---|---|---|---|---|---|---|---|---|
| 1 | | | | 5 | | | | | 10 | | | | | 15 | |

| Gly | Gly | Ser | Trp | Val | Asp | Ile | Val | Leu | Glu | His | Gly | Ser | Cys | Val | Thr |
|---|---|---|---|---|---|---|---|---|---|---|---|---|---|---|---|
| | | | 20 | | | | | 25 | | | | | 30 | | |

| Thr | Met | Ala | Lys | Asn | Lys | Pro | Thr | Leu | Asp | Phe | Glu | Leu | Ile | Lys | Thr |
|---|---|---|---|---|---|---|---|---|---|---|---|---|---|---|---|
| | | 35 | | | | | 40 | | | | | 45 | | | |

| Glu | Ala | Lys | Gln | Pro | Ala | Thr | Leu | Arg | Lys | Tyr | Cys | Ile | Glu | Ala | Lys |
|---|---|---|---|---|---|---|---|---|---|---|---|---|---|---|---|
| | 50 | | | | | 55 | | | | | 60 | | | | |

| Leu | Thr | Asn | Thr | Thr | Thr | Glu | Ser | Arg | Cys | Pro | Thr | Gln | Gly | Glu | Pro |
|---|---|---|---|---|---|---|---|---|---|---|---|---|---|---|---|
| 65 | | | | | 70 | | | | | 75 | | | | | 80 |

| Ser | Leu | Asn | Glu | Glu | Gln | Asp | Lys | Arg | Phe | Ile | Cys | Lys | His | Ser | Met |
|---|---|---|---|---|---|---|---|---|---|---|---|---|---|---|---|
| | | | | 85 | | | | | 90 | | | | | 95 | |

| Val | Asp | Arg | Gly | Trp | Gly | Asn | Gly | Cys | Gly | Leu | Phe | Gly | Lys | Gly | Gly |
|---|---|---|---|---|---|---|---|---|---|---|---|---|---|---|---|
| | | | 100 | | | | | 105 | | | | | 110 | | |

| Ile | Val | Thr | Cys | Ala | Met | Phe | Thr | Cys | Lys | Lys | Asn | Met | Glu | Gly | Lys |
|---|---|---|---|---|---|---|---|---|---|---|---|---|---|---|---|
| | | 115 | | | | | 120 | | | | | 125 | | | |

| Val | Val | Gln | Pro | Glu | Asn | Leu | Glu | Tyr | Thr | Ile | Val | Ile | Thr | Pro | His |
|---|---|---|---|---|---|---|---|---|---|---|---|---|---|---|---|
| | 130 | | | | | 135 | | | | | 140 | | | | |

| Ser | Gly | Glu | Glu | His | Ala | Val | Gly | Asn | Asp | Ala | Gly | Lys | His | Gly | Val |
|---|---|---|---|---|---|---|---|---|---|---|---|---|---|---|---|
| 145 | | | | | 150 | | | | | 155 | | | | | 160 |

| Thr | Ala | Met | Ile | Thr | Pro | Gln | Ser | Ser | Val | Glu | Val | Lys | Leu | Pro |
|---|---|---|---|---|---|---|---|---|---|---|---|---|---|---|
| | | | | 165 | | | | | 170 | | | | | 175 |

| Asp | Tyr | Gly | Glu | Val | Thr | Met | Glu | Cys | Ser | Pro | Arg | Thr | Gly | Leu | Asp |
|---|---|---|---|---|---|---|---|---|---|---|---|---|---|---|---|
| | | | 180 | | | | | 185 | | | | | 190 | | |

| Phe | Asn | Glu | Met | Val | Leu | Leu | Gln | Met | Glu | Asp | Lys | Ala | Trp | Leu | Val |
|---|---|---|---|---|---|---|---|---|---|---|---|---|---|---|---|
| | | 195 | | | | | 200 | | | | | 205 | | | |

| His | Arg | Gln | Trp | Phe | Leu | Asp | Leu | Pro | Leu | Pro | Trp | Leu | Pro | Gly | Ala |
|---|---|---|---|---|---|---|---|---|---|---|---|---|---|---|---|
| | 210 | | | | | 215 | | | | | 220 | | | | |

| Asp | Thr | Gln | Glu | Ser | Asn | Trp | Ile | Gln | Lys | Glu | Thr | Leu | Val | Thr | Phe |
|---|---|---|---|---|---|---|---|---|---|---|---|---|---|---|---|
| 225 | | | | | 230 | | | | | 235 | | | | | 240 |

| Lys | Asn | Pro | His | Ala | Lys | Lys | Gln | Asp | Val | Val | Leu | Gly | Ser | Gln |
|---|---|---|---|---|---|---|---|---|---|---|---|---|---|---|
| | | | | 245 | | | | | 250 | | | | | 255 |

| Glu | Gly | Ala | Met | His | Thr | Ala | Leu | Thr | Gly | Ala | Thr | Glu | Ile | Gln | Met |
|---|---|---|---|---|---|---|---|---|---|---|---|---|---|---|---|
| | | | 260 | | | | | 265 | | | | | 270 | | |

| Ser | Ser | Gly | Asn | Leu | Leu | Phe | Thr | Gly | His | Leu | Lys | Cys | Arg | Leu | Arg |
|---|---|---|---|---|---|---|---|---|---|---|---|---|---|---|---|
| | | 275 | | | | | 280 | | | | | 285 | | | |

| Met | Asp | Lys | Leu | Arg | Leu | Lys | Gly | Met | Ser | Tyr | Ser | Met | Cys | Thr | Gly |
|---|---|---|---|---|---|---|---|---|---|---|---|---|---|---|---|
| | 290 | | | | | 295 | | | | | 300 | | | | |

| Lys | Phe | Lys | Ile | Val | Lys | Glu | Ile | Ala | Glu | Thr | Gln | His | Gly | Thr | Ile |
|---|---|---|---|---|---|---|---|---|---|---|---|---|---|---|---|
| 305 | | | | | 310 | | | | | 315 | | | | | 320 |

| Val | Ile | Arg | Val | Gln | Tyr | Glu | Gly | Asp | Gly | Ser | Pro | Cys | Lys | Ile | Pro |
|---|---|---|---|---|---|---|---|---|---|---|---|---|---|---|---|
| | | | | 325 | | | | | 330 | | | | | 335 | |

| Phe | Glu | Ile | Thr | Asp | Leu | Glu | Lys | Arg | His | Val | Leu | Gly | Arg | Leu | Ile |
|---|---|---|---|---|---|---|---|---|---|---|---|---|---|---|---|
| | | | 340 | | | | | 345 | | | | | 350 | | |

| Thr | Val | Asn | Pro | Ile | Val | Thr | Glu | Lys | Asp | Ser | Pro | Val | Asn | Ile | Glu |
|---|---|---|---|---|---|---|---|---|---|---|---|---|---|---|---|
| | | 355 | | | | | 360 | | | | | 365 | | | |

```
Ala Glu Pro Pro Phe Gly Asp Ser Tyr Ile Ile Gly Val Glu Pro
370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
                420                 425                 430

Gly Lys Ala Leu His Gln Val Phe Gly Ala Ile Tyr Gly Ala Ala Phe
                435                 440                 445

Ser Gly Val Ser Trp Thr Met Lys Ile Leu Ile Gly Val Ile Ile Thr
450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Ala Val Val Gln Ala
                485                 490                 495

<210> SEQ ID NO 17
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 17

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Phe Lys Thr
            35                  40                  45

Glu Val Thr Asn Pro Ala Val Leu Arg Lys Tyr Cys Ile Glu Ala Lys
50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Thr Cys Lys Lys Asn Met Glu Gly Lys
            115                 120                 125

Val Val Gln Pro Glu Asn Leu Lys Tyr Ser Val Ile Val Thr Val His
        130                 135                 140

Ser Gly Glu Glu His Ala Val Gly Asn Asp Thr Thr Glu His Gly Thr
145                 150                 155                 160

Thr Ala Thr Val Thr Pro Gln Ala Pro Thr Ser Glu Ile Gln Leu Thr
                165                 170                 175

Asp Tyr Gly Ala Leu Thr Leu Glu Cys Ser Pro Arg Thr Gly Leu Asp
                180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
        210                 215                 220

Asp Thr Gln Gly Ser Asn Trp Ile Gln Lys Glu Thr Leu Val Thr Phe
225                 230                 235                 240
```

```
Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Asp Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Ala Val Val Gln Ala
                485                 490                 495

<210> SEQ ID NO 18
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 18

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Phe Lys Thr
        35                  40                  45

Thr Val Thr Asn Pro Ala Val Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110
```

Val Val Thr Cys Ala Lys Phe Ser Cys Ser Gly Lys Ile Thr Gly Asn
            115                 120                 125

Leu Val Gln Ile Glu Asn Leu Lys Tyr Ser Val Ile Val Thr Val His
130                 135                 140

Asn Gly Asp Thr His Ala Val Gly Asn Asp Thr Thr Glu His Gly Thr
145                 150                 155                 160

Thr Ala Thr Ile Thr Pro Arg Ala Pro Thr Ser Glu Ile Gln Leu Thr
                165                 170                 175

Asp Tyr Gly Ala Leu Thr Leu Asp Cys Glu Pro Arg Ser Gly Ile Asp
                180                 185                 190

Phe Asn Glu Met Ile Leu Met Lys Met Lys Lys Thr Trp Leu Val
                195                 200                 205

His Lys Gln Trp Phe Leu Asp Leu Pro Leu Pro Trp Thr Ala Gly Ala
                210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Thr
                260                 265                 270

Gly Gly Thr Thr Thr Met Phe Ala Gly His Leu Lys Cys Lys Val Arg
                275                 280                 285

Met Glu Lys Leu Arg Ile Lys Gly Met Ser Tyr Thr Met Cys Ser Gly
                290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Val Ile
                340                 345                 350

Ser Ser Thr Pro Leu Ala Glu Asn Thr Asn Ser Val Thr Asn Ile Glu
                355                 360                 365

Leu Glu Pro Pro Phe Gly Asp Ser Tyr Ile Val Ile Gly Val Gly Asn
                370                 375                 380

Ser Ala Leu Thr Leu His Trp Phe Arg Lys Gly Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
                435                 440                 445

Gly Gly Val Ser Trp Met Ile Arg Ile Leu Ile Gly Phe Leu Val Leu
                450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 19
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 19

Met Arg Cys Val Gly Ile Gly Asn Arg Asp Phe Val Glu Gly Leu Ser
1               5                   10                  15

Gly Ala Thr Trp Val Asp Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Ala Thr Gln Leu Ala Thr Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Leu Glu Pro Ile Glu Gly Lys
        115                 120                 125

Val Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Phe Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
            260                 265                 270

Ser Gly Gly Thr Ser Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly

```
            405                 410                 415
Asp Thr Ala Trp Asp Phe Gly Ser Ile Gly Gly Val Phe Thr Ser Val
            420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
            450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
            485                 490                 495

<210> SEQ ID NO 20
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 20

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Thr Gln Leu Ala Thr Leu Arg Lys Leu Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Glu Pro Ile Glu Gly Lys
        115                 120                 125

Val Val Gln Pro Glu Asn Leu Glu Tyr Thr Ile Val Val Thr Pro His
    130                 135                 140

Ser Gly Glu Glu His Ala Val Gly Asn Asp Thr Gly Lys His Gly Lys
145                 150                 155                 160

Glu Ile Lys Val Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Thr Met Lys Asn Lys Ala Trp Met Val
        195                 200                 205

His Arg Gln Trp Phe Phe Asp Leu Pro Leu Pro Trp Thr Ser Thr Ala
    210                 215                 220

Asp Thr Gln Gly Pro Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Asn
            260                 265                 270

Ser Gly Gly Thr Ser Ile Phe Ala Gly His Leu Lys Cys Arg Leu Arg
```

-continued

```
                275                 280                 285
Met Asp Lys Leu Gln Leu Lys Gly Met Ser Tyr Ser Met Cys Thr Gly
            290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
            340                 345                 350
Thr Val Asn Pro Ile Val Thr Glu Lys Asp Ser Pro Val Asn Ile Glu
            355                 360                 365
Ala Glu Pro Pro Phe Gly Asp Ser Tyr Ile Ile Gly Val Asp Pro
370                 375                 380
Gly Gln Leu Lys Leu Asn Trp Phe Lys Lys Gly Ser Ser Ile Gly Gln
385                 390                 395                 400
Met Phe Glu Thr Thr Met Arg Gly Ala Lys Arg Met Ala Ile Leu Gly
            405                 410                 415
Asp Thr Ala Trp Asp Phe Gly Ser Leu Gly Gly Val Phe Thr Ser Ile
            420                 425                 430
Gly Lys Ala Leu His Gln Val Phe Gly Ala Ile Tyr Gly Ala Ala Phe
            435                 440                 445
Ser Gly Val Ser Trp Thr Met Lys Ile Leu Ile Gly Val Ile Ile Thr
            450                 455                 460
Trp Ile Gly Met Asn Ser Arg Ser Thr Ser Leu Ser Val Ser Leu Val
465                 470                 475                 480
Leu Val Gly Ile Val Thr Leu Tyr Leu Gly Val Met Val Gln Ala
                485                 490                 495

<210> SEQ ID NO 21
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 21

Met Arg Cys Val Gly Ile Gly Asn Arg Asp Phe Val Glu Gly Leu Ser
1               5                   10                  15
Gly Ala Thr Trp Val Asp Val Val Leu Glu His Gly Gly Cys Val Thr
            20                  25                  30
Thr Met Ala Lys Asn Lys Pro Thr Leu Asp Ile Glu Leu Gln Lys Thr
        35                  40                  45
Glu Ala Thr Gln Leu Ala Thr Leu Arg Lys Leu Cys Ile Glu Gly Lys
    50                  55                  60
Ile Thr Asn Ile Thr Thr Asp Ser Arg Cys Pro Thr Gln Gly Glu Ala
65                  70                  75                  80
Val Leu Pro Glu Glu Gln Asp Gln Asn Tyr Val Cys Lys His Thr Tyr
                85                  90                  95
Val Asp Arg Gly Trp Gly Asn Gly Cys Gly Leu Phe Gly Lys Gly Ser
            100                 105                 110
Leu Val Thr Cys Ala Lys Phe Gln Cys Leu Glu Pro Ile Glu Gly Lys
        115                 120                 125
Val Val Gln Tyr Glu Asn Leu Lys Tyr Thr Val Ile Ile Thr Val His
    130                 135                 140
Thr Gly Asp Gln His Gln Val Gly Asn Glu Ala Ser Asn Gln Gly Val
```

```
                145                 150                 155                 160
Thr Ala Met Ile Thr Pro Gln Ser Ser Val Glu Val Lys Leu Pro
                    165                 170                 175

Asp Tyr Gly Glu Leu Gly Leu Glu Cys Ser Pro Arg Thr Gly Leu Asp
                180                 185                 190

Phe Asn Glu Met Ile Leu Leu Thr Met Lys Asn Lys Ala Trp Met Val
                195                 200                 205

His Arg Gln Trp Phe Phe Asp Leu Pro Leu Pro Trp Thr Ser Gly Ala
            210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
                260                 265                 270

Ser Gly Gly Thr Ser Ile Phe Ala Gly His Leu Lys Cys Arg Leu Lys
                275                 280                 285

Met Asp Lys Leu Arg Leu Lys Gly Met Ser Tyr Ala Met Cys Thr Asn
            290                 295                 300

Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Gly Gln Gly Lys Ala His Asn Gly Arg Leu Ile
                340                 345                 350

Thr Ala Asn Pro Val Val Thr Lys Lys Glu Glu Pro Val Asn Ile Glu
                355                 360                 365

Ala Glu Pro Pro Phe Gly Glu Ser Asn Ile Val Ile Gly Ile Gly Asp
            370                 375                 380

Asn Ala Leu Lys Ile Asn Trp Tyr Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Val Gly Gly Val Leu Asn Ser Leu
                420                 425                 430

Gly Lys Met Val His Gln Ile Phe Gly Ser Ala Tyr Thr Ala Leu Phe
                435                 440                 445

Ser Gly Val Ser Trp Val Met Lys Ile Gly Ile Gly Val Leu Leu Thr
            450                 455                 460

Trp Ile Gly Leu Asn Ser Lys Asn Thr Ser Met Ser Phe Ser Cys Ile
465                 470                 475                 480

Ala Ile Gly Ile Ile Thr Leu Tyr Leu Gly Ala Val Val Gln Ala
                485                 490                 495

<210> SEQ ID NO 22
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 22

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
```

```
            20                  25                  30
Thr Met Ala Gln Gly Lys Pro Thr Leu Asp Phe Glu Leu Thr Lys Thr
            35                  40                  45
Thr Ala Lys Glu Val Ala Leu Leu Arg Thr Tyr Cys Ile Glu Ala Ser
    50                  55                  60
Ile Ser Asn Ile Thr Thr Ala Thr Arg Cys Pro Thr Gln Gly Glu Pro
65                  70                  75                  80
Tyr Leu Lys Glu Glu Gln Asp Gln Gln Tyr Ile Cys Arg Arg Asp Val
                85                  90                  95
Val Asp Arg Gly Trp Gly Asn Gly Cys Gly Leu Phe Gly Lys Gly Gly
                100                 105                 110
Val Val Thr Cys Ala Lys Phe Ser Cys Ser Gly Lys Ile Thr Gly Asn
                115                 120                 125
Leu Val Gln Ile Glu Asn Leu Glu Tyr Thr Val Val Thr Val His
            130                 135                 140
Asn Gly Asp Thr His Ala Val Gly Asn Asp Thr Ser Asn His Gly Val
145                 150                 155                 160
Thr Ala Thr Ile Thr Pro Arg Ser Pro Ser Val Glu Val Lys Leu Pro
                165                 170                 175
Asp Tyr Gly Glu Leu Thr Leu Asp Cys Glu Pro Arg Ser Gly Ile Asp
                180                 185                 190
Phe Asn Glu Met Ile Leu Met Lys Met Lys Lys Thr Trp Leu Val
                195                 200                 205
His Lys Gln Trp Phe Leu Asp Leu Pro Leu Pro Trp Thr Ala Gly Ala
                210                 215                 220
Asp Thr Ser Glu Val His Trp Asn Tyr Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Ala Gly Ala Thr Glu Val Asp Ser
                260                 265                 270
Gly Asp Gly Asn His Met Phe Ala Gly His Leu Lys Cys Lys Val Arg
                275                 280                 285
Met Glu Lys Leu Arg Leu Lys Gly Met Ser Tyr Ser Met Cys Thr Gly
                290                 295                 300
Lys Phe Lys Ile Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Thr Asp Leu Glu Lys Arg His Val Leu Gly Arg Leu Ile
                340                 345                 350
Thr Val Asn Pro Ile Val Thr Glu Lys Asp Ser Pro Val Asn Ile Glu
                355                 360                 365
Ala Glu Pro Pro Phe Gly Asp Ser Tyr Ile Ile Gly Val Glu Pro
                370                 375                 380
Gly Gln Leu Lys Leu Asn Trp Phe Lys Lys Gly Ser Ser Ile Gly Lys
385                 390                 395                 400
Met Phe Glu Ser Thr Tyr Arg Gly Ala Lys Arg Met Ala Ile Leu Gly
                405                 410                 415
Glu Thr Ala Trp Asp Phe Gly Ser Val Gly Gly Leu Phe Thr Ser Leu
                420                 425                 430
Gly Lys Ala Val His Gln Val Phe Gly Ser Val Tyr Thr Thr Met Phe
                435                 440                 445
```

```
Gly Gly Val Ser Trp Met Ile Arg Ile Leu Ile Gly Phe Leu Val Leu
            450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 23
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 23

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
            85                  90                  95

Val Asp Arg Gly Trp Gly Asn Gly Cys Gly Leu Phe Gly Lys Gly Ser
        100                 105                 110

Leu Ile Thr Cys Ala Lys Phe Lys Cys Val Thr Lys Leu Glu Gly Lys
    115                 120                 125

Ile Val Gln Tyr Glu Asn Leu Lys Tyr Ser Val Ile Val Thr Val His
130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
            165                 170                 175

Asp Tyr Gly Ala Leu Thr Leu Asp Cys Ser Pro Arg Thr Gly Leu Asp
        180                 185                 190

Phe Asn Glu Met Val Leu Leu Thr Met Glu Lys Lys Ser Trp Leu Val
    195                 200                 205

His Lys Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
            245                 250                 255

Glu Gly Ala Met His Thr Ala Leu Thr Gly Ala Thr Glu Ile Gln Thr
        260                 265                 270

Ser Gly Thr Thr Thr Ile Phe Ala Gly His Leu Lys Cys Arg Leu Lys
    275                 280                 285

Met Asp Lys Leu Thr Leu Lys Gly Met Ser Tyr Ser Met Cys Thr Gly
290                 295                 300

Lys Phe Lys Ile Val Lys Glu Ile Ala Glu Thr Gln His Gly Thr Ile
305                 310                 315                 320
```

Val Ile Arg Val Gln Tyr Glu Gly Asp Gly Ser Pro Cys Lys Ile Pro
            325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Lys
385                 390                 395                 400

Met Phe Glu Ala Thr Ala Arg Gly Ala Arg Arg Met Ala Ile Leu Gly
            405                 410                 415

Asp Thr Ala Trp Asp Phe Gly Ser Ile Gly Gly Val Phe Thr Ser Val
            420                 425                 430

Gly Lys Leu Ile His Gln Ile Phe Gly Thr Ala Tyr Gly Val Leu Phe
        435                 440                 445

Ser Gly Val Ser Trp Thr Met Lys Ile Gly Ile Gly Ile Leu Leu Thr
    450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
            485                 490                 495

<210> SEQ ID NO 24
<211> LENGTH: 493
<212> TYPE: PRT
<213> ORGANISM: Artificial
<220> FEATURE:
<223> OTHER INFORMATION: Chimeric Dengue virus E glycoprotein sequence

<400> SEQUENCE: 24

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

```
Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
                260                 265                 270

Gly Thr Ser Ile Phe Ala Gly His Leu Lys Cys Arg Leu Lys Met Asp
                275                 280                 285

Lys Leu Glu Leu Lys Gly Met Ser Tyr Ser Met Cys Thr Gly Lys Phe
    290                 295                 300

Lys Ile Val Lys Glu Ile Ala Glu Thr Gln His Gly Thr Ile Val Ile
305                 310                 315                 320

Arg Val Gln Tyr Glu Gly Asp Gly Ser Pro Cys Lys Ile Pro Phe Glu
                325                 330                 335

Ile Thr Asp Leu Glu Lys Arg His Val Leu Gly Arg Leu Ile Thr Val
                340                 345                 350

Asn Pro Ile Val Thr Glu Lys Asp Ser Pro Val Asn Ile Glu Ala Glu
            355                 360                 365

Pro Pro Phe Gly Asp Ser Tyr Ile Ile Ile Gly Val Glu Pro Gly Gln
        370                 375                 380

Leu Lys Leu Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
                420                 425                 430

Met Val His Gln Ile Phe Gly Ser Ala Tyr Thr Ala Leu Phe Ser Gly
            435                 440                 445

Val Ser Trp Val Met Lys Ile Gly Ile Gly Val Leu Leu Thr Trp Ile
        450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490

<210> SEQ ID NO 25
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 25

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Phe Lys Thr
        35                  40                  45

Glu Val Thr Gln Leu Ala Thr Leu Arg Lys Leu Cys Ile Glu Ala Lys
    50                  55                  60
```

```
Leu Thr Asn Thr Thr Thr Glu Ser Arg Cys Pro Thr Gln Gly Glu Pro
 65                  70                  75                  80

Ser Leu Asn Glu Glu Gln Asp Lys Arg Phe Val Cys Lys His Ser Met
                 85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Pro Ile Glu Gly Lys
                115                 120                 125

Val Val Gln Pro Glu Asn Leu Lys Tyr Thr Ile Ile Val Thr Val His
130                 135                 140

Ser Gly Glu Glu His Ala Val Gly Asn Asp Thr Thr Glu His Gly Thr
145                 150                 155                 160

Thr Ala Thr Val Thr Pro Gln Ser Ser Thr Ser Glu Ile Gln Leu Thr
                165                 170                 175

Asp Tyr Gly Thr Val Thr Met Glu Cys Ser Pro Arg Thr Gly Leu Asp
            180                 185                 190

Phe Asn Glu Met Ile Leu Leu Thr Met Lys Asn Lys Ala Trp Met Val
                195                 200                 205

His Arg Gln Trp Phe Phe Asp Leu Pro Leu Pro Trp Thr Ser Gly Ala
210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Leu Gly Ser Gln
                245                 250                 255

Glu Gly Ala Met His Thr Ala Leu Thr Gly Ala Thr Glu Ile Gln Thr
                260                 265                 270

Ser Ser Thr Thr Thr Ile Phe Ala Gly His Leu Lys Cys Arg Leu Arg
                275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
                340                 345                 350

Thr Val Asn Pro Ile Val Thr Glu Lys Asp Ser Pro Val Asn Ile Glu
                355                 360                 365

Ala Glu Pro Pro Phe Gly Asp Ser Tyr Ile Ile Ile Gly Val Asp Pro
                370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
                420                 425                 430

Gly Lys Ala Leu His Gln Val Phe Gly Ala Ile Tyr Gly Ala Ala Phe
                435                 440                 445

Ser Gly Val Ser Trp Thr Met Lys Ile Leu Ile Gly Val Ile Ile Thr
                450                 455                 460

Trp Ile Gly Met Asn Ser Arg Ser Thr Ser Leu Ser Val Ser Leu Val
465                 470                 475                 480
```

```
Leu Val Gly Val Val Thr Leu Tyr Leu Gly Ala Val Val Gln Ala
                485                 490                 495

<210> SEQ ID NO 26
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 26

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Phe Lys Thr
        35                  40                  45

Glu Val Thr Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Val Val Gln Pro Glu Asn Leu Lys Tyr Thr Ile Ile Val Thr Val His
    130                 135                 140

Ser Gly Glu Glu His Ala Val Gly Asn Asp Ala Thr Glu His Gly Val
145                 150                 155                 160

Thr Ala Met Val Thr Pro Gln Ser Ser Thr Val Glu Val Lys Leu Pro
                165                 170                 175

Asp Tyr Gly Glu Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Leu Phe Thr Gly His Leu Lys Cys Arg Leu Arg
        275                 280                 285

Met Asp Lys Leu Arg Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350
```

```
Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Asp Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
            435                 440                 445

Ser Gly Val Ser Trp Thr Met Lys Ile Leu Ile Gly Val Ile Ile Thr
            450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Ala Val Val Gln Ala
                485                 490                 495

<210> SEQ ID NO 27
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 27

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Thr Gln Leu Ala Thr Leu Arg Lys Leu Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
                100                 105                 110

Ile Val Thr Cys Ala Met Phe Thr Cys Lys Glu Pro Ile Glu Gly Lys
            115                 120                 125

Val Val Gln Pro Glu Asn Leu Glu Tyr Thr Ile Val Val Thr Pro His
    130                 135                 140

Ser Gly Glu Glu His Ala Val Gly Asn Asp Ala Gly Lys His Gly Val
145                 150                 155                 160

Thr Ala Met Val Thr Pro Gln Ser Ser Ser Val Glu Val Lys Leu Pro
                165                 170                 175

Asp Tyr Gly Glu Val Thr Met Glu Cys Ser Pro Arg Thr Gly Leu Asp
            180                 185                 190

Phe Asn Glu Met Val Leu Leu Thr Met Lys Asn Lys Ala Trp Met Val
    195                 200                 205

His Arg Gln Trp Phe Phe Asp Leu Pro Leu Pro Trp Thr Ser Thr Ala
    210                 215                 220
```

-continued

Asp Thr Gln Gly Pro Asn Trp Ile Gln Lys Glu Thr Leu Val Thr Phe
225                 230                 235                 240

Lys Asn Pro His Ala Lys Lys Gln Asp Val Val Leu Gly Ser Gln
            245                 250                 255

Glu Gly Ala Met His Thr Ala Leu Thr Gly Ala Thr Glu Ile Gln Asn
            260                 265                 270

Ser Gly Gly Thr Ser Ile Phe Ala Gly His Leu Lys Cys Arg Leu Arg
        275                 280                 285

Met Asp Lys Leu Arg Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Asp Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Ile Val Thr Leu Tyr Leu Gly Val Met Val Gln Ala
                485                 490                 495

<210> SEQ ID NO 28
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 28

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Phe Lys Thr
        35                  40                  45

Glu Val Thr Gln Leu Ala Thr Leu Arg Lys Leu Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Pro Ile Glu Gly Lys
        115                 120                 125

Val Val Gln Pro Glu Asn Leu Lys Tyr Thr Ile Ile Val Thr Val His
    130                 135                 140

Ser Gly Glu Glu His Ala Val Gly Asn Asp Ala Thr Glu His Gly Val
145                 150                 155                 160

Thr Ala Met Val Thr Pro Gln Ala Ser Ser Val Glu Val Lys Leu Pro
                165                 170                 175

Asp Tyr Gly Glu Val Thr Met Glu Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Phe Asp Leu Pro Leu Pro Trp Thr Ser Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Thr
            260                 265                 270

Ser Ser Thr Thr Thr Ile Phe Ala Gly His Leu Lys Cys Arg Leu Arg
        275                 280                 285

Met Asp Lys Leu Arg Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Asp Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Ala Val Val Gln Ala
                485                 490                 495

<210> SEQ ID NO 29
<211> LENGTH: 495
<212> TYPE: PRT

<213> ORGANISM: Artificial
<220> FEATURE:
<223> OTHER INFORMATION: Chimeric Dengue virus E glycoprotein sequence

<400> SEQUENCE: 29

```
Met Arg Cys Val Gly Ile Gly Asn Arg Asp Phe Val Glu Gly Leu Ser
1               5                   10                  15

Gly Ala Thr Trp Val Asp Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Ala Thr Gln Leu Ala Thr Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Ile Glu Gly Lys
        115                 120                 125

Val Val Gln Tyr Glu Asn Leu Lys Tyr Ser Val Ile Val Thr Val His
130                 135                 140

Thr Gly Asp Gln His Gln Val Gly Asn Glu Ala Thr Glu His Gly Val
145                 150                 155                 160

Thr Ala Met Ile Thr Pro Gln Ser Pro Ser Val Glu Val Lys Leu Pro
                165                 170                 175

Asp Tyr Gly Glu Leu Thr Leu Asp Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Leu Asp Leu Pro Leu Pro Trp Thr Ser Gly Ala
210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
            260                 265                 270

Ser Gly Gly Thr Ser Ile Phe Ala Gly His Leu Lys Cys Arg Leu Lys
        275                 280                 285

Met Asp Lys Leu Arg Leu Lys Gly Met Ser Tyr Val Met Cys Thr Gly
290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
370                 375                 380

Lys Ala Leu Lys Leu Ser Trp Phe Lys Lys Gly Ser Ser Ile Gly Lys
```

```
                385                 390                 395                 400
Met Phe Glu Ala Thr Ala Arg Gly Ala Arg Arg Met Ala Ile Leu Gly
                    405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
                435                 440                 445

Ser Gly Val Ser Trp Thr Met Lys Ile Gly Ile Gly Ile Leu Leu Thr
            450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                    485                 490                 495
```

<210> SEQ ID NO 30
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 30

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Ala Thr Gln Leu Ala Thr Leu Arg Lys Leu Cys Ile Glu Ala Lys
        50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
                100                 105                 110

Leu Ile Thr Cys Ala Lys Phe Lys Cys Val Thr Lys Ile Glu Gly Lys
            115                 120                 125

Val Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Ile Leu Leu Thr Met Lys Asn Lys Ala Trp Met Val
            195                 200                 205

His Arg Gln Trp Phe Leu Asp Leu Pro Leu Pro Trp Thr Ser Gly Ala
        210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
```

```
            260                 265                 270
Ser Gly Gly Thr Ser Ile Phe Ala Gly His Leu Lys Cys Arg Leu Lys
            275                 280                 285

Met Asp Lys Leu Thr Leu Lys Gly Met Ser Tyr Ser Met Cys Thr Gly
            290                 295             300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Glu Pro
            370                 375             380

Gly Gln Leu Lys Leu Asn Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
            435                 440             445

Ser Gly Val Ser Trp Thr Met Lys Ile Gly Ile Gly Ile Leu Leu Thr
            450                 455             460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 31
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 31

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
                100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
```

```
            130                 135                 140
Thr Gly Asp Gln His Gln Val Gly Asn Glu Ala Thr Glu His Gly Val
145                 150                 155                 160

Thr Ala Met Ile Thr Pro Gln Ser Pro Ser Val Glu Val Lys Leu Pro
                165                 170                 175

Asp Tyr Gly Glu Leu Thr Leu Asp Cys Ser Pro Arg Thr Gly Leu Asp
                180                 185                 190

Phe Asn Glu Met Val Leu Leu Thr Met Glu Lys Lys Ser Trp Leu Val
            195                 200                 205

His Lys Gln Trp Phe Leu Asp Leu Pro Leu Pro Trp Thr Ser Gly Ala
        210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
            275                 280                 285

Met Asp Lys Leu Arg Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
        450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 32
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 32

Met Arg Cys Val Gly Ile Gly Asn Arg Asp Phe Val Glu Gly Leu Ser
```

-continued

```
1               5                   10                  15
Gly Ala Thr Trp Val Asp Val Val Leu Glu His Gly Ser Cys Val Thr
            20                  25                  30
Thr Met Ala Lys Asp Lys Pro Thr Leu Asp Ile Glu Leu Leu Lys Thr
            35                  40                  45
Glu Ala Thr Gln Leu Ala Thr Leu Arg Lys Leu Cys Ile Glu Ala Lys
            50                  55                  60
Ile Ser Asn Thr Thr Thr Asp Ser Arg Cys Pro Thr Gln Gly Glu Ala
65                  70                  75                  80
Thr Leu Val Glu Glu Gln Asp Thr Asn Phe Val Cys Arg Arg Thr Phe
                    85                  90                  95
Val Asp Arg Gly Trp Gly Asn Gly Cys Gly Leu Phe Gly Lys Gly Ser
                    100                 105                 110
Leu Ile Thr Cys Ala Lys Phe Lys Cys Val Thr Lys Ile Glu Gly Lys
                    115                 120                 125
Val Val Gln Tyr Glu Asn Leu Lys Tyr Ser Val Ile Val Thr Val His
                    130                 135                 140
Thr Gly Asp Gln His Gln Val Gly Asn Glu Ala Thr Glu His Gly Val
145                 150                 155                 160
Thr Ala Met Ile Thr Pro Gln Ser Pro Ser Val Glu Val Lys Leu Pro
                    165                 170                 175
Asp Tyr Gly Glu Leu Thr Leu Asp Cys Ser Pro Arg Thr Gly Leu Asp
                    180                 185                 190
Phe Asn Glu Met Ile Leu Leu Thr Met Lys Asn Lys Ala Trp Met Val
                    195                 200                 205
His Arg Gln Trp Phe Leu Asp Leu Pro Leu Pro Trp Thr Ser Gly Ala
                    210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
                    245                 250                 255
Glu Gly Ala Met His Thr Ala Leu Thr Gly Ala Thr Glu Ile Gln Asn
                    260                 265                 270
Ser Gly Gly Thr Ser Ile Phe Ala Gly His Leu Lys Cys Arg Leu Lys
                    275                 280                 285
Met Asp Lys Leu Arg Leu Lys Gly Met Ser Tyr Ser Met Cys Thr Gly
                    290                 295                 300
Lys Phe Lys Ile Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                    325                 330                 335
Phe Glu Ile Thr Asp Leu Glu Lys Arg His Val Leu Gly Arg Leu Ile
                    340                 345                 350
Thr Val Asn Pro Ile Val Thr Glu Lys Asp Ser Pro Val Asn Ile Glu
                    355                 360                 365
Ala Glu Pro Pro Phe Gly Asp Ser Tyr Ile Ile Gly Val Glu Pro
                    370                 375                 380
Gly Gln Leu Lys Leu Asn Trp Phe Lys Lys Gly Ser Ser Ile Gly Lys
385                 390                 395                 400
Met Phe Glu Ala Thr Ala Arg Gly Ala Arg Arg Met Ala Ile Leu Gly
                    405                 410                 415
Asp Thr Ala Trp Asp Phe Gly Ser Ile Gly Gly Val Phe Thr Ser Val
                    420                 425                 430
```

-continued

```
Gly Lys Leu Ile His Gln Ile Phe Gly Thr Ala Tyr Gly Val Leu Phe
        435                 440                 445
Ser Gly Val Ser Trp Thr Met Lys Ile Gly Ile Gly Ile Leu Leu Thr
    450                 455                 460
Trp Leu Gly Leu Asn Ser Arg Ser Thr Ser Leu Ser Met Thr Cys Ile
465                 470                 475                 480
Ala Val Gly Met Val Thr Leu Tyr Leu Gly Val Met Val Gln Ala
                485                 490                 495

<210> SEQ ID NO 33
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 33

Met Arg Cys Val Gly Ile Gly Asn Arg Asp Phe Val Glu Gly Leu Ser
1               5                   10                  15
Gly Ala Thr Trp Val Asp Val Val Leu Glu His Gly Gly Cys Val Thr
            20                  25                  30
Thr Met Ala Lys Asn Lys Pro Thr Leu Asp Ile Glu Leu Phe Lys Thr
        35                  40                  45
Glu Val Thr Gln Leu Ala Thr Leu Arg Lys Leu Cys Ile Glu Gly Lys
    50                  55                  60
Ile Thr Asn Ile Thr Thr Asp Ser Arg Cys Pro Thr Gln Gly Glu Ala
65                  70                  75                  80
Val Leu Pro Glu Glu Gln Asp Gln Asn Tyr Val Cys Lys His Thr Tyr
                85                  90                  95
Val Asp Arg Gly Trp Gly Asn Gly Cys Gly Leu Phe Gly Lys Gly Ser
            100                 105                 110
Leu Val Thr Cys Ala Lys Phe Gln Cys Leu Glu Pro Ile Glu Gly Lys
        115                 120                 125
Val Val Gln Tyr Glu Asn Leu Lys Tyr Ser Val Ile Ile Thr Val His
    130                 135                 140
Thr Gly Asp Gln His Gln Val Gly Asn Glu Ala Thr Glu His Gly Val
145                 150                 155                 160
Thr Ala Met Ile Thr Pro Gln Ser Ser Val Glu Val Lys Leu Pro
                165                 170                 175
Asp Tyr Gly Glu Leu Gly Leu Glu Cys Ser Pro Arg Thr Gly Leu Asp
            180                 185                 190
Phe Asn Glu Met Ile Leu Leu Thr Met Lys Asn Lys Ala Trp Met Val
        195                 200                 205
His Arg Gln Trp Phe Phe Asp Leu Pro Leu Pro Trp Thr Ser Gly Ala
    210                 215                 220
Thr Thr Glu Thr Pro Thr Trp Asn Arg Lys Glu Leu Leu Val Thr Phe
225                 230                 235                 240
Lys Asn Ala His Ala Lys Lys Gln Glu Val Val Val Leu Gly Ser Gln
                245                 250                 255
Glu Gly Ala Met His Thr Ala Leu Thr Gly Ala Thr Glu Ile Gln Asn
            260                 265                 270
Ser Gly Thr Thr Ser Ile Phe Ala Gly His Leu Lys Cys Arg Leu Lys
        275                 280                 285
Met Asp Lys Leu Arg Leu Lys Gly Met Ser Tyr Ala Met Cys Thr Asn
    290                 295                 300
```

```
Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
        355                 360                 365

Ala Glu Pro Pro Phe G

```
Asp Tyr Gly Thr Leu Gly Leu Glu Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Phe Asp Leu Pro Leu Pro Trp Thr Ser Gly Ala
    210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
            275                 280                 285

Met Asp Lys Leu Glu Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
                340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Glu Pro
        370                 375                 380

Gly Gln Leu Lys Leu Asn Trp Tyr Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Val Gly Gly Val Leu Asn Ser Leu
                420                 425                 430

Gly Lys Met Val His Gln Ile Phe Gly Ser Ala Tyr Thr Ala Leu Phe
            435                 440                 445

Ser Gly Val Ser Trp Val Met Lys Ile Gly Ile Gly Val Leu Leu Thr
        450                 455                 460

Trp Ile Gly Leu Asn Ser Lys Asn Thr Ser Met Ser Phe Ser Cys Ile
465                 470                 475                 480

Ala Ile Gly Ile Ile Thr Leu Tyr Leu Gly Ala Val Val Gln Ala
                485                 490                 495

<210> SEQ ID NO 35
<211> LENGTH: 493
<212> TYPE: PRT
<213> ORGANISM: Artificial
<220> FEATURE:
<223> OTHER INFORMATION: Chimeric Dengue virus E glycoprotein sequence

<400> SEQUENCE: 35

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Gln Lys Thr
            35                  40                  45
```

-continued

```
Glu Ala Thr Gln Leu Ala Thr Leu Arg Lys Leu Cys Ile Glu Gly Lys
     50                  55                  60

Ile Thr Asn Ile Thr Thr Asp Ser Arg Cys Pro Thr Gln Gly Glu Ala
 65                  70                  75                  80

Val Leu Pro Glu Gln Asp Gln Asn Tyr Val Cys Lys His Thr Tyr
                 85                  90                  95

Val Asp Arg Gly Trp Gly Asn Gly Cys Gly Leu Phe Gly Lys Gly Ser
                100                 105                 110

Leu Val Thr Cys Ala Lys Phe Gln Cys Leu Glu Pro Ile Glu Gly Lys
                115                 120                 125

Val Val Gln Tyr Glu Asn Leu Lys Tyr Thr Val Ile Ile Thr Val His
             130                 135                 140

Thr Gly Asp Gln His Gln Val Gly Asn Glu Ala Gln Gly Val Thr Ala
145                 150                 155                 160

Met Ile Thr Pro Gln Ser Ser Val Glu Val Lys Leu Pro Asp Tyr
                165                 170                 175

Gly Glu Leu Gly Leu Glu Cys Ser Pro Arg Thr Gly Leu Asp Phe Asn
                180                 185                 190

Glu Met Ile Leu Leu Thr Met Lys Asn Lys Ala Trp Met Val His Arg
            195                 200                 205

Gln Trp Phe Phe Asp Leu Pro Leu Pro Trp Thr Ser Gly Ala Thr Thr
        210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Arg Leu Lys Gly Met Ser Tyr Ser Met Cys Thr Gly Lys Phe
    290                 295                 300

Lys Ile Val Lys Glu Ile Ala Glu Thr Gln His Gly Thr Ile Val Ile
305                 310                 315                 320

Arg Val Gln Tyr Glu Gly Asp Gly Ser Pro Cys Lys Ile Pro Phe Glu
                325                 330                 335

Ile Thr Asp Leu Glu Lys Arg His Val Leu Gly Arg Leu Ile Thr Val
            340                 345                 350

Asn Pro Ile Val Thr Glu Lys Asp Ser Pro Val Asn Ile Glu Ala Glu
        355                 360                 365

Pro Pro Phe Gly Asp Ser Tyr Ile Ile Ile Gly Val Glu Pro Gly Gln
    370                 375                 380

Leu Lys Leu Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Val Met Lys Ile Gly Ile Gly Val Leu Leu Thr Trp Ile
    450                 455                 460
```

-continued

```
Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490
```

<210> SEQ ID NO 36
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 36

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Phe Lys Thr
            35                  40                  45

Glu Val Thr Gln Leu Ala Thr Leu Arg Lys Leu Cys Ile Glu Gly Lys
        50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
                100                 105                 110

Leu Val Thr Cys Ala Lys Phe Gln Cys Leu Glu Pro Ile Glu Gly Lys
            115                 120                 125

Val Val Gln Tyr Glu Asn Leu Lys Tyr Thr Val Ile Val Thr Val His
        130                 135                 140

Thr Gly Asp Gln His Gln Val Gly Asn Glu Ala Thr Glu His Gly Val
145                 150                 155                 160

Thr Ala Met Ile Thr Pro Gln Ser Ser Val Glu Val Lys Leu Pro
                165                 170                 175

Asp Tyr Gly Glu Leu Gly Leu Glu Cys Ser Pro Arg Thr Gly Leu Asp
                180                 185                 190

Phe Asn Glu Met Ile Leu Leu Thr Met Lys Asn Lys Ala Trp Met Val
            195                 200                 205

His Arg Gln Trp Phe Phe Asp Leu Pro Leu Pro Trp Thr Ser Gly Ala
        210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
            275                 280                 285

Met Asp Lys Leu Arg Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335
```

-continued

```
Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Tyr Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Val Gly Gly Val Leu Asn Ser Leu
            420                 425                 430

Gly Lys Met Val His Gln Ile Phe Gly Ser Ala Tyr Thr Ala Leu Phe
        435                 440                 445

Ser Gly Val Ser Trp Val Met Lys Ile Gly Ile Gly Val Leu Leu Thr
    450                 455                 460

Trp Ile Gly Leu Asn Ser Lys Asn Thr Ser Met Ser Phe Ser Cys Ile
465                 470                 475                 480

Ala Ile Gly Ile Ile Thr Leu Tyr Leu Gly Ala Val Val Gln Ala
                485                 490                 495

<210> SEQ ID NO 37
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 37

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Phe Lys Thr
        35                  40                  45

Thr Val Thr Gln Leu Ala Thr Leu Arg Lys Leu Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Pro Ile Glu Gly Lys
        115                 120                 125

Val Val Gln Ile Glu Asn Leu Lys Tyr Thr Val Ile Val Thr Val His
    130                 135                 140

Asn Gly Asp Thr His Ala Val Gly Asn Asp Thr Thr Glu His Gly Thr
145                 150                 155                 160

Thr Ala Thr Ile Thr Pro Arg Ser Pro Thr Ser Glu Ile Gln Leu Thr
                165                 170                 175

Asp Tyr Gly Glu Leu Thr Leu Asp Cys Glu Pro Arg Ser Gly Ile Asp
            180                 185                 190

Phe Asn Glu Met Ile Leu Leu Thr Met Lys Lys Lys Ala Trp Met Val
        195                 200                 205
```

```
His Arg Gln Trp Phe Phe Asp Leu Pro Leu Pro Trp Thr Ser Gly Ala
    210                 215                 220
Asp Thr Ser Glu Val His Trp Asn Tyr Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Ala Gly Ala Thr Glu Ile Gln Asn
            260                 265                 270
Ser Gly Gly Thr Ser Ile Phe Ala Gly His Leu Lys Cys Lys Val Arg
        275                 280                 285
Met Glu Lys Leu Arg Ile Lys Gly Met Ser Tyr Thr Met Cys Ser Gly
    290                 295                 300
Lys Phe Ser Ile Asp Lys Glu Met Ala Glu Thr Gln His Gly Thr Thr
305                 310                 315                 320
Val Val Lys Val Lys Tyr Glu Gly Ala Gly Ala Pro Cys Lys Val Pro
                325                 330                 335
Ile Glu Ile Arg Asp Val Asn Lys Glu Lys Val Val Gly Arg Val Ile
            340                 345                 350
Ser Ser Thr Pro Leu Ala Glu Asn Thr Asn Ser Val Thr Asn Ile Glu
        355                 360                 365
Leu Glu Pro Pro Phe Gly Asp Ser Tyr Ile Val Ile Gly Val Gly Asn
    370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys Arg Met Ala Ile Leu Gly
                405                 410                 415
Glu Thr Ala Trp Asp Phe Gly Ser Val Gly Gly Leu Phe Thr Ser Leu
            420                 425                 430
Gly Lys Ala Val His Gln Val Phe Gly Ser Val Tyr Thr Thr Met Phe
        435                 440                 445
Gly Gly Val Ser Trp Met Ile Arg Ile Leu Ile Gly Phe Leu Val Leu
    450                 455                 460
Trp Ile Gly Thr Asn Ser Arg Asn Thr Ser Met Ala Met Thr Cys Ile
465                 470                 475                 480
Ala Val Gly Gly Ile Thr Leu Phe Leu Gly Phe Thr Val Gln Ala
                485                 490                 495

<210> SEQ ID NO 38
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 38

Met Arg Cys Val Gly Val Gly Asn Arg Asp Phe Val Glu Gly Val Ser
1               5                   10                  15
Gly Gly Ala Trp Val Asp Leu Val Leu Glu His Gly Gly Cys Val Thr
                20                  25                  30
Thr Met Ala Gln Gly Lys Pro Thr Leu Asp Phe Glu Leu Phe Lys Thr
            35                  40                  45
Thr Val Thr Glu Val Ala Leu Leu Arg Thr Tyr Cys Ile Glu Ala Ser
        50                  55                  60
Ile Ser Asn Ile Thr Thr Ala Thr Arg Cys Pro Thr Gln Gly Glu Pro
65                  70                  75                  80
```

```
Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
            115                 120                 125

Leu Val Gln Ile Glu Asn Leu Lys Tyr Thr Val Ile Val Thr Val His
130                 135                 140

Asn Gly Asp Thr His Ala Val Gly Asn Asp Thr Thr Glu His Gly Thr
145                 150                 155                 160

Thr Ala Thr Ile Thr Pro Arg Ser Pro Thr Ser Glu Ile Gln Leu Thr
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Thr Trp Leu Val
        195                 200                 205

His Lys Gln Trp Phe Leu Asp Leu Pro Leu Pro Trp Thr Ala Gly Ala
        210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Val Asp Ser
            260                 265                 270

Gly Gly Thr Thr Thr Met Phe Ala Gly His Leu Lys Cys Lys Val Arg
            275                 280                 285

Met Glu Lys Leu Arg Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
            435                 440                 445

Gly Gly Val Ser Trp Met Ile Arg Ile Leu Ile Gly Phe Leu Val Leu
        450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495
```

```
<210> SEQ ID NO 39
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 39

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Thr Lys Thr
        35                  40                  45

Thr Ala Thr Gln Leu Ala Thr Leu Arg Lys Leu Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Pro Ile Glu Gly Lys
        115                 120                 125

Val Val Gln Ile Glu Asn Leu Glu Tyr Thr Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Leu Thr Met Lys Lys Lys Ala Trp Met Val
        195                 200                 205

His Arg Gln Trp Phe Phe Asp Leu Pro Leu Pro Trp Thr Ser Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Ala Gly Ala Thr Glu Ile Gln Asn
            260                 265                 270

Ser Gly Gly Thr Ser Ile Phe Ala Gly His Leu Lys Cys Lys Val Arg
        275                 280                 285

Met Glu Lys Leu Arg Leu Lys Gly Met Ser Tyr Ser Met Cys Thr Gly
    290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
```

```
                370                 375                 380
Gly Gln Leu Lys Leu Asn Trp Phe Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
                420                 425                 430

Gly Lys Ala Val His Gln Val Phe Gly Ser Val Tyr Thr Thr Met Phe
            435                 440                 445

Gly Gly Val Ser Trp Met Ile Arg Ile Leu Ile Gly Phe Leu Val Leu
            450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
                485                 490                 495

<210> SEQ ID NO 40
<211> LENGTH: 495
<212> TYPE: PRT
<213> ORGANISM: Artificial
<220> FEATURE:
<223> OTHER INFORMATION: Chimeric Dengue virus E glycoprotein sequence

<400> SEQUENCE: 40

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
                20                  25                  30

Thr Met Ala Gln Gly Lys Pro Thr Leu Asp Phe Glu Leu Phe Lys Thr
            35                  40                  45

Thr Val Thr Gln Leu Ala Thr Leu Arg Lys Leu Cys Ile Glu Ala Ser
        50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
                100                 105                 110

Val Val Thr Cys Ala Lys Phe Ser Cys Ser Gly Pro Ile Glu Gly Lys
            115                 120                 125

Val Val Gln Ile Glu Asn Leu Lys Tyr Thr Val Ile Val Thr Val His
        130                 135                 140

Asn Gly Asp Thr His Ala Val Gly Asn Asp Thr Thr Glu His Gly Thr
145                 150                 155                 160

Thr Ala Thr Ile Thr Pro Arg Ser Pro Ser Val Glu Val Lys Leu Thr
                165                 170                 175

Asp Tyr Gly Glu Leu Thr Leu Asp Cys Glu Pro Arg Ser Gly Ile Asp
                180                 185                 190

Phe Asn Glu Met Ile Leu Leu Thr Met Lys Lys Lys Ala Trp Met Val
            195                 200                 205

His Arg Gln Trp Phe Phe Asp Leu Pro Leu Pro Trp Thr Ser Gly Ala
        210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
```

```
                    245                 250                 255
Glu Gly Ala Met His Ser Ala Leu Ala Gly Ala Thr Glu Ile Gln Asn
            260                 265                 270

Ser Gly Gly Thr Ser Ile Phe Ala Gly His Leu Lys Cys Lys Val Arg
        275                 280                 285

Met Glu Lys Leu Arg Leu Lys Gly Met Ser Tyr Ser Met Cys Thr Gly
        290                 295                 300

Lys Phe Lys Ile Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
            325                 330                 335

Phe Glu Ile Thr Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Gly Val Glu Pro
        370                 375                 380

Gly Gln Leu Lys Leu Asn Trp Phe Lys Lys Gly Ser Ser Ile Gly Lys
385                 390                 395                 400

Met Phe Glu Ser Thr Tyr Arg Gly Ala Lys Arg Met Ala Ile Leu Gly
                405                 410                 415

Glu Thr Ala Trp Asp Phe Gly Ser Val Gly Gly Leu Phe Thr Ser Leu
            420                 425                 430

Gly Lys Ala Val His Gln Val Phe Gly Ser Val Tyr Thr Thr Met Phe
        435                 440                 445

Gly Gly Val Ser Trp Met Ile Arg Ile Leu Ile Gly Phe Leu Val Leu
    450                 455                 460

Trp Ile Gly Thr Asn Ser Arg Asn Thr Ser Met Ala Met Thr Cys Ile
465                 470                 475                 480

Ala Val Gly Gly Ile Thr Leu Phe Leu Gly Phe Thr Val Gln Ala
            485                 490                 495
```

METHODS AND COMPOSITIONS FOR RECOMBINANT DENGUE VIRUSES FOR VACCINE AND DIAGNOSTIC DEVELOPMENT

STATEMENT OF PRIORITY

This application is a 35 U.S.C. § 371 national phase application of International Application Serial No. PCT/US2015/058610, filed Nov. 2, 2015, which claims the benefit, under 35U.S.C. § 119(e), of U.S. Provisional Application Ser. No. 62/074,053, filed Nov. 2, 2014, the entire contents of each of which are incorporated by reference herein.

STATEMENT OF GOVERNMENT SUPPORT

This invention was made with government support under Grant Nos. AI 057157, AI 097560, AI 107731 and AI 109761, awarded by the National Institutes of Health. The United States government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-723 ST25.txt, 153,033 bytes in size, generated on May 2, 2017 and filed via EFS-Web, is provided in lieu of a paper copy. This Sequence Listing is incorporated by reference into the specification for its disclosures.

FIELD OF THE INVENTION

The present invention is directed to dengue virus vaccines that induce neutralizing antibodies against more than one dengue virus serotype from a single source.

BACKGROUND OF THE INVENTION

Dengue virus (DENV) is a mosquito-borne flavivirus that is spreading at an unprecedented rate and has developed into a major health and economic burden in over 50 countries. Current DENV vaccines protecting against all four DENV serotypes must be delivered as a "tetravalent" formulation of four viruses or four recombinant proteins, each intended to confer protection against that serotype. The correct mix of serotypes in the tetravalent cocktail to achieve a balanced antibody response is not known, underscored by the recent failure of the most advanced tetravalent live attenuated chimeric virus to provide clinically meaningful protection in a large phase 2B trial in Thailand (Sabchareon et al., 2012). Viral interference is thought to contribute to failure as one or more virus serotypes out-compete the others.

The present invention overcomes previous shortcomings in the art by providing chimeric dengue viruses that induce neutralizing antibodies against more than one dengue virus serotype from a single source.

SUMMARY OF THE INVENTION

In one aspect, the present invention provides a chimeric dengue virus E glycoprotein comprising a dengue virus E glycoprotein backbone that comprises amino acid substitutions that introduce an epitope that is recognized by an antibody that is reactive with a dengue virus serotype that is different from the dengue virus serotype of the dengue virus E glycoprotein backbone, wherein the dengue virus E glycoprotein backbone is from dengue virus serotype 4 and the antibody is reactive with dengue virus serotype 3.

In a further aspect, the present invention provides a chimeric dengue virus E glycoprotein comprising a dengue virus E glycoprotein backbone that comprises amino acid substitutions that introduce a protein domain from a dengue virus serotype that is different from the dengue virus serotype of the dengue virus E glycoprotein backbone, wherein the dengue virus E glycoprotein backbone is from dengue virus serotype 4 and the protein domain is from dengue virus serotype 2.

In another aspect, the present invention provides a chimeric dengue virus E glycoprotein comprising a dengue virus E glycoprotein backbone that comprises amino acid substitutions that introduce an epitope that is recognized by an antibody that is reactive with a dengue virus serotype that is different from the dengue virus serotype of the dengue virus E glycoprotein backbone, wherein the dengue virus E glycoprotein backbone is from dengue virus serotype 2 and the antibody is reactive with dengue virus serotype 1.

Also provided herein is a method of producing an immune response to a dengue virus in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Additionally provided herein is a method of treating a dengue virus infection in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Further provided herein is a method of preventing a disorder associated with dengue virus infection in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

As an additional aspect, the present invention provides a method of protecting a subject from the effects of dengue virus infection, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

In further aspects, the present invention provides methods of identifying the presence of a neutralizing antibody to specific dengue virus serotypes or combinations thereof (e.g., 4/3, 4/2, 2/1) in a biological sample from a subject, comprising: a) administering a composition comprising a particular E glycoprotein this invention to the subject in an amount effective to induce an antibody response to the E glycoprotein; b) contacting a biological sample from the subject with flavivirus particles comprising the particular E glycoprotein above under conditions whereby neutralization of the flavivirus particles can be detected; and c) detecting neutralization in step (b), thereby identifying the presence of a neutralizing antibody to the specific dengue virus serotypes or combinations thereof in the biological sample from the subject.

The present invention additionally provides a method of identifying the presence of a neutralizing antibody to specific dengue virus serotypes or combinations thereof (e.g., 4/3. 4/2, 2/1) in a biological sample from a subject, comprising: a) contacting a biological sample from a subject that has been administered a particular E glycoprotein of this invention with flavivirus particles comprising the E glycoprotein under conditions whereby neutralization of the flavivirus particles can be detected; and b) detecting neutralization in step (a), thereby identifying the presence of a neutralizing antibody to the specific dengue virus serotypes or combinations thereof in the biological sample from the subject.

In other embodiments, the present invention provides a method of identifying an immunogenic composition that induces a neutralizing antibody to specific dengue virus serotypes or combinations thereof (e.g., 4/3, 4/2, 2/1) in a subject, comprising: a) administering an immunogenic composition comprising a particular E glycoprotein of this invention to a subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d) identifying the immunogenic composition as inducing a neutralizing antibody to the specific dengue virus serotypes or combinations thereof in the subject if the biological sample comprises an antibody that neutralizes flavivirus particles comprising the E glycoprotein of (a).

Further provided herein is a method of identifying an immunogenic composition that induces a neutralizing antibody to specific dengue virus serotypes or combinations thereof (e.g., 4/3, 4/2, 2/1) in a subject, the method comprising: a) contacting a biological sample from a subject that has been administered an immunogenic composition comprising a particular E glycoprotein of this invention with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to the specific dengue virus serotypes or combinations thereof in the subject if the biological sample comprises an antibody that neutralizes flavivirus particles comprising the E glycoprotein of (a).

The present invention also provides a method of detecting an antibody to a specific dengue virus serotype or combination thereof in a sample, comprising; a) contacting the sample with a particular E glycoprotein of this invention under conditions whereby an antigen/antibody complex can form; and b) detecting formation of an antigen/antibody complex, thereby detecting an antibody to the specific dengue virus serotype or combination thereof in the sample.

Additionally provided herein is a method of identifying an antibody to a specific dengue virus serotype or combination thereof in a biological sample from a subject, comprising: a) administering a composition comprising a particular E glycoprotein of this invention to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 3 and/or 4 in the biological sample from the subject.

A further aspect of the invention provides a method of identifying an antibody to a specific dengue virus serotype or combinations thereof in a biological sample from a subject, comprising: a) contacting a biological sample from a subject that has been administered an immunogenic composition comprising a particular E glycoprotein of this invention with the E glycoprotein under conditions whereby an antigen/antibody complex can form; and c) detecting formation of an antigen/antibody complex, thereby identifying an antibody dengue virus serotype 3 and/or 4 in the biological sample from the subject.

The present invention additionally provides a method of identifying an immunogenic composition that induces an antibody to a specific dengue virus serotype or combination thereof in a subject, the method comprising: a) contacting a biological sample from a subject that has been administered an immunogenic composition comprising a particular E glycoprotein of this invention with the E glycoprotein under conditions whereby an antigen/antibody complex can form; and b) detecting formation of an antigen/antibody complex, thereby identifying an immunogenic composition that induces an antibody to the specific dengue virus serotype or combination thereof in the subject.

A further embodiment of the invention is a method of identifying an immunogenic composition that induces a neutralizing antibody to a specific dengue virus serotype or combination thereof in a subject, comprising: a) administering an immunogenic composition comprising a particular E glycoprotein to a subject in an amount effective to induce an antibody response to the E glycoprotein; b) contacting a biological sample from the subject with the E glycoprotein of (a) under conditions whereby an antigen/antibody complex can form; and c detecting formation an antigen/antibody complex, thereby identifying an immunogenic composition that induces a neutralizing antibody to the specific dengue virus serotype or combination thereof in the subject.

Additionally provided herein is a dengue virus particle, a flavivirus particle and/or a virus like particle (VLP) comprising the E glycoprotein of this invention.

An isolated nucleic acid molecule encoding the E glycoprotein of this invention is also provided herein, as well as an isolated nucleic acid molecule encoding the dengue virus particle, flavivirus particle or VLP of this invention.

The present invention also provides a composition comprising the E glycoprotein of this invention in a pharmaceutically acceptable carrier and also provides a composition comprising the nucleic acid molecule of this invention, the vector of this invention, the particle of this invention and/or the population of this invention, in a pharmaceutically acceptable carrier.

The present invention further provides the E glycoprotein of this invention, the dengue virus particle of this invention, the flavivirus particle of this invention, the VLP of this invention, the nucleic acid molecule of this invention, the vector of this invention, the population of this invention and/or the composition of this invention, singly or in any combination, for use in the manufacture of a medicament for producing an immune response to a dengue virus in a subject, for treating a dengue virus infection in a subject in need thereof, for preventing a dengue virus infection in a subject and/or for protecting a subject from the effects of dengue virus infection.

Also provided herein is the use of the E glycoprotein of this invention, the dengue virus particle of this invention, the flavivirus particle of this invention, the VLP of this invention, the nucleic acid molecule of this invention, the vector of this invention, the population of this invention and/or the composition of this invention, singly or in any combination, for use in producing an immune response to a dengue virus in a subject, in treating a dengue virus infection in a subject in need thereof, in preventing a dengue virus infection in a subject and/or in protecting a subject from the effects of dengue virus infection.

BRIEF DESCRIPTION OF THE DRAWINGS

FIG. 2. Growth characteristics of rDENV4/3 on mammalian cells. (A) DENV3, DENV4, DENV4 M12, DENV4 M14, and DENV4 M16 were propagated on C6/36 cells until maximal cytopathology was observed (typically 4 days post-inoculation) and harvested for titration on Vero-81 cells. Infectious titers are presented as ffu/ml cell culture supernatant. (B) Infectious foci size and morphology of WT and rDENV viruses on Vero-81 cells.

FIG. 3. Growth characteristics of rDENV4/3 on arthropod cells. (A) Multi-step growth curve analysis of DENV3, DENV4, DENV4 M12, DENV4 M14, and DENV4 M16 inoculated on C6/36 cells at an MOI=0.01. Cell culture supernatants were titrated on C6/36 cells as described. (B) Infectious focus size and morphology of WT and rDENV on C6/36 cells.

FIG. 8. Design of infectious cDNA clones of DENV1 and 2 and generation of recombinant DENV2/1 viruses. (A) Genome schematic of DENV1 and DENV2 infectious clone design including restriction endonucleases used to generate subgenomic fragments. Size of subgenomic fragments indicates positions in DENV genome where breaks were made to circumvent bacterial instability and toxicity. (B) Amino acids changed in DENV2 E protein by transplantation of DENV1 sequences to generate DENV2-1F4E. Amino acid number represents residue from start of E protein of DENV2. (C) Ribbon structure of DENV2 E protein dimer with AA transferred into DENV2-1F4E.

FIG. 13. Design and construction of DV4-EDIII-DV2 virus. (A) Amino acid alignment of DENV2 and DENV4 linear envelope domain III (EDIII) sequence, residues 296-395 of entire E sequence (99 aa total). Residues differing between DENV2 and DENV4 are highlighted grey. Recombinant DENV4 virus containing EDIII from DENV3, rDENV4/2, replaces differing residues from DENV4 with those from DENV2, highlighted in light grey. (B) Cartoon (left) and space filling (right) crystal structure model of DENV2 E protein dimer, with swapped residues colored. (C)

Reverse genetics system for manipulating DENV genome, top=DENV2, bottom=DENV4. DENV genome is divided into four plasmid cassettes which can be individually mutated, ligated together, and electroporated into cells to generate recombinant virus. DENV4-A cassette contains the envelope gene, EDIII is highlighted in grey. Replacing EDIII residues with those from DENV2, in DENV4 backbone creates DV4-EDIII-DV2 virus.

Figure 14:
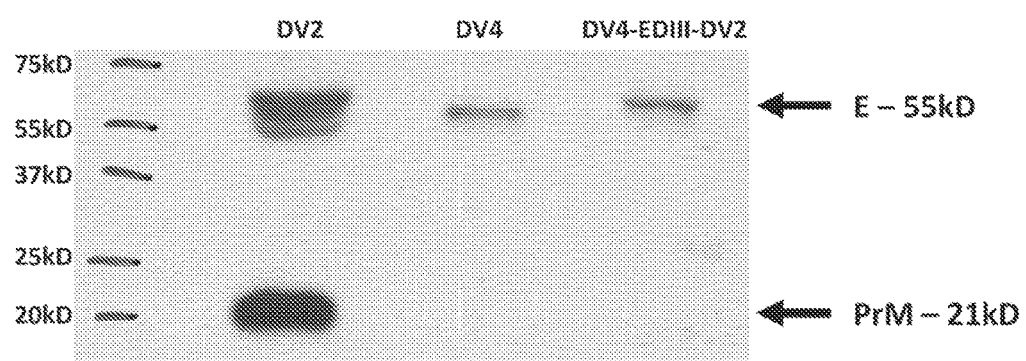

FIG. 14. DENV4 and DV4-EDIII-DV2 virions have similar maturation profiles. Viruses were grown in C6/C36 cells, culture supernatant was collected and centrifuged to remove any cellular debris. Samples were run on 12% SDS-PAGE gel and blots were probed with anti-E (4G2) and anti-PrM (2H12 and 5L20) antibodies. DENV2 has substantial levels of PrM present, indicating either incomplete Furin processing or PrM dissociation. PrM bands are not detectable in either DENV4 or DV4-EDIII-DV2 samples.

Figure 15:
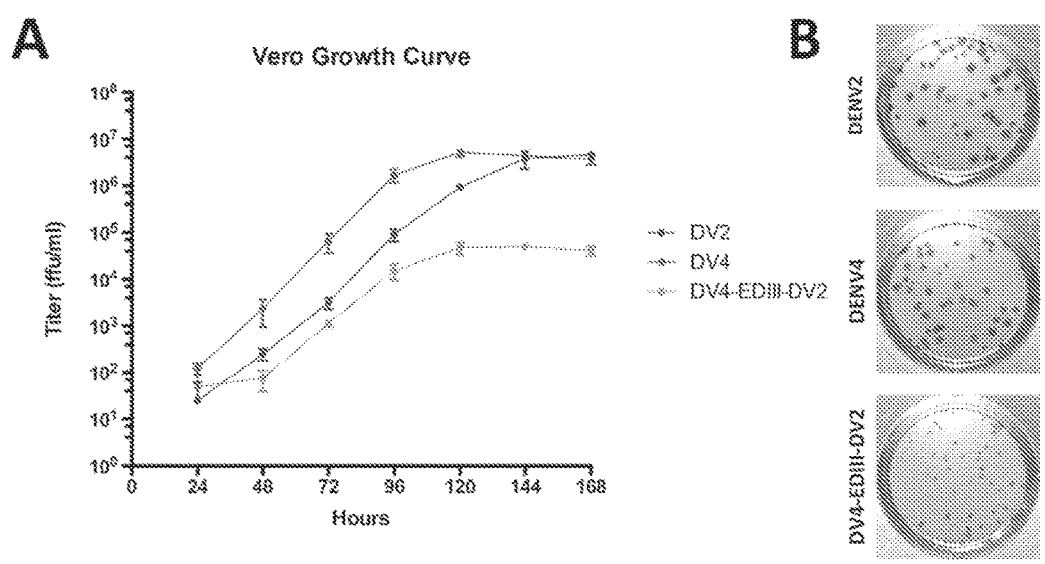

FIG. 15. DV4-EDIII-DV2 has 2 log growth attenuation in Vero cells relative to parental viruses. (A) Vero-81 cells were infected at an MOI=0.01. Viral supernatants were collected every 24 hours and subsequently titered on Vero-81 cells. (B) DENV forms infectious foci in Vero-81 cells (DENV2, DENV4 and DV4-EDIII-DV2 fixed 5, 4 and 6 days post-infection, respectively). DV4-EDIII-DV2 foci are smaller than both parental viruses.

Figure 16:
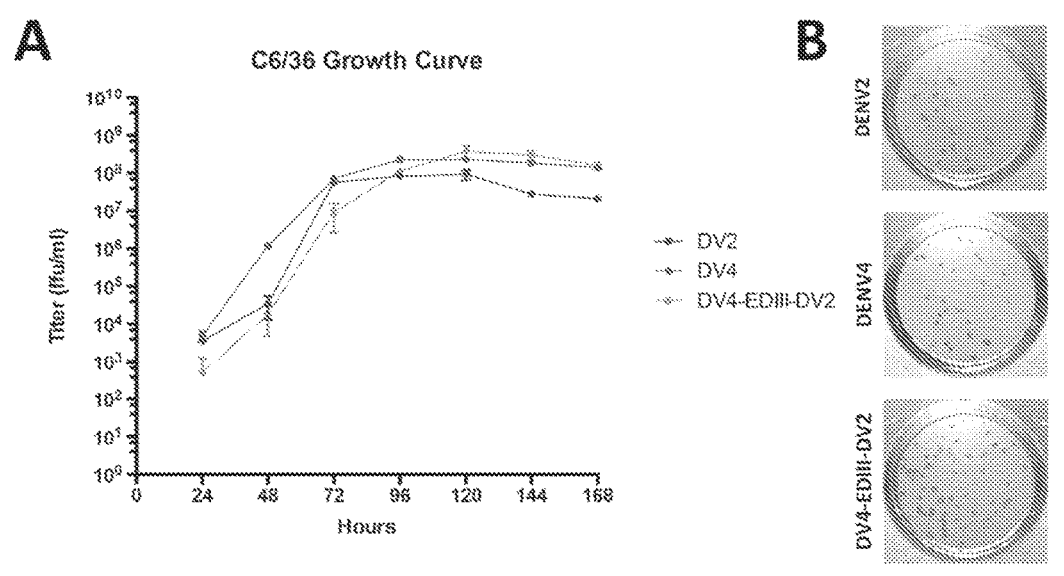

FIG. 16. DV4-EDIII-DV2 has no growth attenuation in C6/C36 cells. (A) C6/C36 cells were infected at an MOI=0.01. Viral supernatants were collected every 24 hours and subsequently titered on C6/C36 cells. (B) DENV forms infectious foci in C6/C36 cells (DENV2, DENV4 and DV4-EDIII-DV2 fixed 4, 3 and 5 days post-infection, respectively). With additional day(s) of growth, DV4-EDIII-DV2 foci reach sizes comparable to parental viruses.

Figure 17:
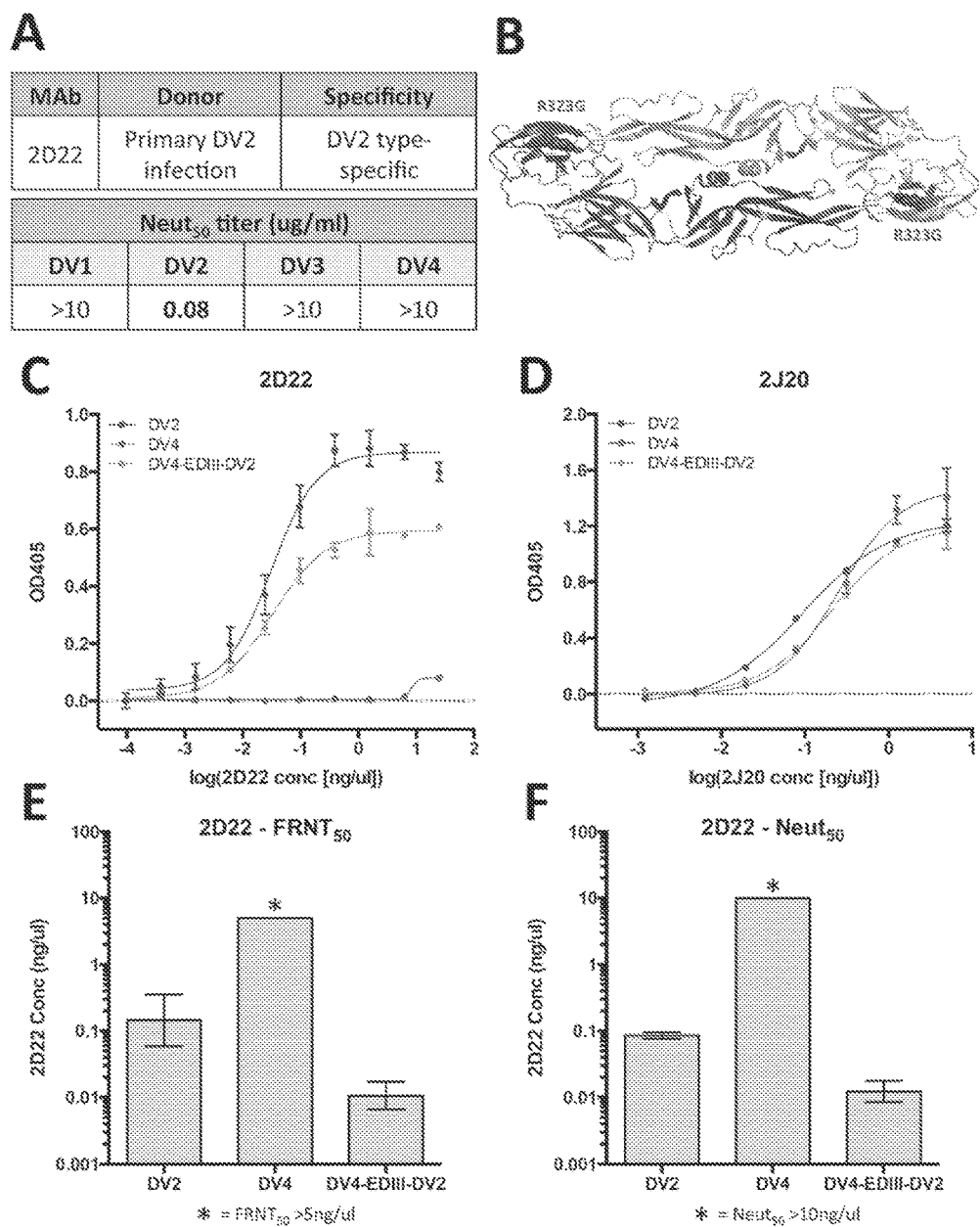

FIG. 17. Transfer of binding and neutralization of DV4-EDIII-DV2 by type-specific DENV2 human MAb. (A) Summary table of human MAb 2D22, a strongly neutralizing DV2 MAb that binds to a quaternary epitope. (B) Previously generated 2D22 escape mutant resulted in one escape mutation, R323G, mapping to EDIII. (C) ELISA assay shows transferred partial binding of 2D22 to DV4-EDIII-DV2, above levels of parental DV4 but not to DV2 levels. (D) ELISA binding of cross-reactive control antibody, 2J20, shows comparable levels of virus present and maintained virus structural integrity. (E) Vero-81 based Focus Reduction Neutralization Test (FRNT) was performed using 2D22 and $FRNT_{50}$ (concentration of antibody required to neutralize 50% of infection) values were calculated. (F) U937+DC-SIGN based neutralization assay (Neut) was performed using 2D22 and $Neut_{50}$ values were calculated. In both assays (E, F), DV4-EDIII-DV2 gained neutralization to 2D22 to levels higher than DV2. DV4 was not neutralized with the maximum concentration of 2D22 in either assay.

Figure 18:
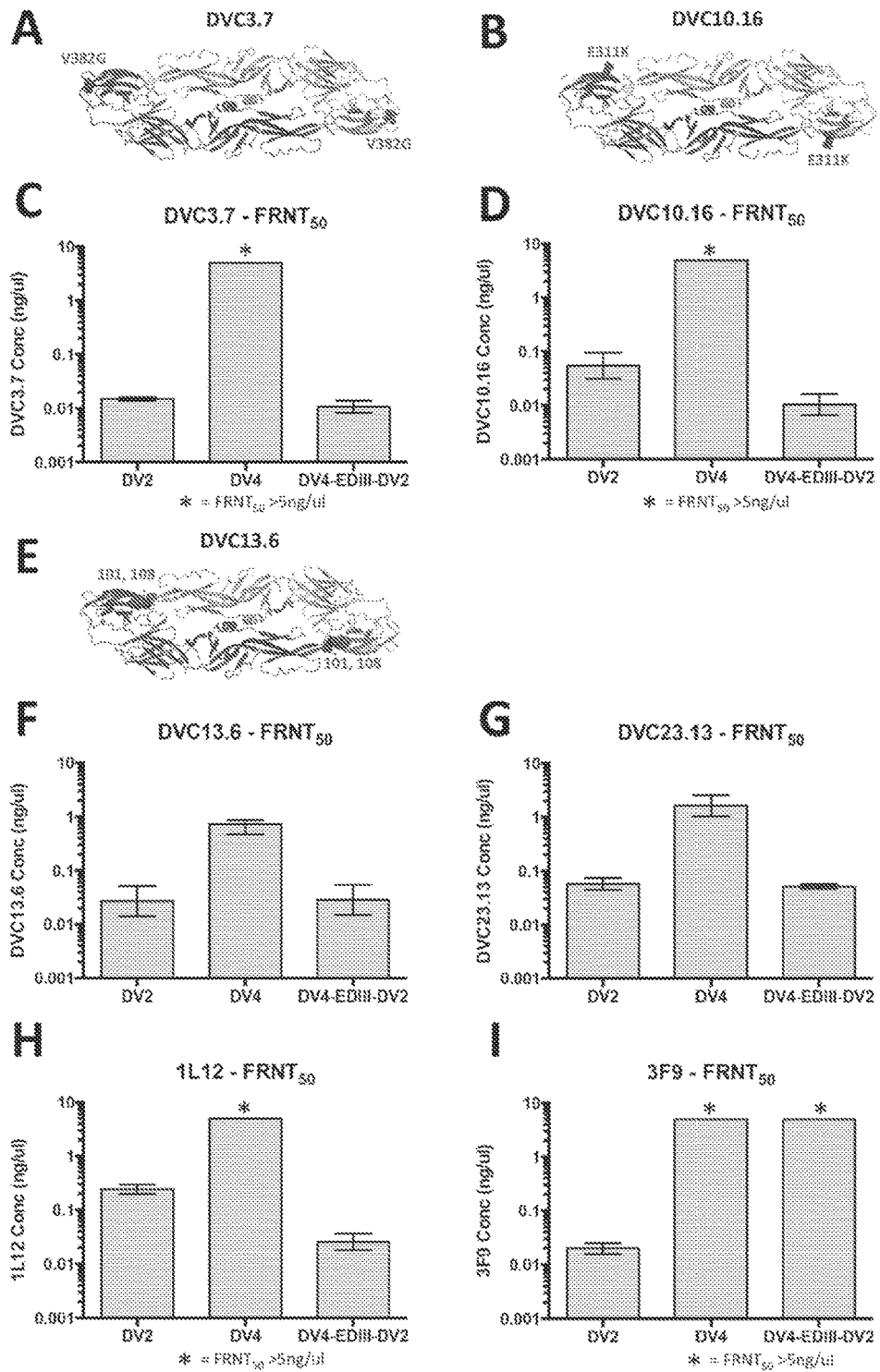

FIG. 18. DV4-EDIII-DV2 gained neutralization to many additional DV2 type-specific MAbs. (A, B, E) DENV E protein dimer crystal structure with escape mutant or scanning alanine mutation residues (from Table 2) are indicated residue 382 for DVC3.7, residue 311 for DVC10.16, and residues 101 and 108 for DVC13.6 respectively. (C, D, F-I) Vero-81 FRNT assay for each MAb. With the exception of 3F9, DV4-EDIII-DV2 neutralization to the given MAbs was transferred to levels equal to or higher than that of the parental DV2 virus. 3F9 does not bind DV4-EDIII-DV2 (ELISA binding data not shown).

Figure 19:
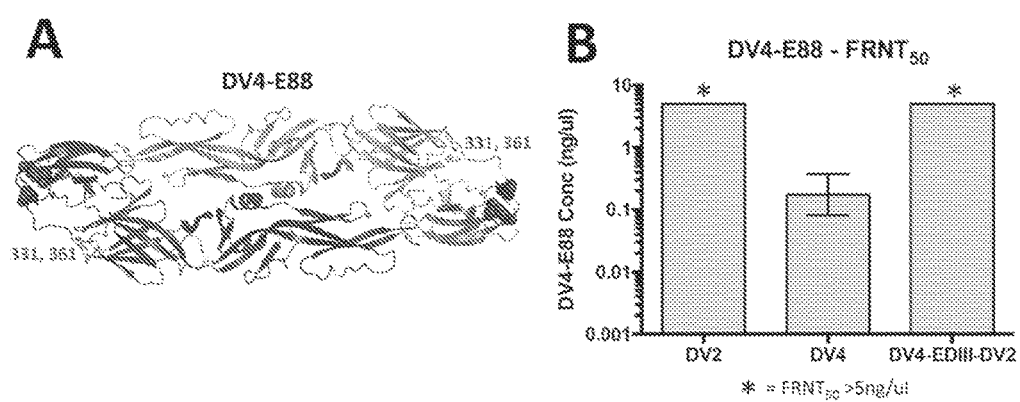

FIG. 19. DV4-EDIII-DV2 is not neutralized by a DV4 type-specific EDIII MAb. (A) DENV E protein dimer crystal structure with scanning alanine mutation residues (from Table 2) indicated at residues 331 and 361. (B) Vero-81 FRNT assay shows DV-E88 is not capable of neutralizing DV4-EDIII-DV2 or DV2, but can neutralize the parental DV4.

Figure 20:
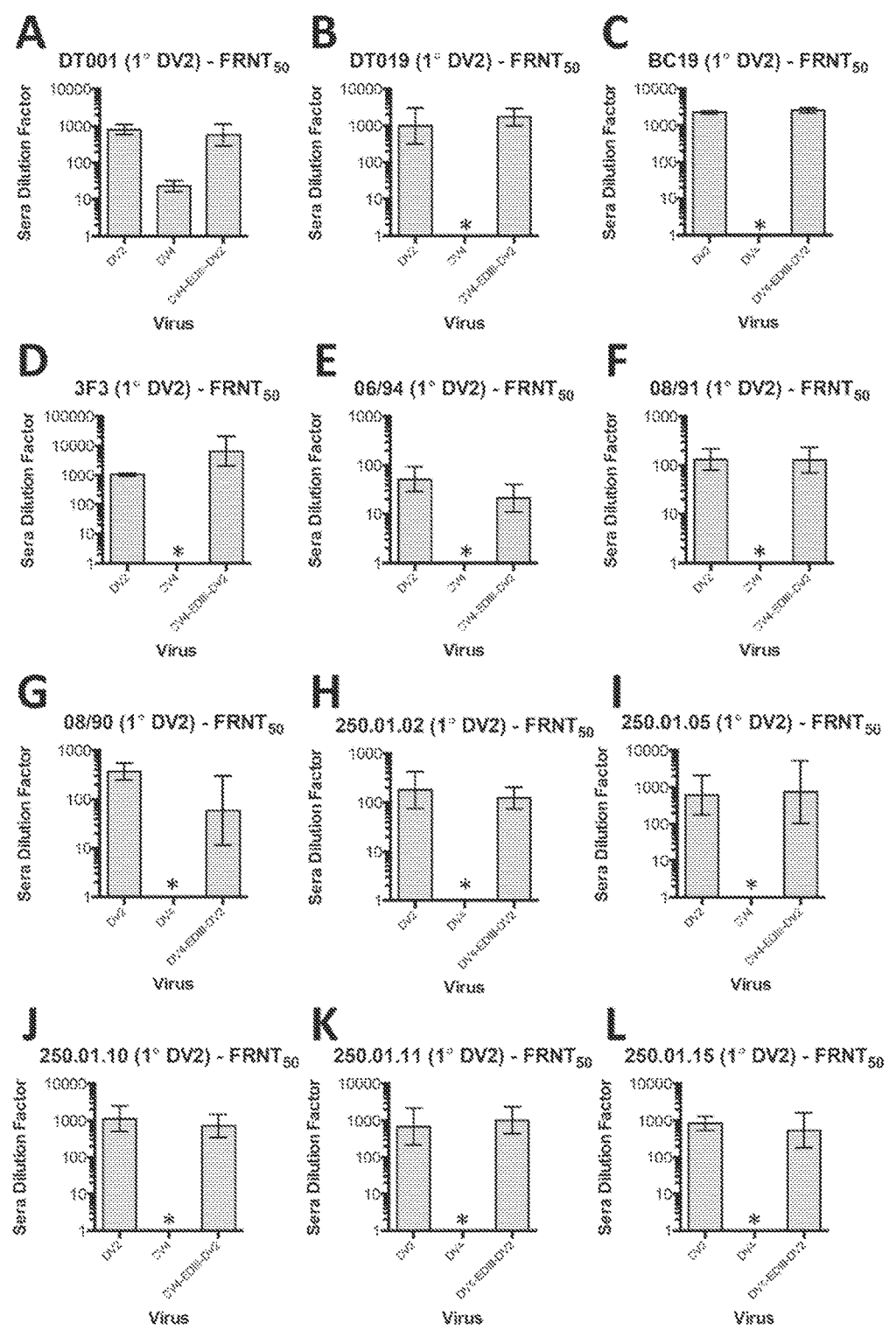

FIG. 20. DV4-EDIII-DV2 gained neutralization to polyclonal DENV2 immune sera. (A-L) Vero-81 FRNT assay shows gain of polyclonal immune sera neutralization to DV4-EDIII-DV2, comparable to levels of DV2 neutralization, indicating transfer of EDIII from DV2 into DV4 is sufficient to transfer majority of DENV2 neutralization. *=$FNRT_{50}<20$ FIG. 21. DV$-EDIII-DV2 maintained neutralization to polyclonal DENV4 immune sera. (A-F) Vero-81 FRNT assay shows DV4-EDIII-DV2 maintains majority neutralization, indicating transfer of EDIII from DV2 does not disrupt the DV4 neutralizing epitope. *=$FNRT_{50}<20$ FIG. 22. DV4-EDIII-DV2 gains DV2 sera neutralization and preserves DV4 sera neutralization. (A) Summary of DV2 polyclonal neutralization data presented in FIG. 19. (B) Summary of DV4 polyclonal neutralization data presented in FIG. 20. Samples with $FNRT_{50}<20$ graphed at sera dilution factor of 19.

Figure 23:
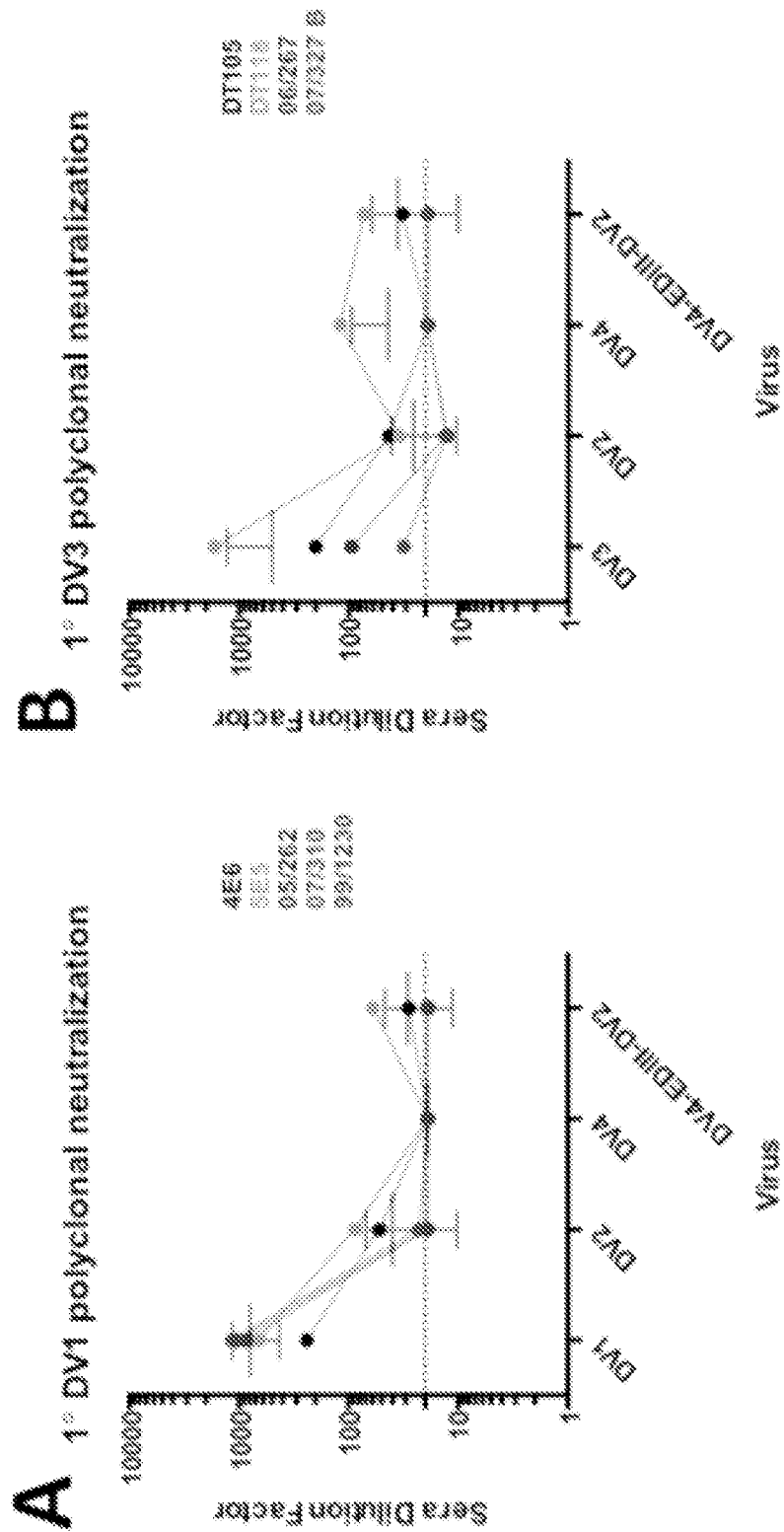

FIG. 23. DV4-EDIII-DV2 does not gain neutralization to heterotypic polyclonal immune sera. Vero-81 FRNT assay shows no gain of neutralization to heterotypic (A) DENV1 or (B) DENV3 polyclonal immune sera above either parental DV2 or DV4 neutralization titers. Samples with $FNRT_{50}<20$ graphed at sera dilution factor of 19.

Figure 24:
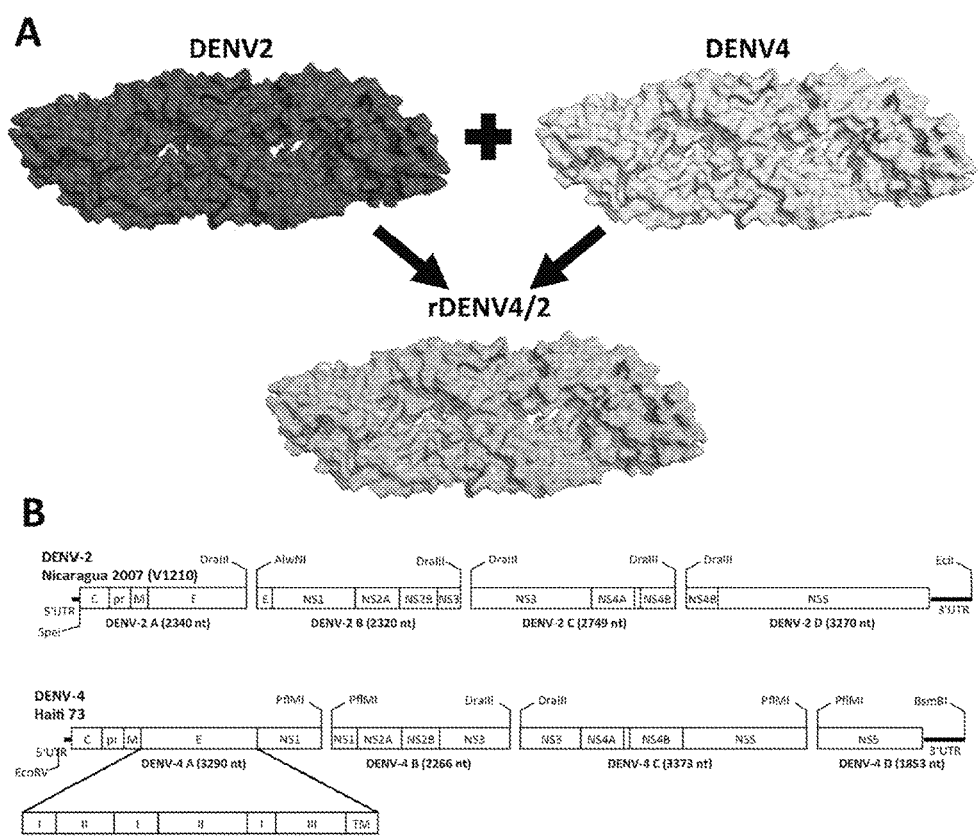

FIG. 24. Design and construction of rDENV4/2 virus. (A) Residues from DENV2 (right) can be moved into DENV4 backbone, generating a recombinant DENV 4/2 virus (rDENV4/2). (B) Reverse genetics system for manipulating the DENV genome. Top=DENV2, bottom=DENV4. The DENV genome is divided into four plasmid cassettes which can be individually mutated, ligated together, and electroporated into cells to generate recombinant virus. The DENV4-A cassette contains the envelope gene where mutations are made. Replacing the DENV4 residues with those from DENV 2 creates an rDENV4/2 virus, built entirely on the DENV4 genetic backbone.

Figure 25:
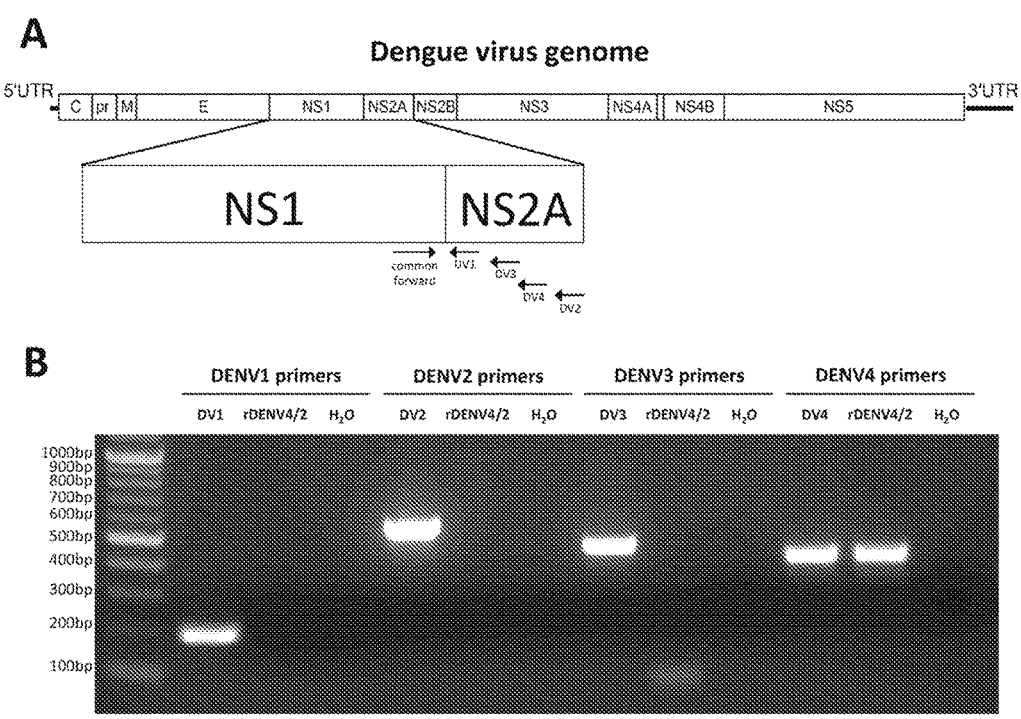

FIG. 25. A new method for serotype identification by RT-PCR and confirmation of DENV4 backbone recombinant virus. (A) Design of RT-PCT primers for serotype-specific RT-PCR. Primers utilize a common sense oligonucleotide targeting the highly conserved 3' end NS1 gene. Serotype-specific antisense primers target the highly divergent NS2A gene. (B) Viruses were grown in C6/36 cells, culture supernatant was collected and centrifuged to remove any cellular debris. Viral RNA was isolated using QIAGEN QIAmp Viral RNA Miniprep Kit. PCR was run for 35 cycles, and PCR product was analyzed on a 1.5% Ultrapure agarose gel. Control RNA (DV1/DV2/DV3/DV4) and water are run as positive and negative controls. Expected product sizes: DV1=205 bp, DV2=539 bp, DV3=455 bp, DV4=401 bp.

Figure 26:
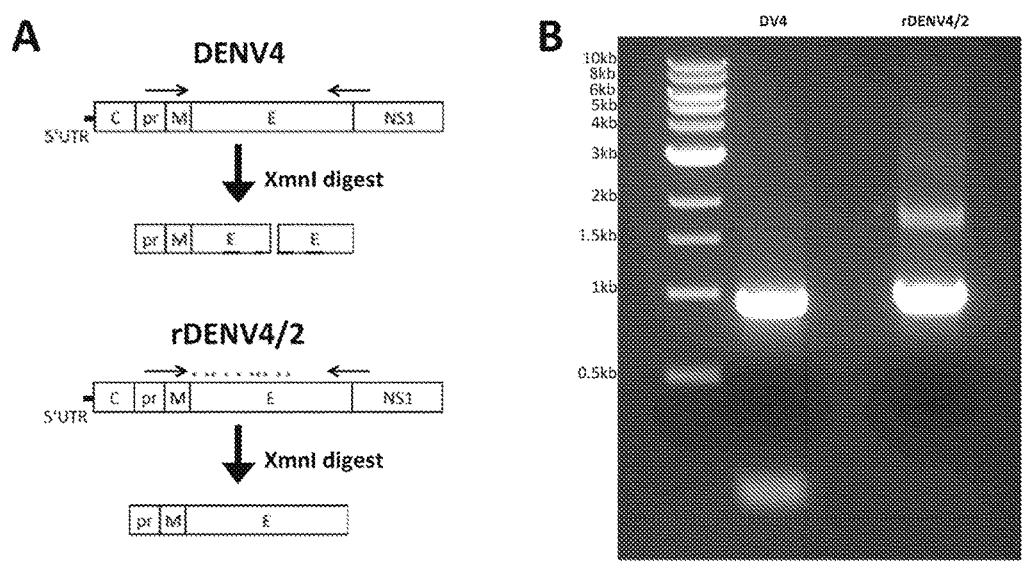

FIG. 26. Restriction fragment length polymorphism distinguishes rDENV4/2 from parental DENV4. (A) Restriction fragment length polymorphism (RFLP) designed to distinguish rDENV4/2 (bottom) from parental DENV4 (top). Mutations (represented as asterisks) introduced into the DENV4 E genome to generate rDENV4/2 disrupt an XmnI restriction enzyme site present in DENV4. (B) PCR products are gel purified and digested with XmnI. Digest products were analyzed on a 1.5% Ultrapure agarose gel. Expected product sizes: full length undigested=1031 bp, digested products=931 bp and 113 bp.

Figure 27:
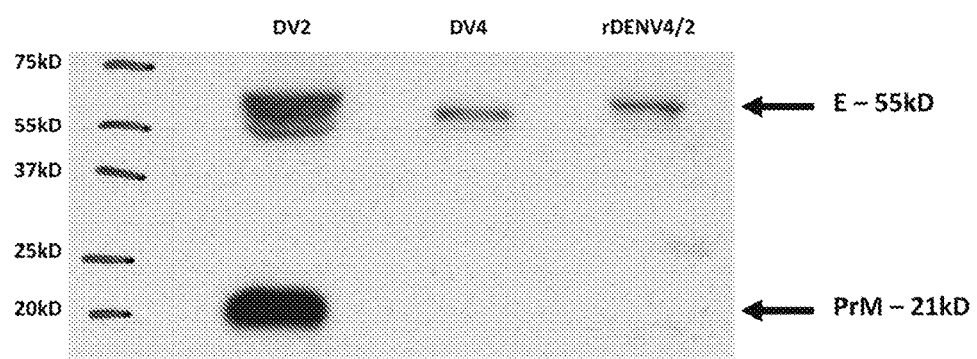

FIG. 27. DENV4 and rDENV4/2 virions have similar maturation profiles. Viruses grown in C6/36 cells, culture supernatant was collected and centrifuged to remove any cellular debris. Samples were run on a 12% SDS-PAGE gel and blots were probed with anti-E (4G2) and anti-PrM (2H12 and 5L20) antibodies. DENV2 has substantial levels of PrM present, indicating either incomplete Furin processing or PrM dissociation. PrM bands are not detected in either DENV4 or rDENV4/2 samples.

Figure 28:
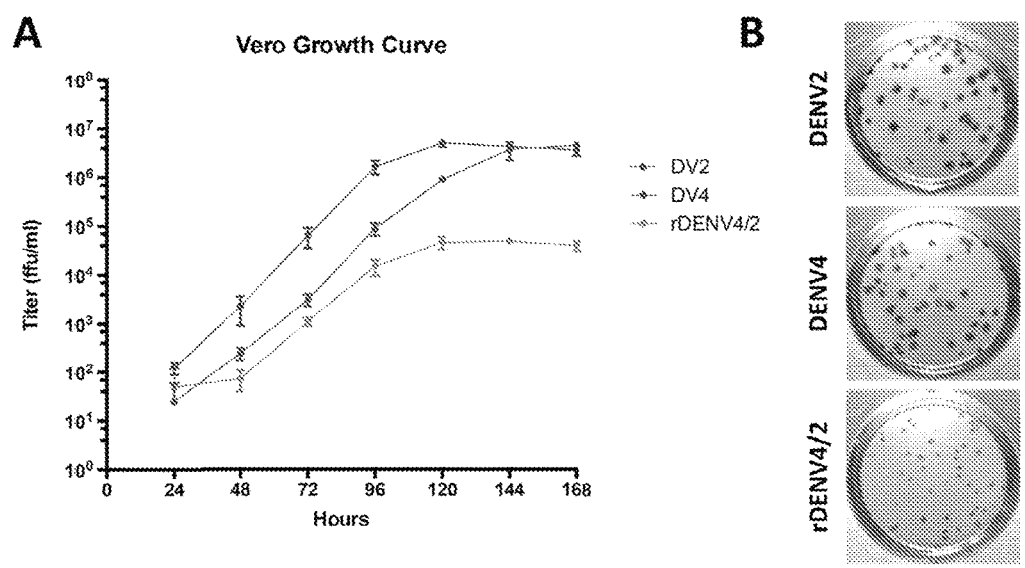

FIG. 28. rDENV4/2 has a 2 log growth attenuation in Vero cells relative to parental viruses. (A) Vero-81 cells were infected at an MOI=0.01. Viral supernatants were collected every 24 hrs. and subsequently titered on Vero-81 cells. (B) DENV forms infectious foci in Vero-81 cells (DENV2, DENV4, and rDENV4/2 fixed 5, 4, and 6 days post-infection, respectively). rDENV4/2 foci are smaller than both parental viruses.

Figure 29:
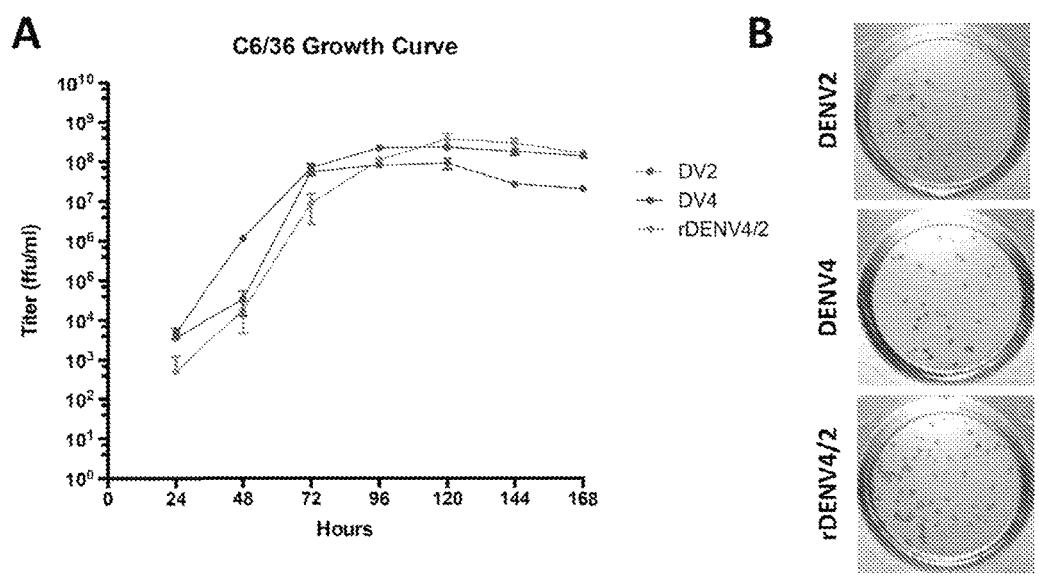

FIG. 29. rDENV4/2 has no growth attenuation in C6/36 cells and forms similar infectious foci relative to parental viruses. (A) C6/36 cells were infected at an MOI=0.01. Viral supernatants were collected every 24 hrs. and subsequently titered on C6/36 cells. (B) DENV forms infectious foci on C6/36 cells (DENV2, DEVN4, and rDENV4/2 fixed 4, 3, and 5 days post-infection, respectively). With additional day(s) of growth, rDENV4/2 foci reach sizes comparable with parental viruses.

Figure 30:
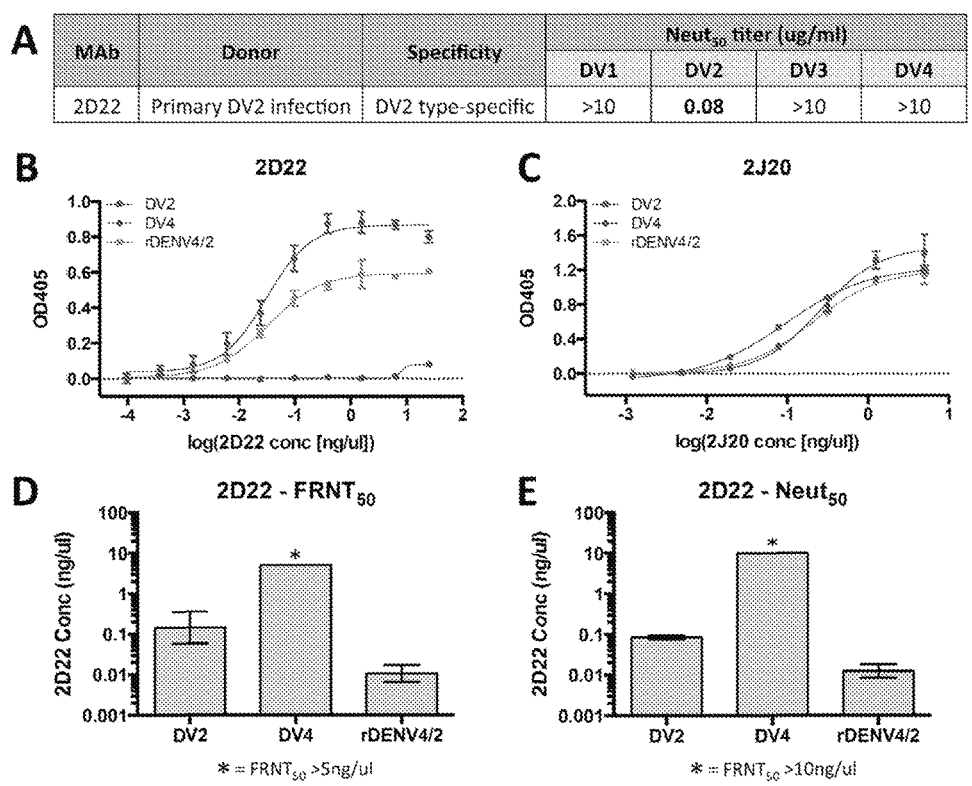

FIG. 30. Transfer of binding and neutralization of rDENV4/2 by type-specific DENV2 human MAb. (A) Summary table of human MAb 2D22, a strongly neutralizing DV2 MAb that binds to a quaternary epitope. (B) ELISA assay shows transferred partial binding of 2D22 to rDENV4/2, above levels of parental DV4 but not to DV2 levels. (C) ELISA binding of cross-reactive control antibody, 2J20, shows comparable levels of virus present and maintained virus integrity. (D) Vero-81 based Focus Reduction Neutralization Test (FRNT) was performed using 2D22 and FRNT$_{50}$ (concentration of antibody required to neutralize 50% of infection) values were calculated. (E) U937+DC-SIGN based neutralization assay (Neut) was performed using 2D22 and Neut$_{50}$ values were calculated. In both assays (E, F) rDENV4/2 gained neutralization to 2D22 to levels higher than DV2. DV4 was not neutralized with the maximum concentration of 2D22 in either assay.

Figure 31:
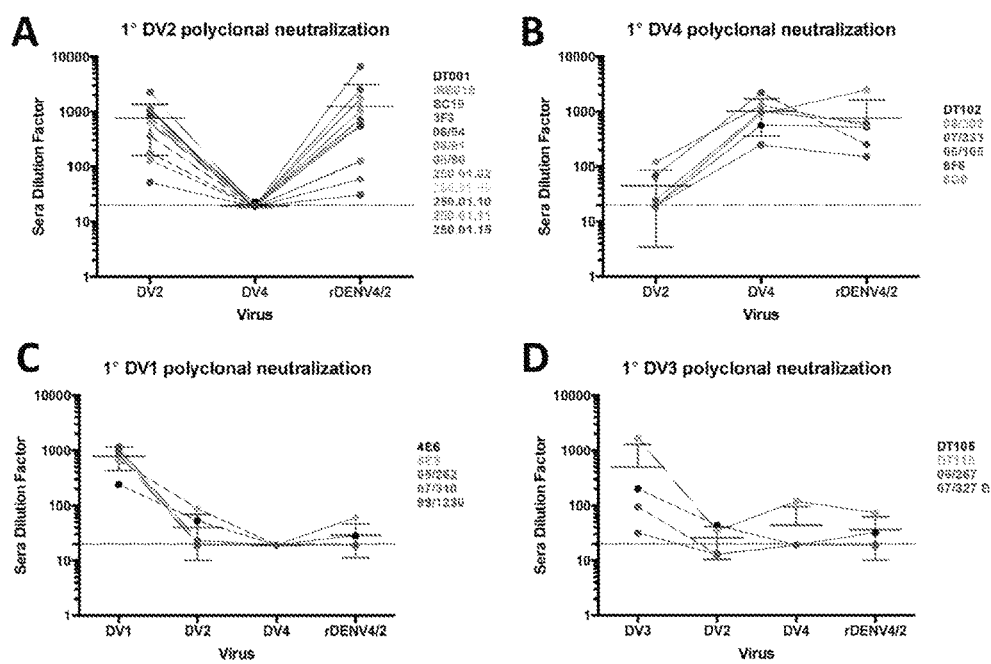

FIG. 31. rDENV4/2 gains neutralization to DENV2 polyclonal immune sera while preserving neutralization to DENV4 polyclonal sera. Vero-81 FRNT assay shows rDENV4/2 (A) gains neutralization to DENV2 polyclonal immune sera to levels comparable to parental DENV2. (B) rDENV4/2 shows no loss to neutralization by DENV4 polyclonal immune sera. rDENV4/2 shows no gain of neutralization to heterotypic (C) DENV1 and (D) DENV3 polyclonal immune sera above either parental DENV 2 or DENV4 neutralization titers. Sera from individuals with either nature infection, or experimental vaccination are coded as indicated. Samples with FRNT$_{50}$<20 graphed at sera dilution factor of 19.

FIG. 32A. Alignment of recombinant DENV4/2 sequences. The amino acid sequences of wild-type DENV2, recombinant DV4-EDIII-DV2 and wild-type DENV4 are shown, along with a consensus sequence and amino acid conservation percentage.

Figure 32B:
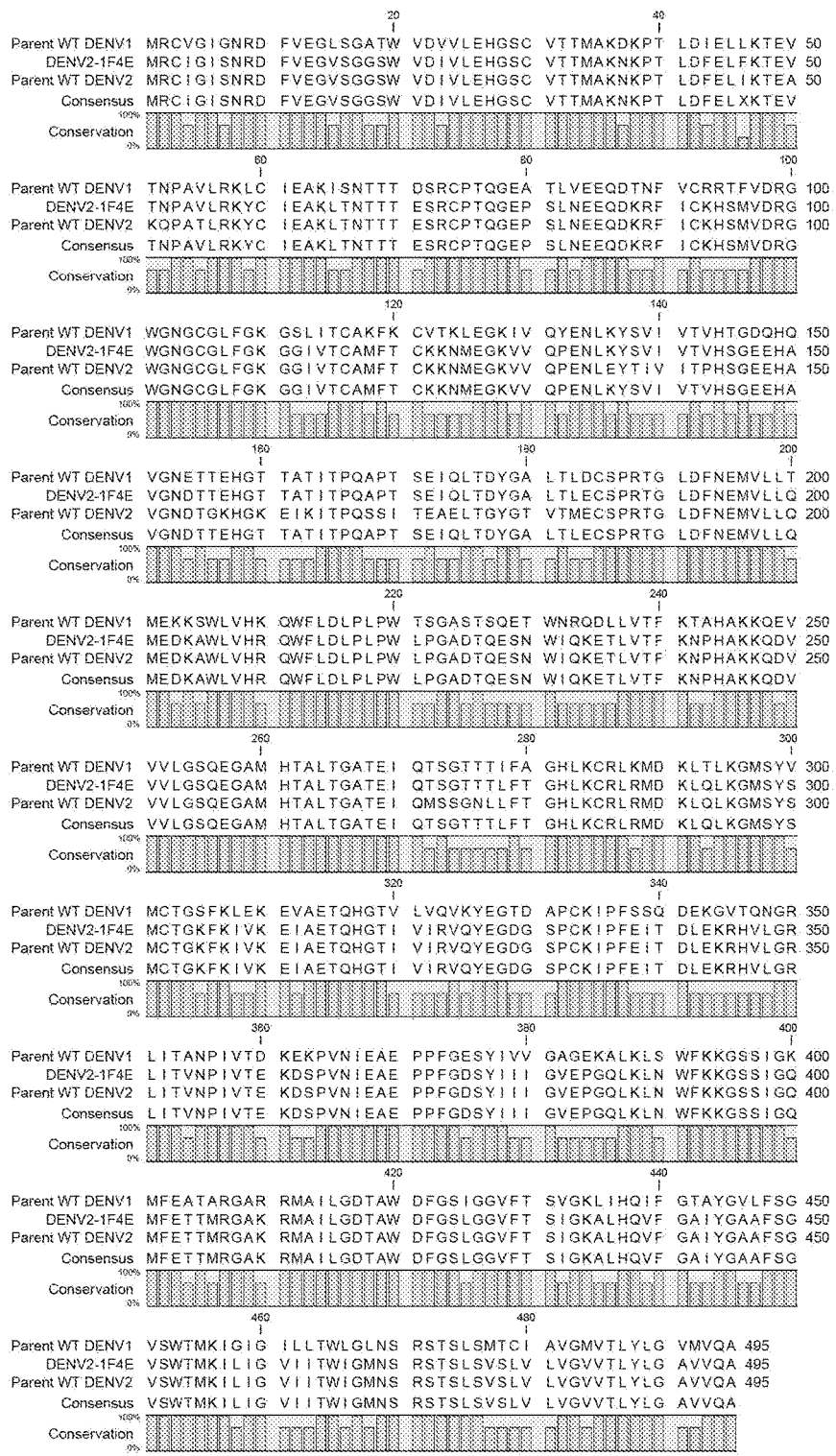

FIG. 32B. Alignment of recombinant DENV2/1 sequences. The amino acid sequences of wild-type DENV1, recombinant DENV2-1F4E and wild-type DENV2 are shown, along with a consensus sequence and amino acid conservation percentage.

Figure 32C:
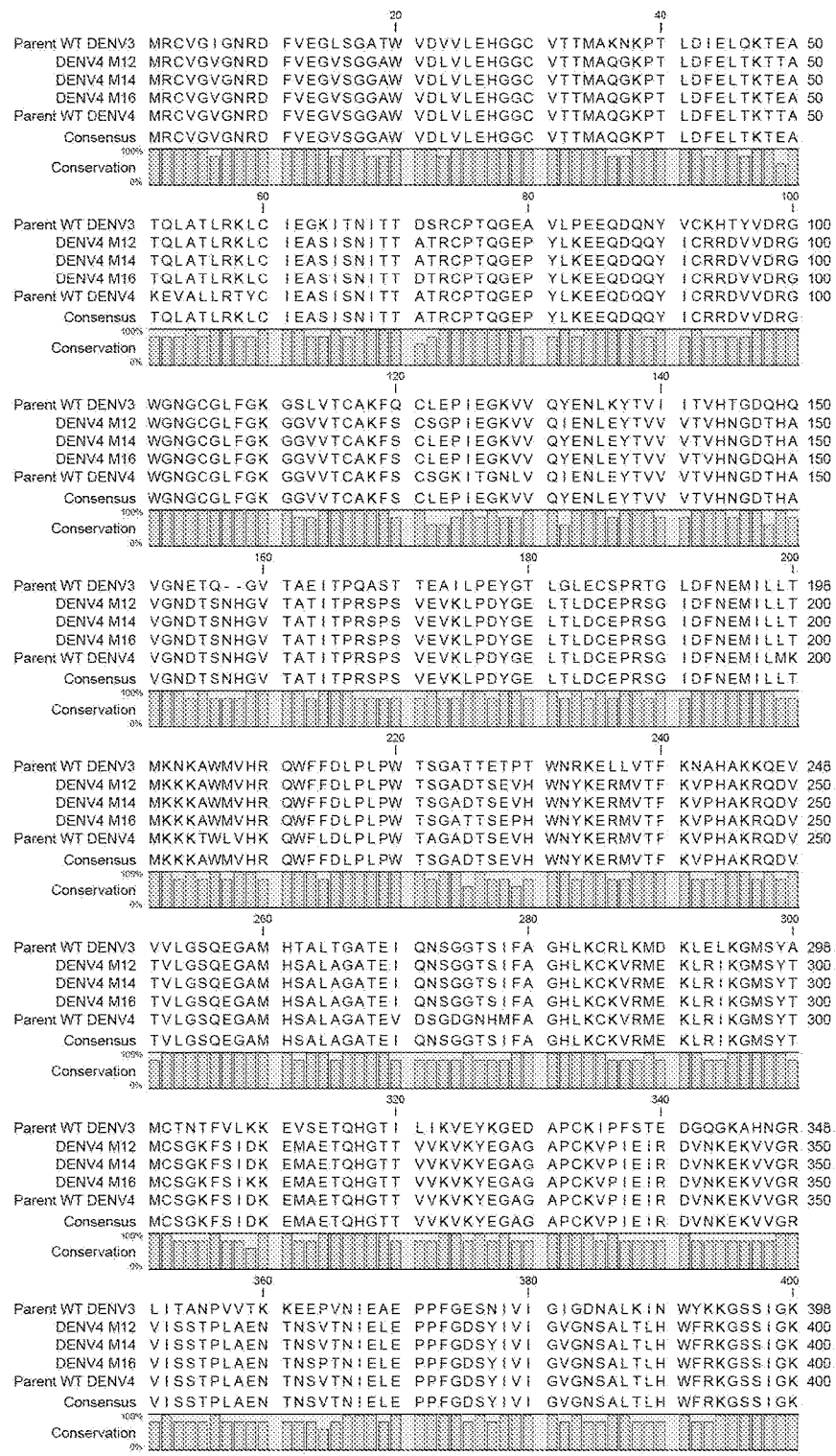
Figure 32C:
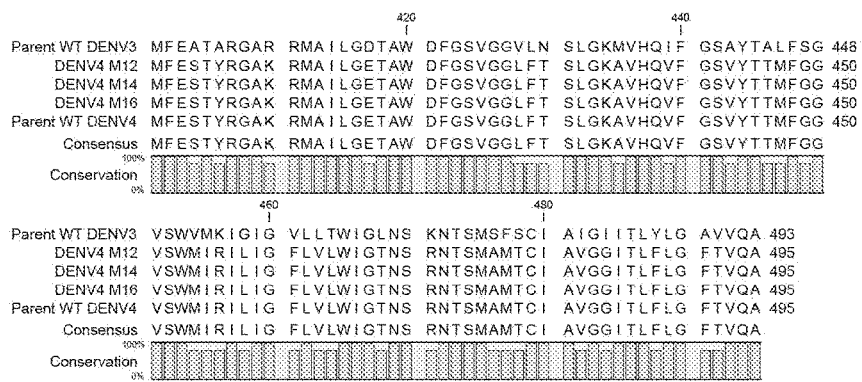

FIG. 32C. Alignment of recombinant DENV4/3 sequences. The amino acid sequences of wild-type DENV3, recombinant DENV4 M12, DENV4 M14, DENV4 M16 and wild-type DENV4 are shown, along with a consensus sequence and amino acid conservation percentage.

DETAILED DESCRIPTION OF THE INVENTION

The present invention is based on the unexpected discovery that one or more epitope regions that define one or more DENV serotypes can be transferred into a protein backbone of a different DENV serotype to create a chimeric molecule that contains antibody targets for multiple serotypes, thereby functioning as a multivalent (e.g., bivalent, trivalent or tetravalent) vaccine that can induce neutralizing antibodies against two, three or four different DENV serotypes from a single source or fewer than four sources. Thus, the present invention provides a platform for construction of a chimeric dengue virus E glycoprotein backbone that comprises amino acid substitutions that introduce one or more epitopes that are recognized by respective antibodies that are reactive with one or more than one dengue virus serotype that is different from the dengue virus serotype of the dengue virus E glycoprotein backbone.

In some embodiments, that dengue virus E glycoprotein backbone is from dengue virus serotype 1. In some embodiments, the dengue virus E glycoprotein backbone can be from dengue virus serotype 2, dengue virus serotype 3 or dengue virus serotype 4.

In some embodiments, the antibody that is reactive with a dengue virus serotype that is different from the dengue virus serotype of the dengue virus E glycoprotein backbone is an antibody that is reactive with dengue virus serotype 1, dengue virus serotype 2, dengue virus type 3 or dengue virus serotype 4.

In some embodiments, one or more dengue virus protein domains from one or more respective dengue virus serotypes can be introduced into a dengue virus E glycoprotein backbone of a different dengue virus serotype.

It would be understood that any combination of a first dengue virus serotype for the dengue virus E glycoprotein backbone and a dengue virus epitope or dengue virus protein domain as identified in a second, third and/or fourth dengue virus serotype, respectively, can be used, provided that the first dengue virus serotype and the second, third and/or fourth dengue virus serotype are different (i.e., the second, third and/or fourth serotypes are not the same serotype as the first dengue virus serotype and/or the second, third and/or fourth dengue virus serotypes are different from one another).

Thus, in some embodiments, the present invention provides a chimeric dengue virus E glycoprotein comprising a dengue virus E glycoprotein backbone that comprises amino acid substitutions that introduce an epitope that is recognized by an antibody that is reactive with a dengue virus serotype that is different from the dengue virus serotype of the dengue virus E glycoprotein backbone, wherein the dengue virus E glycoprotein backbone is from dengue virus serotype 4 and the antibody is reactive with dengue virus serotype 3. In some embodiments, the antibody is monoclonal antibody 5J7 and in some embodiments, the E glycoprotein can comprise, consist essentially of, or consist of the amino acid sequence:

(WT_DENV4, SEQ ID NO: 1)
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA, wherein said amino acid sequence comprises all or less than all in any combination, of the following amino acid substitutions:
T49E, K51T, E52Q, V53L, L55T, T58K, Y59L, S122L, G123E, K124P, T126E, N128K, L129V, I132Y, M199L, K200T, T205A, L207M, K210R, L214F, A222S, V270I, D271Q, S272N, G273S, D274G, N276T, H277S and M278I, and wherein said amino acid sequence can further comprise one or more of the following amino acid substitutions in any combination: A71D, T148Q, D225T, V229P, D307K, K321Q and V362P.

In some embodiments, the chimeric dengue virus E glycoprotein described above as a 4/3 dengue virus glycoprotein can comprise, consist essentially of or consist of the amino acid sequence:

(DENV4_M12, SEQ ID NO: 2)
MRCVGVGNRDFVEGVSGGAWVDLVLEHGGCVTTMAQGKPTLDFELTKTTA

TQLATLRKLCIEASISNITTATRCPTQGEPYLKEEQDQQYICRRDVVDRG

WGNGCGLFGKGGVVTCAKFSCSGPIEGKVVQIENLEYTVVVTVHNGDTHA

VGNDTSNHGVTATITPRSPSVEVKLPDYGELTLDCEPRSGIDFNEMILLT

MKKKAWMVHRQWFFDLPLPWTSGADTSEVHWNYKERMVTFKVPHAKRQDV

TVLGSQEGAMHSALAGATEIQNSGGTSIFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA, or the amino acid sequence:

(DENV4_M14, SEQ ID NO: 3)
MRCVGVGNRDFVEGVSGGAWVDLVLEHGGCVTTMAQGKPTLDFELTKTEA

TQLATLRKLCIEASISNITTATRCPTQGEPYLKEEQDQQYICRRDVVDRG

WGNGCGLFGKGGVVTCAKFSCLEPIEGKVVQYENLEYTVVVTVHNGDTHA

VGNDTSNHGVTATITPRSPSVEVKLPDYGELTLDCEPRSGIDFNEMILLT

MKKKAWMVHRQWFFDLPLPWTSGADTSEVHWNYKERMVTFKVPHAKRQDV

TVLGSQEGAMHSALAGATEIQNSGGTSIFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA, or the amino acid sequence:

(DENV4_M16, SEQ ID NO: 4)
MRCVGVGNRDFVEGVSGGAWVDLVLEHGGCVTTMAQGKPTLDFELTKTEA

TQLATLRKLCIEASISNITTDTRCPTQGEPYLKEEQDQQYICRRDVVDRG

WGNGCGLFGKGGVVTCAKFSCLEPIEGKVVQYENLEYTVVVTVHNGDQHA

VGNDTSNHGVTATITPRSPSVEVKLPDYGELTLDCEPRSGIDFNEMILLT

MKKKAWMVHRQWFFDLPLPWTSGATTSEPHWNYKERMVTFKVPHAKRQDV

TVLGSQEGAMHSALAGATEIQNSGGTSIFAGHLKCKVRMEKLRIKGMSYT

MCSGKFSIKKEMAETQHGTTVVKVKYEGAGAPCKVPIEIRDVNKEKVVGR

VISSTPLAENTNSPTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA.

In some embodiments, the present invention provides a chimeric dengue virus E glycoprotein comprising a dengue virus E glycoprotein backbone that comprises amino acid substitutions that introduce a protein domain from a dengue virus serotype that is different from the dengue virus serotype of the dengue virus E glycoprotein backbone, wherein the dengue virus E glycoprotein backbone is from dengue virus serotype 4 and the protein domain is from dengue virus serotype 2.

In some embodiments, the dengue virus E glycoprotein backbone of dengue virus serotype 4 comprises amino acid substitutions that introduce an epitope that is recognized by an antibody that is reactive with dengue virus serotype 2. In some embodiments, the antibody is monoclonal antibody 2D22.

In some embodiments, the protein domain is E glycoprotein domain III and in some embodiments, the chimeric dengue virus E glycoprotein described above as 4/2 can comprise, consist essentially of or consist of the amino acid sequence:

(DV4-EDIII-DV2, SEQ ID NO: 5)
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYS

MCTGKFKIVKEIAETQHGTIVIRVQYEGDGSPCKIPFEITDLEKRHVLGR

LITVNPIVTEKDSPVNIEAEPPFGDSYIIIGVEPGQLKLNWFKKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA.

In some embodiments, the chimeric dengue virus E glycoprotein can comprise the amino acid sequence:

(WT_DENV4, SEQ ID NO: 1)
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA, wherein said amino acid sequence comprises all, or less than all in any combination, of the following amino acid substitutions:
T300S, S303T, S307K, D309V, M312I, T320I, V322I, K323R, K325Q, A329D, A331S, V335I, I337F, R340T, V342L, N343E, E345R, K346H, V348L, V351L, S353T, S354V, T355N, L357I, A358V, E359T, N360E, T361K, N362D, V364P, T365V, L369A, V379I, G383E, N384P, S385G, A386Q, T388K, H390N and R393K.

Further embodiments of this invention include the reciprocal exchange virus, i.e., a dengue virus E glycoprotein of dengue virus serotype 2 with amino acid substitutions that introduce a dengue virus protein domain (e.g., domain III) from dengue virus serotype 4. Any other combination of dengue virus serotype backbone and substituted dengue virus protein domain from a different dengue virus serotype is included as an embodiment of this invention, including, for example the combinations 1/2, 1/3, 1/4, 1/2/3, 1/2/4, 1/3/4, 1/2/3/4, 2/1, 2/3, 2/4, 2/1/3, 2/1/4, 2/3/4, 2/1/3/4, 3/1, 3/2, 3/4, 3/1/2, 3/1/4, 3/2/4, 3/1/2/4, 4/1, 4/2, 4/3, 4/1/3, 4/1/2, 4/3/2, or 4/3/2/1 (wherein the first number of each combination defines the serotype of the backbone and the second, third or fourth number of each combination defines the serotype of the epitope(s) or domain(s) that have been introduced into the backbone).

Some embodiments of the present invention provide a chimeric dengue virus E glycoprotein comprising a dengue virus E glycoprotein backbone that comprises amino acid substitutions that introduce an epitope that is recognized by an antibody that is reactive with a dengue virus serotype that is different from the dengue virus serotype of the dengue virus E glycoprotein backbone, wherein the dengue virus E glycoprotein backbone is from dengue virus serotype 2 and the antibody is reactive with dengue virus serotype 1. In some embodiments, the antibody is monoclonal antibody 1F4 and in some embodiments, the chimeric dengue virus E glycoprotein comprises, consists essentially of or consists of the amino acid sequence:

(DENV2-1F4E, SEQ ID NO: 6)
MRCIGISNRDFVEGVSGGSWVDIVLEHGSCVTTMAKNKPTLDFELFKTEV

TNPAVLRKYCIEAKLTNTTTESRCPTQGEPSLNEEQDKRFICKHSMVDRG

WGNGCGLFGKGGIVTCAMFTCKKNMEGKVVQPENLKYSVIVTVHSGEEHA

VGNDTTEHGTTATITPQAPTSEIQLTDYGALTLECSPRTGLDFNEMVLLQ

MEDKAWLVHRQWFLDLPLPWLPGADTQESNWIQKETLVTFKNPHAKKQDV

VVLGSQEGAMHTALTGATEIQTSGTTTLFTGHLKCRLRMDKLQLKGMSYS

MCTGKFKIVKEIAETQHGTIVIRVQYEGDGSPCKIPFEITDLEKRHVLGR

LITVNPIVTEKDSPVNIEAEPPFGDSYIIIGVEPGQLKLNWFKKGSSIGQ

MFETTMRGAKRMAILGDTAWDFGSLGGVFTSIGKALHQVFGAIYGAAFSG

VSWTMKILIGVIITWIGMNSRSTSLSVSLVLVGVVTLYLGAVVQA.

In some embodiments of this invention, the chimeric E glycoprotein can comprise a dengue virus E glycoprotein backbone of dengue virus serotype 1, dengue virus serotype 2, or dengue virus serotype 3, that comprises one or more (e.g., 2, 3, 4, 5, 6, 7, 8, 9, 10, 11, 12, 13, 14 or all 15) of the following amino acid substitutions, in any combination to introduce an epitope from dengue virus serotype 4 that is reactive with monoclonal antibody 5H2: A at residue 155, V at residue 160, T at residue 161, A at residue 162, M at residue 163, S at residue 168, S at residue 170, V at residue 171, V at residue 173, K at residue 174, P at residue 176, D at residue 177, E at residue 180, K at residue 291 and R at residue 293. Amino acid numbering is based on the amino acid sequence of WT_DENV4 provided herein.

The present invention provides additional no limiting examples of chimeric dengue virus E glycoprotein's of this invention that can be used in the compositions and methods described herein in the SEQUENCES section provided herein.

The present invention also provides various therapeutic methods, including, for example, method of producing an immune response to a dengue virus in a subject, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Additionally provided herein is a method of treating a dengue virus infection in a subject, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

In further embodiments, the present invention provides a method of preventing a disorder associated with dengue virus infection in a subject, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Also provided herein is a method of protecting a subject from the effects of dengue virus infection, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

The present invention also provides various diagnostic methods, including, for example, a method of identifying the presence of a neutralizing antibody to dengue virus serotype 3 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 to the subject in an amount effective to induce an antibody response to the E glycoprotein; b) contacting a biological sample from the subject with flavivirus particles comprising the E glycoprotein of step (a) above under conditions whereby neutralization of the flavivirus particles can be detected; and c) detecting neutralization in step (b), thereby identifying the presence of a neutralizing antibody to dengue virus serotype 3 and/or 4 in the biological sample from the subject.

Further provided herein is a method of identifying the presence of a neutralizing antibody to dengue virus serotype 2 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 to the subject in an amount effective to induce an antibody response to the E glycoprotein; b) contacting a biological sample from the subject with flavivirus particles comprising the E glycoprotein of step (a) above under conditions whereby neutralization of the flavivirus particles can be detected; and c) detecting neutralization in step (b), thereby identifying the presence of a neutralizing antibody to dengue virus serotype 2 and/or 4 in the biological sample from the subject.

The present invention also provides a method of identifying the presence of a neutralizing antibody to dengue virus serotype 1 and/or 2 in a biological sample from a subject, comprising: a) administering a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 to the subject in an amount effective to induce an antibody response to the E glycoprotein; b) contacting a biological sample from the subject with flavivirus particles comprising the E glycoprotein of step (a) above under conditions whereby neutralization of the flavivirus particles can be detected; and c) detecting neutralization in step (b), thereby identifying the presence of a neutralizing antibody to dengue virus serotype 1 and/or 2 in the biological sample from the subject.

A method is also provided herein of identifying the presence of a neutralizing antibody to dengue virus serotype 3 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 to the subject in an amount effective to induce an antibody response to the E glycoprotein; and b) detecting neutralization in step (a), thereby identifying the presence of a neutralizing antibody to dengue virus serotype 3 and/or 4 in the biological sample from the subject.

Furthermore, the present invention provides a method of identifying the presence of a neutralizing antibody to dengue virus serotype 2 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 to the subject in an amount effective to induce an antibody response to the E glycoprotein; and b) detecting neutralization in step (a), thereby identifying the presence of a neutralizing antibody to dengue virus serotype 2 and/or 4 in the biological sample from the subject.

In additional embodiments, the present invention provides a method of identifying the presence of a neutralizing antibody to dengue virus serotype 1 and/or 2 in a biological sample from a subject, comprising: a) administering a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 to the subject in an amount effective to induce an antibody response to the E glycoprotein; and b) detecting neutralization in step (a), thereby identifying the presence of a neutralizing antibody to dengue virus serotype 1 and/or 2 in the biological sample from the subject.

The present invention further provides a method of identifying an immunogenic composition that induces a neutralizing antibody to dengue virus serotype 3 and/or 4 in a subject, the method comprising: a) administering a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 to the subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d identifying the immunogenic composition as inducing a neutralizing antibody to dengue virus serotype 3 and/or 4 in the subject if the biological sample comprises an antibody that neutralizes flavivirus particles comprising the E glycoprotein of (a).

Furthermore, the present invention provides a method of identifying an immunogenic composition that induces a neutralizing antibody to dengue virus serotype 2 and/or 4 in a subject, the method comprising: a) administering a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 to the subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d identifying the immunogenic composition as inducing a neutralizing antibody to dengue virus serotype 2 and/or 4 in the subject if the biological sample comprises an antibody that neutralizes flavivirus particles comprising the E glycoprotein of (a).

The present invention further provides a method of identifying an immunogenic composition that induces a neutralizing antibody to dengue virus serotype 1 and/or 2 in a subject, the method comprising: a) administering a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 to the subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d identifying the immunogenic composition as inducing a neutralizing antibody to dengue virus serotype 1 and/or 2 in the subject if the biological sample comprises an antibody that neutralizes flavivirus particles comprising the E glycoprotein of (a).

In additional embodiments, the present invention provides a method of identifying an immunogenic composition that induces a neutralizing antibody to dengue virus serotype 3 and/or 4 in a subject, the method comprising: a) contacting a biological sample from a subject that has been administered an immunogenic composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4, with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to dengue virus serotype 3 and/or 4 in the subject if the biological sample comprises an antibody that neutralizes flavivirus particles comprising the E glycoprotein of (a).

Additionally, the present invention provides a method of identifying an immunogenic composition that induces a neutralizing antibody to dengue virus serotype 2 and/or 4 in a subject, the method comprising: a contacting a biological sample from a subject that has been administered an immunogenic composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to dengue virus serotype 2 and/or 4 in the subject if the biological sample comprises an antibody that neutralizes flavivirus particles comprising the E glycoprotein of (a).

Additionally provided herein is a method of identifying an immunogenic composition that induces a neutralizing antibody to dengue virus serotype 1 and/or 2 in a subject, the method comprising: a) contacting a biological sample from a subject that has been administered an immunogenic composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to dengue virus serotype 1 and/or 2 in the subject if the biological sample comprises an antibody that neutralizes flavivirus particles comprising the E glycoprotein of (a).

The present invention further provides a method of detecting an antibody to dengue virus serotype 3 and/or 4 in a sample, comprising: a) contacting the sample with a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 under conditions whereby an antigen/antibody complex can form; and b) detecting formation of an antigen/antibody complex, thereby detecting an antibody to dengue virus serotype 3 and/or 4 in the sample.

The present invention also provides a method of detecting an antibody to dengue virus serotype 2 and/or 4 in a sample, comprising: a) contacting the sample with a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 under conditions whereby an antigen/antibody complex can form; and b) detecting formation of an antigen/antibody complex, thereby detecting an antibody to dengue virus serotype 3 and/or 4 in the sample.

Also provided herein is a method of detecting an antibody to dengue virus serotype 1 and/or 2 in a sample, comprising; a) contacting the sample with a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 under conditions whereby an antigen/antibody complex can form; and b) detecting formation of an antigen/antibody complex, thereby detecting an antibody to dengue virus serotype 1 and/or 2 in the sample.

Further provided herein is a method of identifying an antibody to dengue virus serotype 3 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 3 and/or 4 in the biological sample from the subject.

Additionally provided herein is a method of identifying an antibody to dengue virus serotype 2 and/or 4 in a biological sample from a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 2 and/or 4 in the biological sample from the subject.

In yet further embodiments, the present invention provides a method of identifying an antibody to dengue virus serotype 1 and/or 2 in a biological sample from a subject, comprising: a) administering a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 1 and/or 2 in the biological sample from the subject.

A method is additionally provided herein of identifying an antibody to dengue virus serotype 3 and/or 4 in a biological sample from a subject, comprising: a) contacting a biological sample from a subject that has been administered an immunogenic composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 with the E glycoprotein under conditions whereby an antigen/antibody complex can form; and c) detecting formation of an antigen/antibody complex, thereby identifying an antibody to dengue virus serotype 3 and/or 4 in the biological sample from the subject.

The present invention further provides a method of identifying an antibody to dengue virus serotype 2 and/or 4 in a biological sample from a subject, comprising: a) contacting a biological sample from a subject that has been administered an immunogenic composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 with the E glycoprotein under conditions whereby an antigen/antibody complex can form; and b) detecting formation of an antigen/antibody complex, thereby identifying an antibody dengue virus serotype 2 and/or 4 in the biological sample from the subject.

The present invention further provides a method of identifying an antibody to dengue virus serotype 1 and/or 2 in a biological sample from a subject, comprising: a) contacting a biological sample from a subject that has been administered an immunogenic composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 with the E glycoprotein under conditions whereby an antigen/antibody complex can form; and b) detecting formation of an antigen/antibody complex, thereby identifying an antibody dengue virus serotype 1 and/or 2 in the biological sample from the subject.

The present invention further provides a method of identifying an immunogenic composition that induces an antibody to dengue virus serotype 3 and/or 4 in a subject, the method comprising: a) contacting a biological sample from a subject that has been administered an immunogenic composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 with the E glycoprotein under conditions whereby an antigen/antibody complex can form; and b) detecting formation of an antigen/antibody complex, thereby identifying an immunogenic composition that induces an antibody to dengue virus serotype 3 and/or 4 in the subject.

Further provided herein is a method of identifying an immunogenic composition that induces an antibody to dengue virus serotype 2 and/or 4 in a subject, the method comprising: a contacting a biological sample from a subject that has been administered an immunogenic composition comprising an E glycoprotein of any of claims 6-8 with the E glycoprotein under conditions whereby an antigen/antibody complex can form; and b) detecting formation of an antigen/antibody complex, thereby identifying an immunogenic composition that induces an antibody to dengue virus serotype 2 and/or 4 in the subject.

Also provided herein is a method of identifying an immunogenic composition that induces an antibody to dengue virus serotype 1 and/or 2 in a subject, the method comprising: a) contacting a biological sample from a subject that has been administered an immunogenic composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 with the E glycoprotein under conditions whereby an antigen/antibody complex can form; and b) detecting formation of an antigen/antibody complex, thereby identifying an immunogenic composition that induces an antibody to dengue virus serotype 1 and/or 2 in the subject.

In some embodiments of the present invention, a method is provided of identifying an immunogenic composition that induces a neutralizing antibody to dengue virus serotype 3 and/or 4 in a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 3 and/or a composition comprising an E glycoprotein comprising an E glycoprotein backbone of serotype 3 comprising amino acid substitutions that introduce a dengue virus protein domain of dengue virus serotype 4 to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an immunogenic composition that induces a neutralizing antibody to dengue virus serotype 3 and/or 4 in the subject.

The present invention additionally provides a method of identifying an immunogenic composition that induces a neutralizing antibody to dengue virus serotype 2 and/or 4 in a subject, comprising: a) administering a composition comprising an E glycoprotein comprising an E glycoprotein backbone of serotype 4 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce an epitope that is recognized by an antibody that is reactive with dengue virus serotype 4 and/or a composition comprising an E glycoprotein comprising an E glycoprotein backbone of serotype 4 comprising amino acid substitutions that introduce a dengue virus protein domain of dengue virus serotype 2 and/or a composition comprising an E glycoprotein comprising an E glycoprotein backbone of serotype 2 comprising amino acid substitutions that introduce a dengue virus protein domain of dengue virus serotype 4 to the subject in an amount effective to induce an antibody response to the E glycoprotein; b contacting a biological sample from the subject with the E glycoprotein of (a) under conditions whereby an antigen/antibody complex can form; and c) detecting formation an antigen/antibody complex, thereby identifying an immunogenic composition that induces a neutralizing antibody to dengue virus serotype 2 and/or 4 in the subject.

Also provided herein is a method of identifying an immunogenic composition that induces a neutralizing antibody to dengue virus serotype 1 and/or 2 in a subject, comprising: a) administering a composition comprising an E glycoprotein comprising an E glycoprotein backbone of serotype 2 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 2 and/or a composition comprising an E glycoprotein comprising an E glycoprotein backbone of serotype 2 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 2 to the subject in an amount effective to induce an antibody response to the E glycoprotein; b contacting a biological sample from the subject with the E glycoprotein of (a) under conditions whereby an antigen/antibody complex can form; and c) detecting formation an antigen/antibody complex, thereby identifying an immunogenic composition that induces a neutralizing antibody to dengue virus serotype 1 and/or 2 in the subject.

In some embodiments, the present invention provides a method of determining an amount of the antibodies produced to the transplanted epitope or domain. For example, DENV3 antibodies that target the 5J7 region could be measured by comparing neutralization of DENV4 M14 with the parent DENV4, with the expectation that DENV3 antibodies could neutralize some portion of DENv4 M14 but not parental DENV4.

The present invention also provides a dengue virus particle, a flavivirus particle and a virus like particle (VLP) comprising the chimeric E glycoprotein of this invention. The dengue virus E glycoprotein of the invention can be present in an intact virus particle (e.g., a killed or live attenuated virus particle or a recombinant dengue virus vector) or a virus-like particle (VLP), which may optionally be an intact dengue virus particle or dengue virus VLP.

Also provided is an isolated nucleic acid molecule encoding the E glycoprotein of this invention, an isolated nucleic acid molecule encoding the dengue virus particle, the flavivirus particle or the VLP of this invention, a vector comprising the nucleic acid molecule of this invention and a population of dengue virus particles and/or flavivirus particles comprising the dengue virus particle and/or flavivirus particle this invention.

Further provided herein is a composition comprising the E glycoprotein of this invention in a pharmaceutically acceptable carrier, a composition comprising the nucleic acid molecule of this invention in a pharmaceutically acceptable carrier, a composition comprising the virus particle of this invention, a composition comprising the population of this invention in a pharmaceutically acceptable carrier and a composition comprising the VLP of this invention in a pharmaceutically acceptable carrier.

In some embodiments, production of the chimeras of this invention can be carried out by introducing some (e.g., 1, 2, 3, 4, 5, 6, 7, 8, 9, 10, 11, 12, 13, 14, 15, etc.) or all of the amino acid substitutions identified as part of a dengue virus epitope and/or dengue virus protein domain into a dengue virus E glycoprotein backbone or flavivirus E glycoprotein backbone. Not every amino acid identified as part of a dengue virus epitope or dengue virus protein domain is required to be substituted to produce a chimeric protein of this invention. For example, in some embodiments further substitutions and/or omission of substitutions of about 1, 2, 3, 4 or 5 amino acids at either end of the contiguous amino acid sequences identified as part of a dengue virus epitope or dengue virus domain can be included in the production of a chimera of this invention. The number of substitutions necessary to produce the desired conformational epitope or domain can be readily determined by one of ordinary skill in the art according to the teachings herein and according to protocols well known in the art. The amino acid residue numbering provided in the amino acid sequences set forth here is based on the respective unmodified (e.g., wild type) E glycoprotein amino acid sequence of the respective DENV serotype, as provided herein. However it would be readily understood by one of ordinary skill in the art that the equivalent amino acid positions in other dengue virus E glycoprotein amino acid sequences or other flavivirus E glycoprotein amino acid sequences can be readily identified and employed in the production of the chimeric proteins of this invention.

In some embodiments, the present invention provides a chimeric flavivirus E glycoprotein in which amino acid substitutions are made to introduce one or more dengue virus epitomes into a flavivirus E glycoprotein from a flavivirus that is not a dengue virus. Thus, in some embodiments, the present invention provides a flavivirus E glycoprotein comprising a chimeric E glycoprotein comprising a flavivirus E glycoprotein backbone that is not a dengue virus E glycoprotein backbone, wherein the flavivirus E glycoprotein backbone comprises amino acid substitutes that introduce one or more epitopes that are recognized by a respective antibody that is reactive with a dengue virus.

No limiting examples of flaviviruses that can be used include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652) and any other flavivirus now known or later identified.

It is known in the art that many attempts to produce dengue virus vaccines result in the production of non-neutralizing antibodies, which may increase the likelihood of pathology upon subsequent exposure to natural infection or vaccine. Another approach to provide an engineered epitope is to deliver all or a portion of the dengue virus E protein incorporated into another flavivirus particle or VLP. In representative embodiments, the heterologous flavivirus is West Nile virus or Yellow Fever virus. Portions of the E protein can be grafted into the E protein of the heterologous flavivirus backbone, e.g., to reduce the generation of non-neutralizing dengue virus antibodies to non-neutralizing epitopes present in the dengue virus E protein and/or other dengue virus structural proteins.

Thus, a chimeric flavivirus or chimeric flavivirus VLP can present the quaternary dengue virus epitope in proper conformation while reducing the generation of non-neutralizing antibodies to other portions of the dengue virus E protein and/or other structural proteins that are not presented in the chimeric flavivirus or flavivirus VLP.

In some embodiments of the invention the individual and conformational epitopes of the flavivirus E glycoprotein or dengue virus E glycoprotein can be presented on a synthetic backbone or support structure so that the epitopes within the synthetic backbone or support structure mimic the conformation and arrangement of the epitopes within the structure of the E glycoprotein, virus particle or VLP.

In still further embodiments of the invention, the present invention provides peptide mimitopes (see, Meloen et al. (2000) 1 *J. Mol. Recognit.* 13, 352-359) that mimic the individual and conformational epitopes of the E glycoproteins of the invention. Mimitopes may be identified using any technique known in the art, including but not limited to surface stimulation, random peptide libraries or phage display libraries, as well as an antibody or antibodies to the individual and conformational epitopes of the E glycoproteins of the invention.

The invention further provides a nucleic acid molecule (e.g., isolated nucleic acid molecule) encoding a dengue virus peptide, a dengue virus protein domain, a dengue virus polypeptide or a flavivirus polypeptide of the invention.

The invention further provides a nucleic acid molecule (e.g., an isolated nucleic acid molecule) encoding a chimeric flavivirus particle or a chimeric flavivirus virus-like particle (VLP) (e.g., a viral coat of the flavivirus particle) of the invention.

Also provided is a nucleic acid vector comprising a nucleic acid molecule of the invention.

Also provided is a cell (e.g., an isolated cell) comprising a vector, a nucleic acid molecule, a dengue virus protein, a dengue virus peptide, a dengue virus protein domain, a flavivirus protein, a flavivirus peptide, flavivirus protein domain, a chimeric dengue virus particle, a chimeric dengue virus VLP, a chimeric flavivirus VLP and/or a chimeric flavivirus particle of this invention, singly or in any combination.

The invention also provides immunogenic compositions comprising the cells, vectors, nucleic acids molecules, dengue virus proteins, chimeric dengue virus VLPs, chimeric dengue virus particles, chimeric flavivirus VLPs and/or chimeric flavivirus particles of the invention, singly or in any combination. In some embodiments, the immunogenic composition is monovalent. In some embodiments, the immunogenic composition is multivalent (e.g., bivalent, trivalent or tetravalent) for dengue virus serotypes DEN1, DEN2, DEN 3 and/or DEN4 in any combination. The dengue virus chimeric E glycoproteins of this invention can be administered to a subject singly or in any combination, including any combination of priming and boosting according to such immunization protocols that are known in the art. The dengue virus chimeric E glycoprotein of this invention can be 1/2, 1/3, 1/4, 1/2/3, 1/2/4, 1/3/4, 1/2/3/4, 2/1, 2/3, 2/4, 2/1/3, 2/1/4, 2/3/4, 2/1/3/4, 3/1, 3/2, 3/4, 3/1/2, 3/1/4, 3/2/4, 3/1/2/4, 4/1, 4/2, 4/3, 4/1/3, 4/1/2, 4/3/2, or 4/3/2/1 (wherein the first number of each combination defines the serotype of the backbone and the second, third or fourth number of each combination defines the serotype of the epitope(s) or domain (s) that have been introduced into the backbone). In some embodiments, a prime/boost combination would be used that results in administration of antigens representative of all four dengue virus serotypes. Such a prime/boost regimen can include administration of any combination of antigens in any order to achieve this result. A nonlimiting example of a prime/boost protocol can include priming at day 0 and boosting at 3 months and 6 months, or boosting at 6 months and 1 year, respectively. This protocol could also be modified to include only one boost at either 3 months, 6 months or 1 year.

The invention encompasses methods of producing an immune response to a dengue virus in a subject, comprising administering to the subject an effective amount of a dengue virus protein, a chimeric dengue virus particle, a chimeric dengue virus VLP, a chimeric flavivirus VLP, a chimeric flavivirus particle, a nucleic acid molecule, a vector, a cell and/or immunogenic composition of the invention, singly or in any combination.

In some embodiments, the present invention can advantageously be practiced to induce an immune response against one, two, three or all four of the DEN1, DEN2, DEN3 and DEN4 serotypes. In some embodiments, the dengue virus chimeric E glycoprotein of this invention and/or a nucleic acid molecule encoding the dengue virus chimeric E glycoprotein of this invention can be administered to a subject singly or in any combination and/or sequence to induce an immune response (e.g., a balanced immune response, in which the parameters of dengue immunity being measured are nearly equivalent for all four DENV serotypes) to all four DENV serotypes. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to more serious complications and/or disease, such as dengue hemorrhagic fever.

A still further aspect of the invention is a method of treating a dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

A still further aspect of the invention is a method of preventing a dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

A still further aspect of the invention is a method of protecting a subject from the effects of dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

By "protecting a subject from the effects of dengue virus infection" it is meant that the subject does not develop a disease or disorder caused by a dengue virus infection, or if the subject does develop a disease or disorder caused by a dengue virus infection, the disease or disorder is of less severity and/or symptoms are reduced and/or less severe in the subject in comparison to what the subject would experience upon infection by a dengue virus in the absence of the administration of the dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention There are four serotypes of dengue virus (DENV-1, DENV-2, DENV-3 and DENV-4). Within each serotype there are a number of different strains or genotypes. The dengue virus epitopes and protein domains of this invention can be derived from any dengue virus, including all serotypes, strains and genotypes, now known or later identified.

In embodiments of the invention, the dengue virus is UNC1017 strain (DEN1), West Pacific 74 strain (DEN1), S16803 strain (DEN2), UNC2005 strain (DEN2), S16803 strain (DEN2), UNC3001 strain (DEN3), UNC3043 (DEN3 strain 059.AP-2 from Philippines, 1984), UNC3009 strain (DEN3, D2863, Sri Lanka 1989), UNC3066 (DEN3, strain 1342 from Puerto Rico 1977), CH53489 strain (DEN3), UNC4019 strain (DEN4), or TVP-360 (DEN4).

In embodiments of the invention, an "immunogenically active fragment" of a dengue virus polypeptide (e.g., the E protein) comprises, consists essentially of or consists of at least about 6, 8, 10, 12, 15, 20, 30, 50, 75, 100, 125, 150, 200, 250, 300, 350, 400, 450 or more amino acids, optionally contiguous amino acids, and/or less than about 495, 475, 450, 425, 400, 350, 300, 250, 200, 150, 100, 75 or 50 amino acids, optionally contiguous amino acids, including any combination of the foregoing as long as the lower limit is less than the upper limit, and the "immunogenically active fragment" induces an immune response (e.g., IgG and/or IgA that react with the native antigen), optionally a protective immune response, against dengue virus in a host and induces the production of antibodies (e.g., neutralizing antibodies) that specifically bind to the quaternary dengue virus epitope(s) described herein.

The term "epitope" as used herein means a specific combination of amino acid residues in an amino acid sequence that, when present in the proper conformation, provides a reactive site for an antibody (e.g., B cell epitope) or T cell receptor (e.g., T cell epitope).

Portions of a given polypeptide that include a B-cell epitope can be identified using any number of epitope mapping techniques that are known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci*. USA 81:3998-4002; Geysen et al. (1986) *Molec. Immunol.* 23:709-715.

Similarly, conformational epitopes can be readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides, VLPs and viral vectors of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DENV-1, DENV-2, DENV-3 and DENV-4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of dengue virus infection.

"Effective amount" as used herein refers to an amount of a vector, nucleic acid, epitope, polypeptide, cell, particle, VLP, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing dengue virus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating dengue virus infection in a subject, whether against one or multiple strains, genotypes or serotypes of dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to dengue virus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by dengue virus. Alternatively, a subject according to the invention can also include a subject not previously known or suspected to be infected by dengue virus or in need of treatment for dengue virus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to dengue virus.

A "subject in need" of the methods of the invention can be a subject known to be, or suspected of being, infected with, or at risk of being infected with, dengue virus.

Pharmaceutical formulations (e.g., immunogenic formulation) comprising the dengue virus epitopes, polypeptides, chimeric flavivirus VLPs or chimeric flavivirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immunomodulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al., *Vaccine* 24(6):766-75 (2005)), QS-21, Freund's adjuvant (complete and incomplete), aluminum hydroxide, N-acetylmuramyl-L-threonyl-D-isoglutamine (thr-MDP), N-acetylnormuramyl-L-alanyl-D-isoglutamine (CGP 11637, referred to as nor-MDP), N-acetylmuramyl-L-alanyl-D-isoglutaminyl-L-alanine-2-(F-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 μg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

In embodiments of the invention, the dosage of a virus particle of this invention can be in a range of about $10^3$ to about $10^8$ plaque forming units/focus forming units (PFUs/FFUs). In embodiments of this invention, the dosage of a VLP of this invention can be in a range of about 500 micrograms to about 5 milligrams. In embodiments of this invention, the dosage of a protein of this invention can be in a range of about $10^0$ to about $10^4$ micrograms+/−adjuvant.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

EXAMPLES

Example 1.

Transplantation of a Complex Quaternary Serotype-Specific Neutralizing Antibody Epitope Between Dengue 3 and 4 Reveals Determinants of Polyclonal Neutralization Responses Dengue virus (DENV) is the most significant human arboviral disease worldwide with upwards of 300 million infections annually; however the determinants of human immune responses to DENV infection remain largely unknown. Thus we set out to develop tools with which to characterize antibody (Ab) responses to DENV infection in humans. Using reverse genetics we developed infectious clones (IC) for all 4 DENV serotypes which allow us to study Ab-virus interactions. Characterization of a panel of monoclonal Abs (mAb) identified a strongly type-specific neutralizing Ab of DENV3. Using a structure-guided approach a 12 Å region of the envelope (E) protein domain I/II (EDI/II) hinge region encompassing mutations that led to escape of neutralization was identified and transplanted from DENV4 into DENV3 (rDENV3/4) to assess the contribution of this epitope to the polyclonal immune response in humans. Interestingly, this rDENV3/4 gained full sensitivity to neutralization by human DENV4 immune sera while becoming resistant to DENV3 sera, indicating that this EDI/II hinge region contains major determinants of type-specific neutralization responses. When the reciprocal transplant was made into DENV4, mAb binding was not retained and there was not a significant shift in neutralization profiles, indicating that the adjacent residues in the recipient DENV serotype play a role in epitope presentation on the virion surface. The addition of 5 amino acid residues from DENV3 into DENV4 was able to restore mAb binding and neutralization, however polyclonal serum neutralization remained largely unchanged. Finally, we moved a complex quaternary epitope encompassing residues spanning multiple E dimers into DENV4 (rDENV4/3). This DENV4/3 was viable and grew to high infectious titers and exhibited sensitivity to DENV3 immune sera, while neutralization responses to DENV4 remained largely unchanged. These results provide insights into the determinants of type specific neutralization responses that could guide future development of rationally designed DENV vaccine platforms.

Example 2.

Development and Characterization of a Recombinant Dengue 4 Virus that Captures Type-Specific Neutralization Determinants of Both Dengue 3 and Dengue 4

Development of a Reverse Genetics Platform for Recombinant DENV4 Generation

Figure 1:
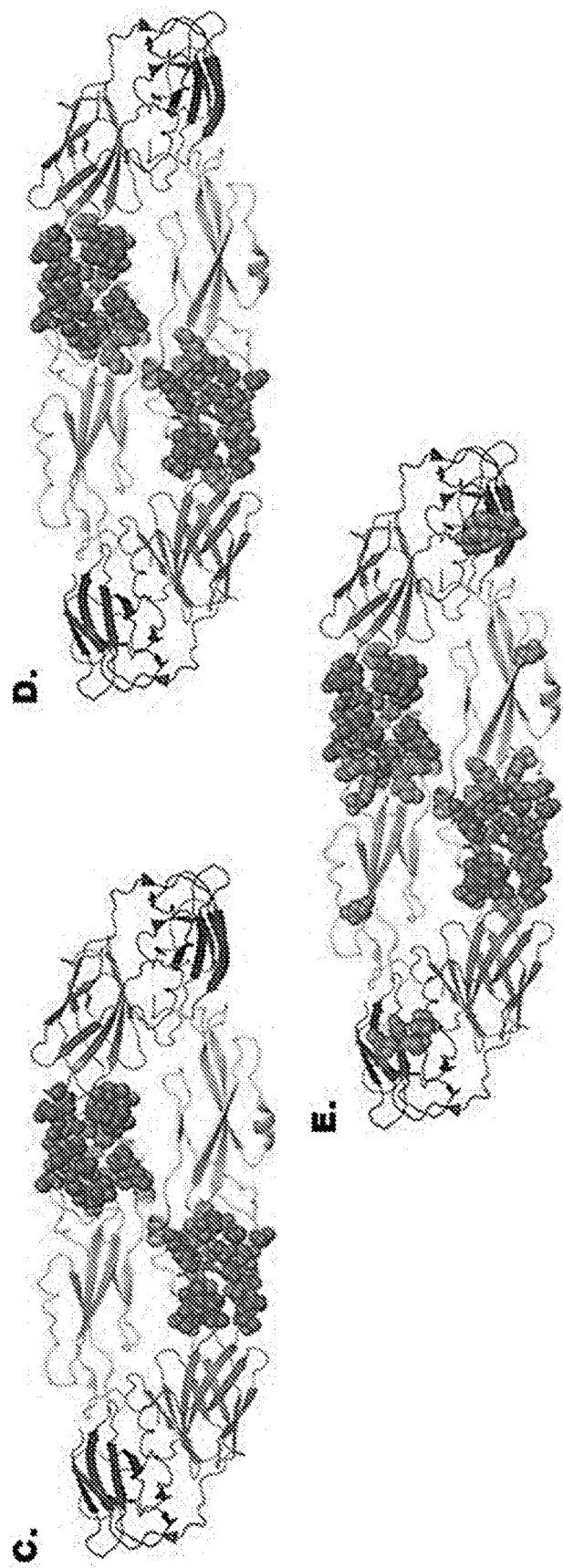
FIG. 1. Design of infectious cDNA clones of DENV 3 and 4 and generation of recombinant DENV4/3 viruses. (A) Genome schematic of DENV3 and DENV4 infectious clone design including restriction endonucleases used to generate subgenomic fragments. Size of subgenomic fragments indicates positions in DENV genome where breaks were made to circumvent bacterial instability and toxicity. (B) Amino acids changed in DENV4 E protein by transplantation of DENV3 sequences to generate DENV4 M12, M14, and M16 respectively. Amino acid number represents residue from start of E protein of DENV4. Ribbon structure of DENV3 E protein dimer with AA transferred into DENV4 M12 (C; green residues), DENV4 M14 (D; green+cyan residues), and DENV4 M16 (E; green+cyan+orange residues) indicated. Colors correspond to highlighted AA residues in (B).

We have previously described the generation and characterization of a reverse genetics system for production of recombinant DENV3 (rDENV3) (FIG. 1, Panel A). Utilizing similar techniques we have developed a cDNA infectious clone (IC) system for a clinical isolate of DENV4 isolated in Sri Lanka in 1989 and belonging to genogroup I. In order to circumvent instability and toxicity during bacterial plasmid amplification in *E coli*, the DENV4 genome was subcloned into 4 distinct fragments (FIG. 1, Panel A). Naturally occurring class Ifs restriction endonuclease sites in the DENV4 genome at nucleotide (NT) position 3216 (PflMI; recognition sequence: CCAAACAGTGG, SEQ ID NO:7), 5482 (DraIII; CACCAGGTG), and 8855 (PflMI; CCAGATTTTGG, SEQ ID NO:8) were utilized to divide the genomic cDNA. Additionally, an EcoRV site in the bacterial vector and upstream of a T7 promoter sequence was used to generate the 5' end of the genome, while a BsmBI site in the vector was used for the 3' genomic end (FIG. 1, Panel A). Following bacterial amplification of plasmids containing genomic cDNA fragments, plasmids were digested with appropriate restriction endonucleases, purified by agarose gel electrophoresis, ligated with T4 DNA ligase, and transcribed with T7 RNA polymerase containing 5' cap analogue. In vitro transcribed RNAs were then electroporated into either Vero-81 or BHK-21 cells. Cells were cultured for 4-6 days at which time supernatants were collected, clarified by centrifugation, and passaged onto C6/36 (*Aedes albopictus*) cells for an additional 4 days. Supernatants were again collected and clarified, and titrated for use as working viral stocks. rDENV4 demonstrated phenotypic properties (growth kinetics, peak infectious titers, and infectious focus morphology/size) identical to that of the parental natural isolate.

Transplantation of a Type-Specific Neutralizing DENV3 mAb Epitope into DENV4

Previous studies have identified a strongly type-specific human monoclonal antibody (hmAb) specific for DENV3 (5J7). These studies, however, only identified single point mutations that led to escape of DENV3 neutralization from this hmAb. In order to further characterize this hmAb epitope, we sought to transplant the amino acid (AA) residues encompassing this epitope from DENV3 into DENV4 using our novel reverse genetics platform. Using both the published and unpublished escape mutations as a guide, an approximately 12 angstrom circumference encompassing the envelope domain I/II (EDI/II) hinge region was superimposed upon the DENV3 E protein crystal structure to approximate the footprint of an antibody epitope:paratope binding region. Following AA and NT alignments between DENV3 and DENV4, interserotypic variant AA were identified and selected for transplantation from DENV3 into DENV4. NT sequences in the DENV4 IC were modified to facilitate AA changes to match DENV3, and subgenomic cDNAs capturing these changes were synthesized (BioBasic; Amherst, N.Y.). rDENV were generated as described above, and recovered virus used for phenotypic characterization. In order to maximize probability of successful epitope transplantation, 3 distinct rDENV were generated each containing sequentially additional DENV3 residues and thus transplanting larger theoretical epitope footprints. These rDENV have been designated DENV4 M12, DENV4 M14, and DENV4 M16, with increasing sizes of DENV3 sequence transplanted respectively (FIG. 1, Panels B-C). Of note, the DENV3 transplantation into DENV4 M16 encompasses a hypothetical complex quaternary epitope of 5J7, and to our knowledge represents the first time an epitope of this nature has been transplanted between distinct viruses.

rDENV4/3 Viruses are Viable and Demonstrate Distinct Fitness Characteristics In Vitro All 3 of the rDENV4/3 viruses (DENV4 M12, M14, and M16) were successfully recovered following electroporation and subsequent passage on C6/36 cells. Peak infectious titers from C6/36 cells (and measured by focus formation assay on Vero-81 cells) were found to be comparable to that of the parental WT DENV3 and DENV4 IC (FIG. 2, Panel A). DENV4 M12 and M14 demonstrated a peak titer similar to that of WT DENV3, all of which are approximately 1 $\log_{10}$ lower than that of WT DENV4 in this system. DENV4 M16, however, displayed a more attenuated growth phenotype with peak titers reaching about $2 \times 10^6$ ffu/ml, about 50-fold less than WT DENV3 and 300-fold less than WT DENV4 (FIG. 2, Panel A). Correspondingly, infectious foci size was also smaller in the rDENV as compared to their WT parents. DENV4 M12 and M14 foci are smaller than WT, but still significantly larger than DENV4 M16, which forms very small pinpoint foci on Vero-81 cells (FIG. 2, Panel B).

Similar fitness analyses were carried out on C6/36 mosquito cells. Multi-step growth curves (MOI=0.01) were performed on DENV4 M12, M14, M16, and parental WT DENV3 and DENV4 (FIG. 3, Panel A). In general, no significant fitness defects were seen at early time points (<96 hr post-inoculation (hpi)) however DENV4 M14 lagged behind WT at 96 and 120 hpi before demonstrating a burst at 144 hpi. Additionally, DENV4 M16 displayed decreased growth kinetics at 120 hpi and later with infectious titers about 2 $\log_{10}$ lower than other strains. In each case cell health could have played a role in this attenuation and as such further investigation is required. These data do, however, indicate that at least at early time points in infection the rDENV do not demonstrate significant growth attenuation in arthropod cells as compared to WT DENV. Interestingly, in contrast to Vero cells, infectious foci of DENV4 M12, M14, and M16 (FIG. 3, Panel B) do not show substantial differences in size or morphology as compared to WT DENV3 or 4, or to each other. This correlated well with growth curve data, and suggests that determinants of rDENV attenuation may be cell type specific to Vero-81 and/or mammalian cells in general. These data indicate that rDENV4 viruses containing transplanted regions of DENV3 are viable and demonstrate suitable growth characteristics for further characterization.

rDENV4/3 Display Varying Degrees of Reactivity to hmAb 5J7

Figure 4:
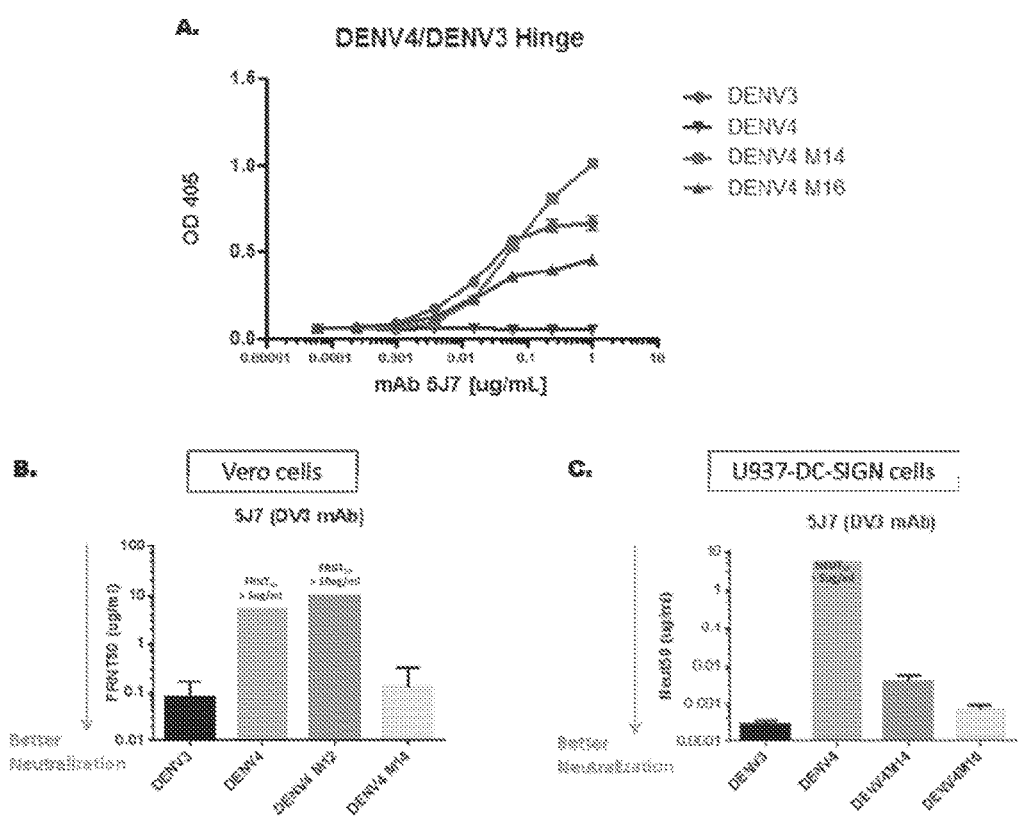
FIG. 4. Binding and neutralization of hmAb 5J7 on rDENV4/3. (A) ELISA OD values for DENV3-specific hmAb 5J7 on DENV3, DENV4, DENV4 M14, and DENV4 M16. 5J7 did not bind DENV4 M12 and displayed an identical curve to WT DENV4 (data not shown). Neutralization assays on Vero-81 (B) and U937-DC-SIGN (C) for DENV3, DENV4, DENV4 M12, M14, and M16. Data presented as μg/ml required to neutralize 50% of viral infectivity.

Assays were performed to determine the level to which the epitope for hmAb 5J7 was transplanted from DENV3 into DENV4 in the 3 rDENV. ELISAs were undertaken to assess binding of the DENV3-specific hmAb 5J7 to both WT and rDENV viruses. These revealed that 5J7 bound WT DENV3, but not DENV4, consistent with previous data. Interestingly, 5J7 was completely unable to bind DENV4 M12, while both DENV4 M14 and M16 displayed enough of the DENV3 epitope to facilitate 5J7 binding at levels near or exceeding that of WT DENV3 (FIG. 4, Panel A). These data indicate that no more than 4 AA (the difference in transplanted AA between DENV4 M12 and M14) were responsible for conferring 5J7 binding to DENV4 M14. As a corollary to these binding studies, virus neutralization assays were performed using 5J7 to assess sensitivity to neutralization of the rDENV4 panel. In agreement with the ELISA binding data, DENV4 M12 was incapable of neutralization with 5J7, while both DENV4 M14 and M16 were neutralized by 5J7 at Ab concentrations comparable to that of WT DENV3 (FIGS. 4B and C). Significantly, these results were consistent (for DENV4 M14) in 2 distinct cell lines (Vero-81 and U937 expressing DC-SIGN) believed to capture neutralization sensitivities for highly distinct (mature vs. immature) virus particles, indicating particle maturation state of these rDENV may not affect 5J7 neutralization.

rDENV4/3 have Bivalent Sensitivity to Polyclonal Serum Neutralization

Figure 5:
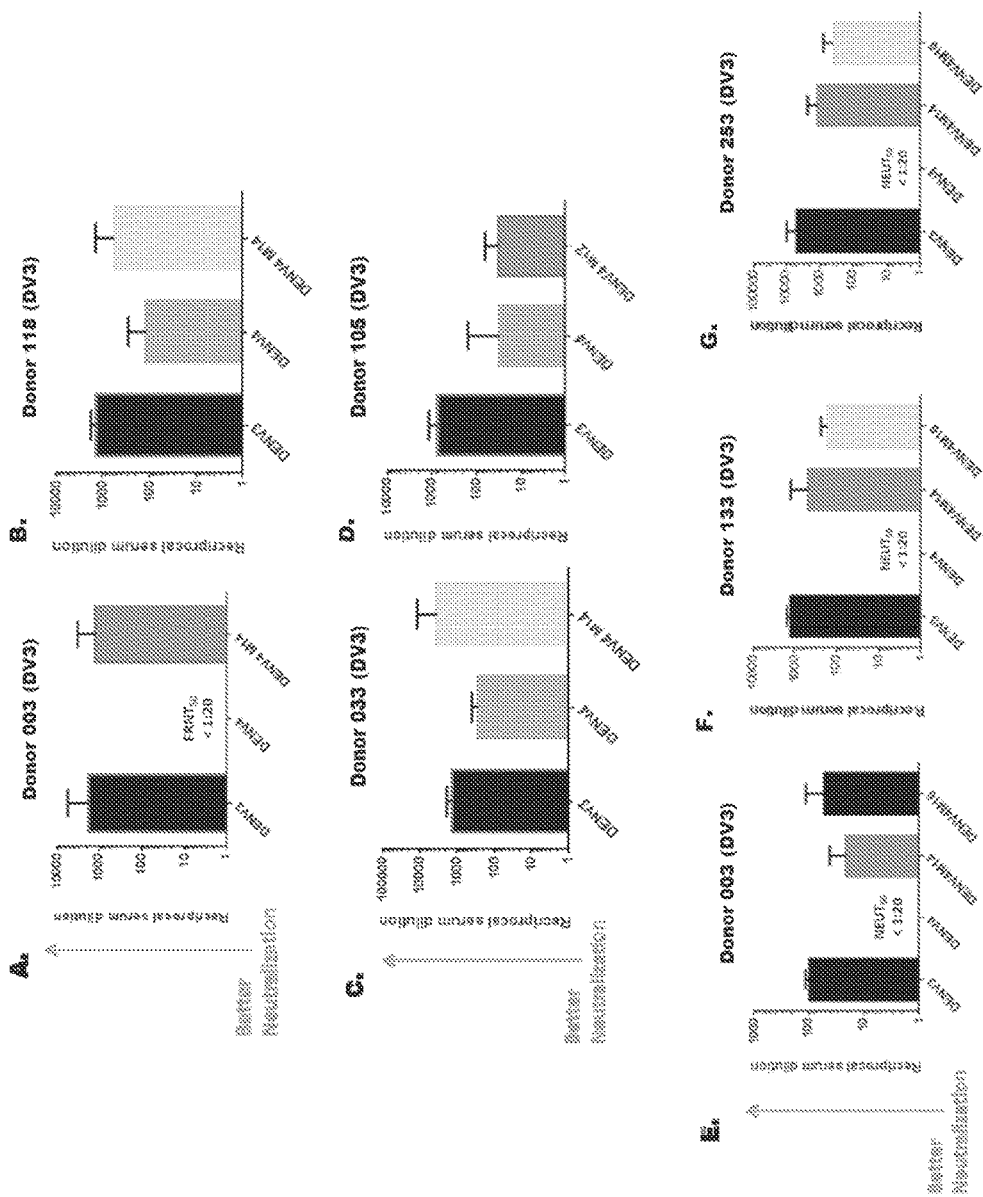
FIG. 5. Polyclonal DENV3 serum neutralization. (A-D) Sera collected from human donors recovered from primary DENV3 infection were assayed against DENV3, DENV4, DENV4 M12, and DENV4 M14 on Vero-81 cells to assess sensitivity to DENV3 humoral immune responses. (E-G) Sera collected from human donors recovered from primary DENV3 infection were assayed against DENV3, DENV4, DENV4 M14, and DENV4 M16 on U937-DC-SIGN cells to assess sensitivity to DENV3 humoral immune responses.

In order to assess sensitivity to polyclonal antibody neutralization of our rDENV4/3 panel, donor sera collected from convalescent patients following primary DENV infection was used in focus reduction (Vero-81) and flow cytometry-based (U937-DC-SIGN) assays. As with ELISA binding and 5J7 hmAb neutralization assays, DENV4 M12 did not demonstrate an increased sensitivity to neutralization by DENV3-specific sera in Vero cells (FIG. 5, Panel D). DENV4 M14, however, displayed a neutralization phenotype nearly identical to that of WT DENV3 and significantly greater than that of WT DENV4 (FIG. 5, Panels A-C) in Vero cells indicating that this rDENV4/3 virus had gained sensitivity to neutralization by polyclonal antibody responses generated by natural DENV3 infection in humans. Furthermore, this phenotype was confirmed in U937-DC-SIGN cells, and extended to DENV4 M16 (FIG. 5, Panels E-G) where for both rDENV polyclonal neutralization by DENV3 antisera was comparable to WT DENV3 while WT DENV4 was not neutralized at even the lowest serum dilution (1:20). Because of the small focus phenotype of DENV4 M16 on Vero cells, neutralization assays in this cell type were technically challenging and as such neutralization data for this rDENV is limited to U937-DC-SIGN, as the flow cytometry-based assay is easily performed on even attenuated viruses. Taken together these date indicate that DENV4 M14 and M16 have captured polyclonal determinants of DENV3 type-specific neutralization and demonstrate bivalency in neutralization sensitivity.

Figure 6:
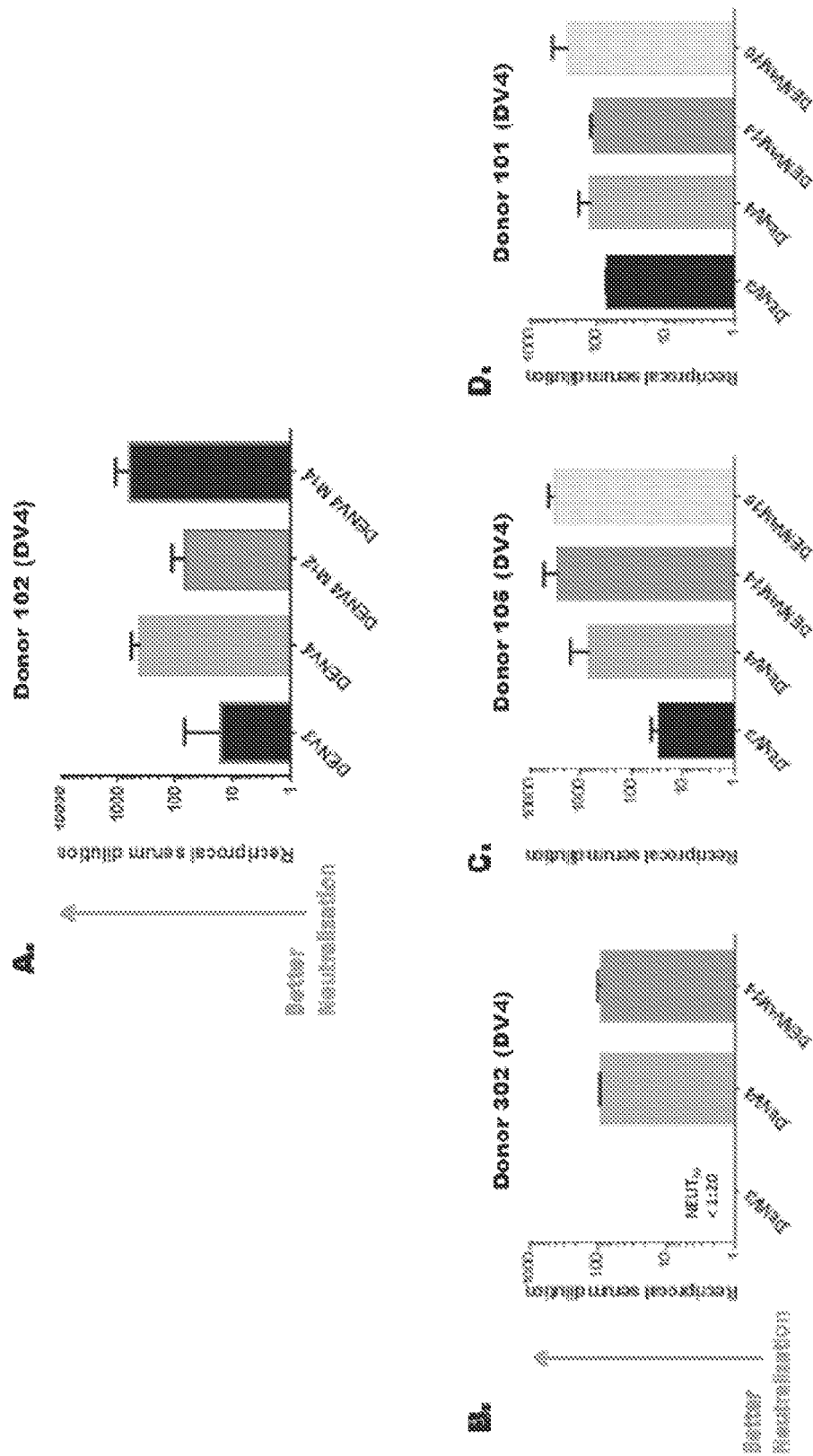
FIG. 6. Polyclonal DENV4 serum neutralization. (A) Sera collected from human donors recovered from primary DENV4 infection were assayed against DENV3, DENV4, DENV4 M12, and DENV4 M14 on Vero-81 cells to assess sensitivity to DENV4 humoral immune responses. (B-D) Sera collected from human donors recovered from primary DENV4 infection were assayed against DENV3, DENV4, DENV4 M14, and DENV4 M16 on U937-DC-SIGN cells to assess sensitivity to DENV4 humoral immune responses.

In addition to the gain of sensitivity to DENV3 polyclonal neutralization of our rDENV, we were interested in determining the retention and/or loss of DENV4 neutralization sensitivity of DENV4 M12, M14, and M16. To this end neutralization assays were performed in Vero (FIG. 6, Panel A) and U937-DC-SIGN (FIG. 6, Panels B-D) with sera collected from convalescent primary DENV4 patients. While DENV4 M12 demonstrated a slightly lower neutralization titer than WT DENV4 in Vero cells (FIG. 6, Panel A), DENV4 M14 and M16 had neutralization titers equal to or exceeding WT DENV4 in both cell types (FIG. 6, Panels A-D). This significant finding suggests that the determinants of type-specific neutralization for DENV3 and DENV4 are discreet elements on the E glycoprotein, and that determinant AA sequences of the 2 can be combined without altering each other. As such DENV4 M14 and M16 have the potential to be utilized as important reagents for both vaccine diagnostics or to guide the development of new and/or improved vaccine candidates.

rDENV4/3 Polyclonal Neutralization Sensitivity is Specific

Figure 7:
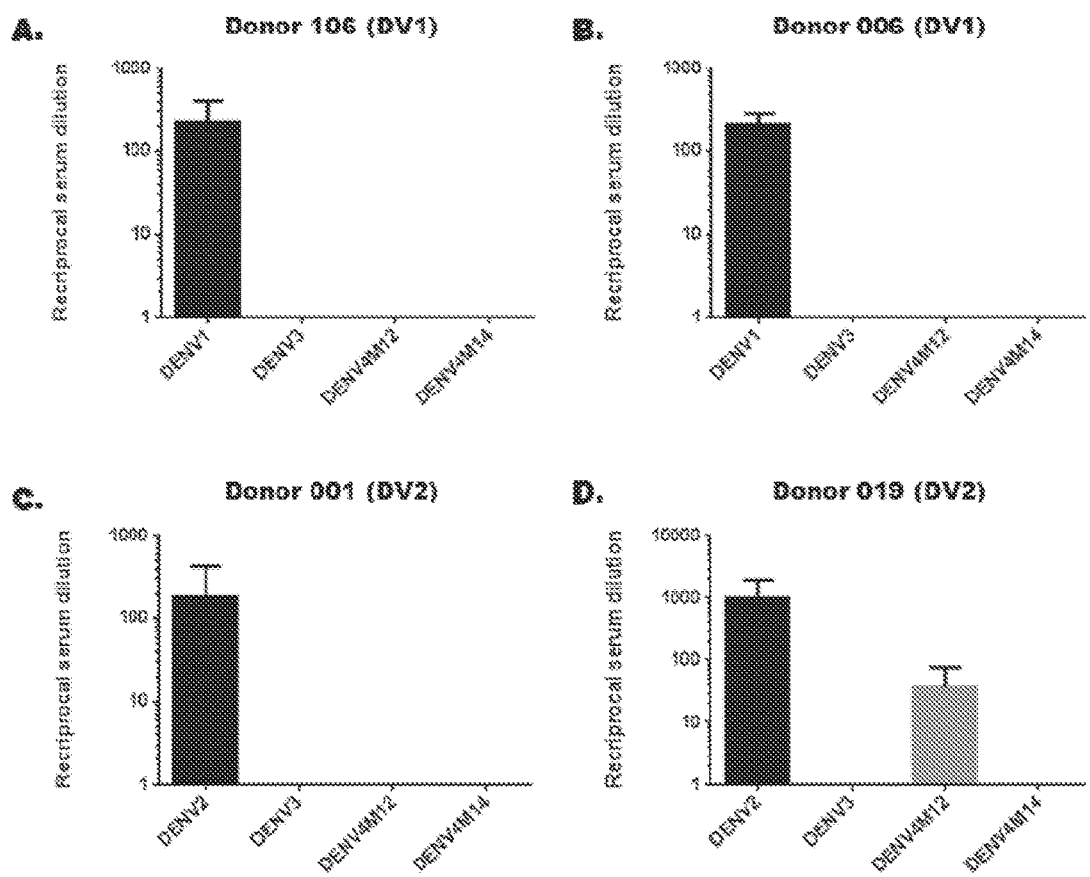
FIG. 7. Heterotypic serum neutralization. (A, B) Sera collected from human donors recovered from primary DENV1 infection were assayed against DENV1, DENV3, DENV4 M12, and DENV4 M14 on Vero-81 cells to assess sensitivity to non-specific humoral immune responses. (C, D) Sera collected from human donors recovered from primary DENV2 infection were assayed against DENV2, DENV3, DENV4 M12, and DENV4 M14 on Vero-81 cells to assess sensitivity to DENV4 humoral immune responses.

To eliminate the possibility that the panel of rDENV4/3 viruses had been modified in such a way as to increase their sensitivity to neutralization in a non-specific manner, neutralization assays with primary DENV1 and DENV2 sera collected from convalescent human patients were performed. Primary DENV1 sera were completely incapable of neutralizing either DENV4 M12 or M14 in Vero cells, in direct contrast to WT DENV1 which was neutralized to high levels (FIG. 7, Panels A-B). Additionally, DENV2 sera was also incapable of neutralizing DENV4 M14, although one sample tested did neutralize DENV4 M12, albeit at levels far lower than that of WT DENV2 (FIG. 7, Panels C-D). Taken together these results indicate that the gain of DENV3 neutralization sensitivity in the DENV4 background is specific for DENV3 and not the result of global structural changes that make the rDENV panel more sensitive to neutralization by heterotypic sera.

Example 3.

Development and Characterization of a Recombinant Dengue 2 Virus that Captures Type-Specific Neutralization Determinants of Both Dengue 1 and Dengue 2

Figure 8:
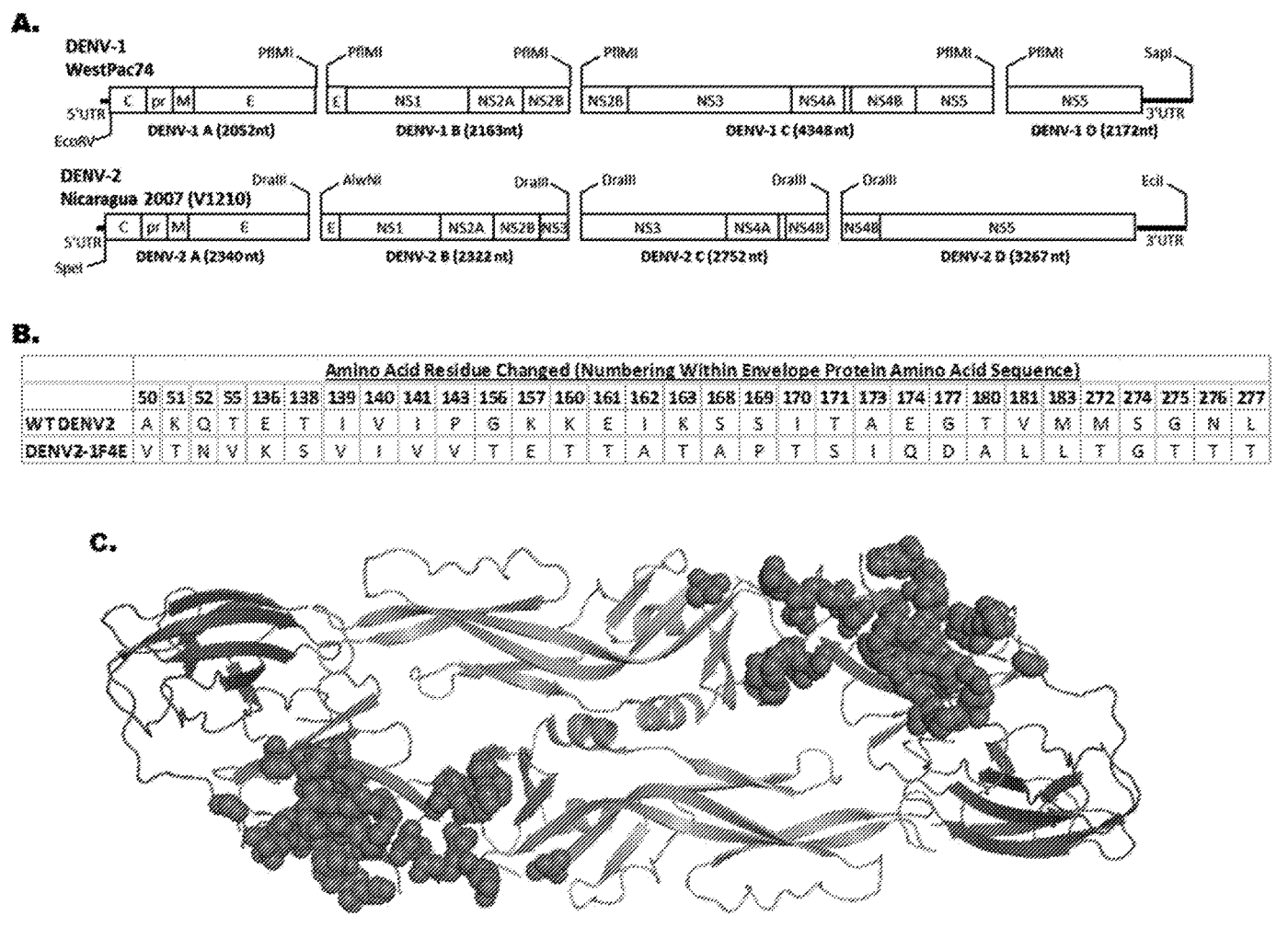

Development of a Reverse Genetics Platform for Recombinant DENV1 and DENV2 Generation We have previously described the generation and characterization of a reverse genetics system for production of recombinant DENV3 (rDENV3). Utilizing similar techniques we have developed a cDNA infectious clone (IC) system for DENV1 Western Pacific 1974 (WestPac74) along with a clinical isolate of DENV2 isolated from an epidemic in Nicaragua in 2007 (V1210). In order to circumvent instability and toxicity during bacterial plasmid amplification in *E coli*, both genomes were subcloned into 4 distinct fragments (FIG. 8, Panel A). Naturally occurring class IIs restriction endonuclease sites in the DENV1 genome at nucleotide (NT) position 2052 (PflMI; recognition sequence: CCACCTTTTGG, SEQ ID NO:9), 4215 (PflMI; CCACTAGCTGG, SEQ ID NO:10), and 8563 (PflMI; CCAAACCATGG, SEQ ID NO:11) were utilized to divide the genomic cDNA. Additionally, an EcoRV site in the bacterial vector and upstream of a T7 promoter sequence was used to generate the 5' end of the genome, while a SapI site in the vector was used for the 3' genomic end (FIG. 8, Panel A). For DENV2, the first genomic division was produced at position 2340 (DraIII between fragment A and vector; recognition sequence: CACTGTGTG). In order to preserve genomic sequence, a DraIII site (CACnnnGTG) was utilized for the 3' end of the A fragment, while an AlwNI (CAGnnnCTG) site was used for the 5' end of the B fragment. By mutating the endonuclease recognition sequence in the vector region of the recognition site (and not the DENV genomic sequence), the ligated product of these two restriction endonuclease digests preserves the native DENV2 genomic sequence without the introduction of mutations into the DENV genome to facilitate digestion. Additional genomic junctions at NT 4662 (DraIII; CACGTGGTG), and 7414 (DraIII; CACACTGTG) were utilized to divide the genomic cDNA. Additionally, a SpeI site in the bacterial vector and upstream of a T7 promoter sequence was used to generate the 5' end of the genome, while an EciI site in the vector was used for the 3' genomic end (FIG. 8, Panel A). Following bacterial amplification of plasmids containing genomic cDNA fragments, plasmids were digested with appropriate restriction endonucleases, purified by agarose gel electrophoresis, ligated with T4 DNA ligase, and transcribed with T7 RNA polymerase containing 5' cap analogue. In vitro transcribed RNAs were then electroporated into either Vero-81 or BHK-21 cells. Cells were cultured for 4-6 days at which time supernatants were collected, clarified by centrifugation, and passaged onto C6/36 (*Aedes albopictus*) cells for an additional 4 days. Supernatants were again collected and clarified, and titrated for use as working viral stocks. rDENV1 and rDENV2 demonstrated phenotypic properties (growth kinetics, peak infectious titers, and infectious focus morphology/size) identical to that of the parental natural isolate (data not shown).

Transplantation of a Strongly Neutralizing DENV1 mAb Epitope into DENV2 IC

Figure 9:
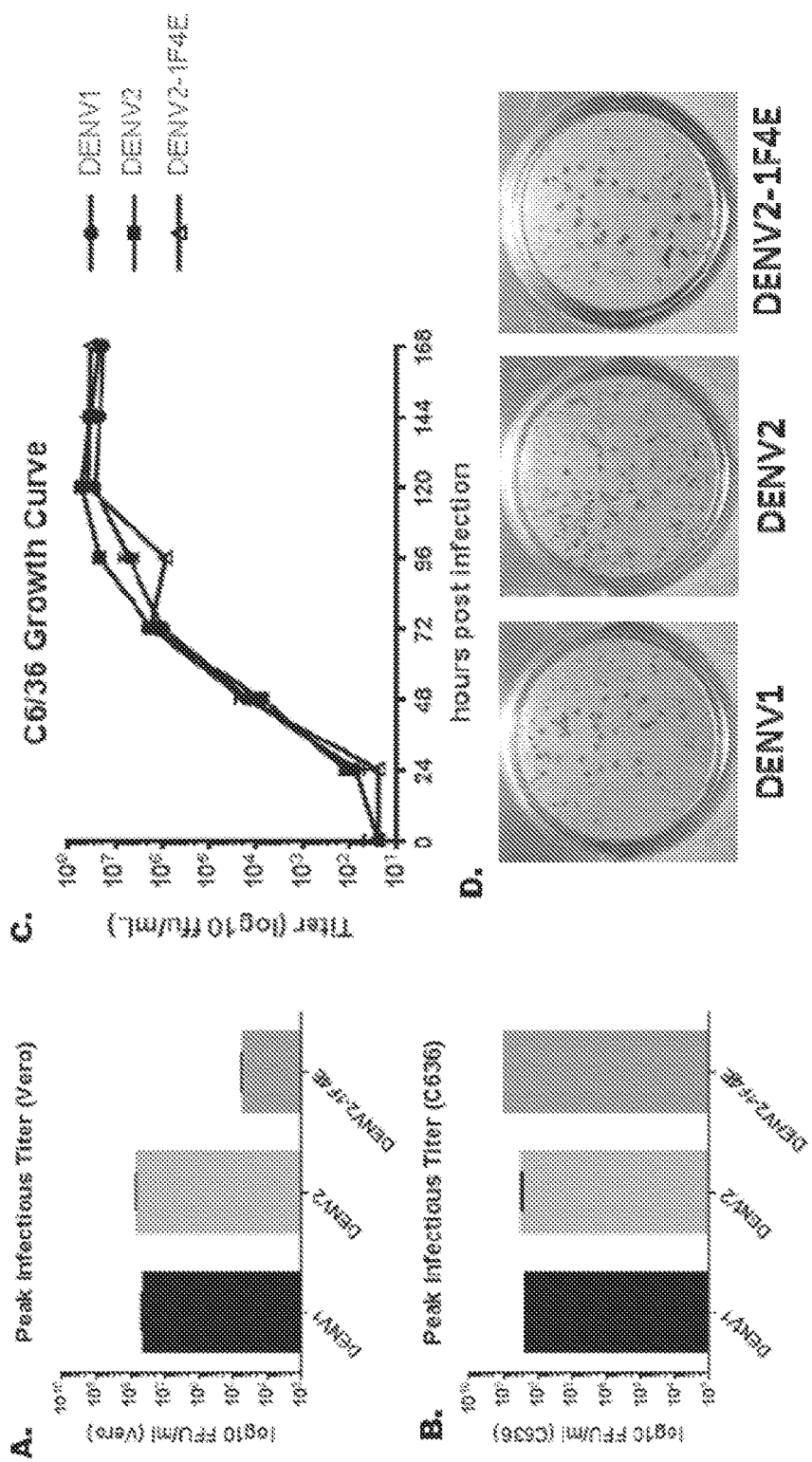
FIG. 9. Growth characteristics of rDENV2/1. DENV1, DENV2, and DENV2-1F4E were propagated on C6/36 cells until maximal cytopathology was observed (typically 4 days post-inoculation) and harvested for titration on Vero-81 (A) or C6/36 (B) cells. Infectious titers are presented as ffu/ml cell culture supernatant. (C) Multi-step growth curve analysis of DENV1, DENV2, and DENV2-1F4E inoculated on C6/36 cells at an MOI=0.01. Cell culture supernatants were titrated on C6/36 cells as described. (D) Infectious foci size and morphology of WT and DENV2-1F4E viruses on C6/36 cells.

Previous studies have identified a strongly type-specific human monoclonal antibody (hmAb) specific for DENV1 (1F4). Utilizing the crystal structure of this mAb bound to DENV1, and the contact amino acid (AA) residues identified, we sought to transplant the AA residues encompassing this epitope from DENV1 into DENV2 using our novel reverse genetics platform. Following AA and NT alignments between DENV1 and DENV2, interserotypic variant AA were identified and selected for transplantation from DENV1 into DENV2. NT sequences in the DENV2 IC were modified to facilitate AA changes to match DENV1 (FIG. 8, Panels B-C), and subgenomic cDNAs capturing these changes were synthesized (BioBasic; Amherst, N.Y.). rDENV were generated as described above, and recovered virus used for phenotypic characterization. This rDENV has been designated DENV2-1F4E (FIG. 8, Panels B-C).

rDENV2/1 Viruses are Viable and Demonstrate Distinct Fitness Characteristics In Vitro rDENV2/1 was successfully recovered following electroporation and subsequent passage on C6/36 cells. Peak infectious titers from C6/36 cells were measured and found to be comparable to that of the parental WT DENV1 and DENV2 IC on C6/36 cells (FIG. 9, Panel B), although highly attenuated (approximately 3 $\log_{10}$) on Vero cells (FIG. 9, Panel A). Fitness analyses were carried out on C6/36 mosquito cells, with multi-step growth curves (MOI=0.01) (FIG. 9, Panel C). In general, no significant fitness defects were seen at early time points (<96 hr; post-inoculation (hpi)). DENV2-1F4E Showed a drop in titer at 96 hpi however this was an isolated lag as by 120 hpi and beyond titers were equivalent to WT DENV 1 and 2 (FIG. 9, Panel C). Cell health could have played a role in this isolated attenuated time point and as such further investigation is required. These data do, however, indicate that DENV2-1F4E does not demonstrate significant growth attenuation in arthropod cells as compared to WT DENV1 and 2. Correspondingly to growth kinetic data, DENV2-1F4E (FIG. 9D) does, Panel not show a substantial difference in size or morphology of infectious foci as compared to WT DENV1 or 2. These data indicate that rDENV2-1F4E containing a transplanted region of DENV1 is viable and demonstrates suitable growth characteristics for further characterization.

hmAb 1F4 Binds rDENV2/1

Figure 10:
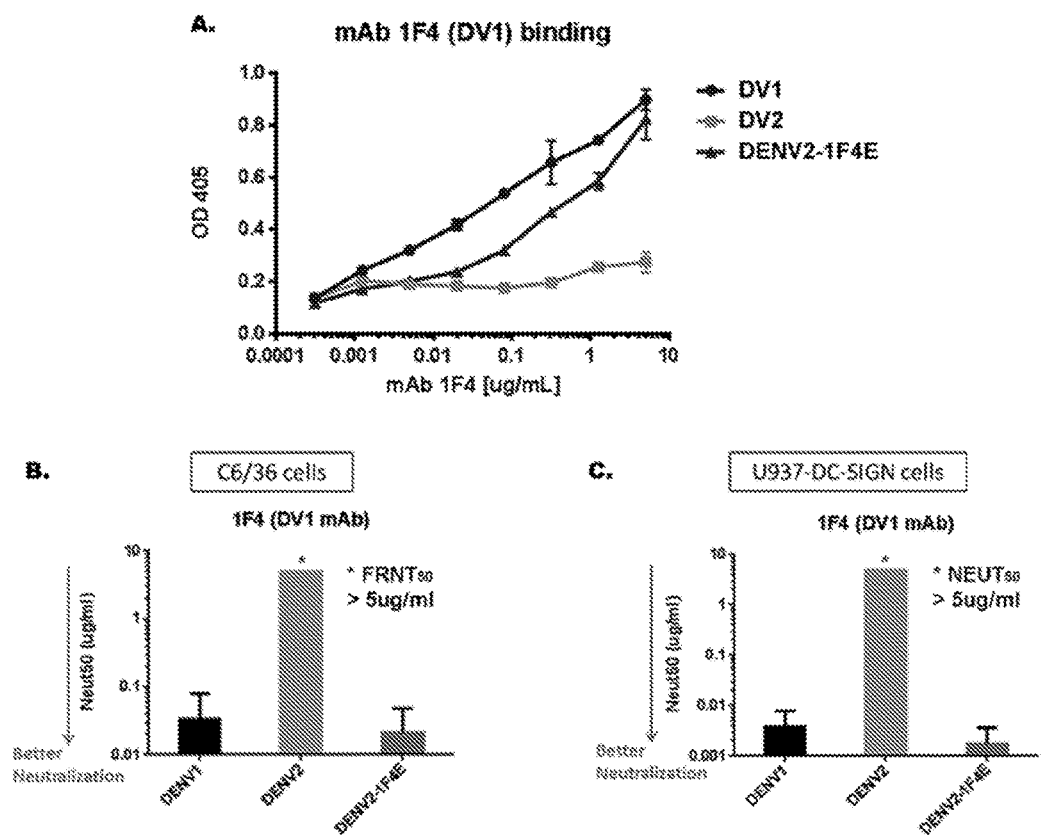
FIG. 10. Binding and neutralization of hmAb 1F4 on rDENV2/1 (A) ELISA OD values for DENV1-specific hmAb 1F4 on DENV1, DENV2, and DENV2-1F4E. Neutralization assays on C6/36 (B) and U937-DC-SIGN (C) for DENV1, DENV2, and DENV2-1F4E. Data presented as μg/ml required to neutralize 50% of viral infectivity.

Assays were performed to determine the level to which the epitope for hmAb 1F4 was transplanted from DENV1 into DENV2 in DENV2-1F4E. ELISAs were undertaken to assess binding of the DENV1-specific hmAb 1F4 to both WT and rDENV viruses. These revealed that 1F4 bound WT DENV1, but not DENV2, consistent with previous data. Interestingly, 1F4 bound DENV2-1F4E at levels comparable to WT DENV1 (FIG. 10, Panel A). These data indicate that residues identified in the crystal structure of 1F4 bound to DENV1 are sufficient to transplant monoclonal Ab binding between DENV1 and 2. As a corollary to these binding studies, virus neutralization assays were performed using 1F4 and DENV2-1F4E. In agreement with the ELISA binding data, DENV2-1F4E was neutralized by 1F4 at Ab concentrations comparable to that of WT DENV1 (FIG. 10, Panels B-C). Significantly, these results were consistent 2 distinct cell lines (C6/36 and U937 expressing DC-SIGN).

rDENV2/1 has Bivalent Sensitivity to Polyclonal Serum Neutralization

Figure 11:
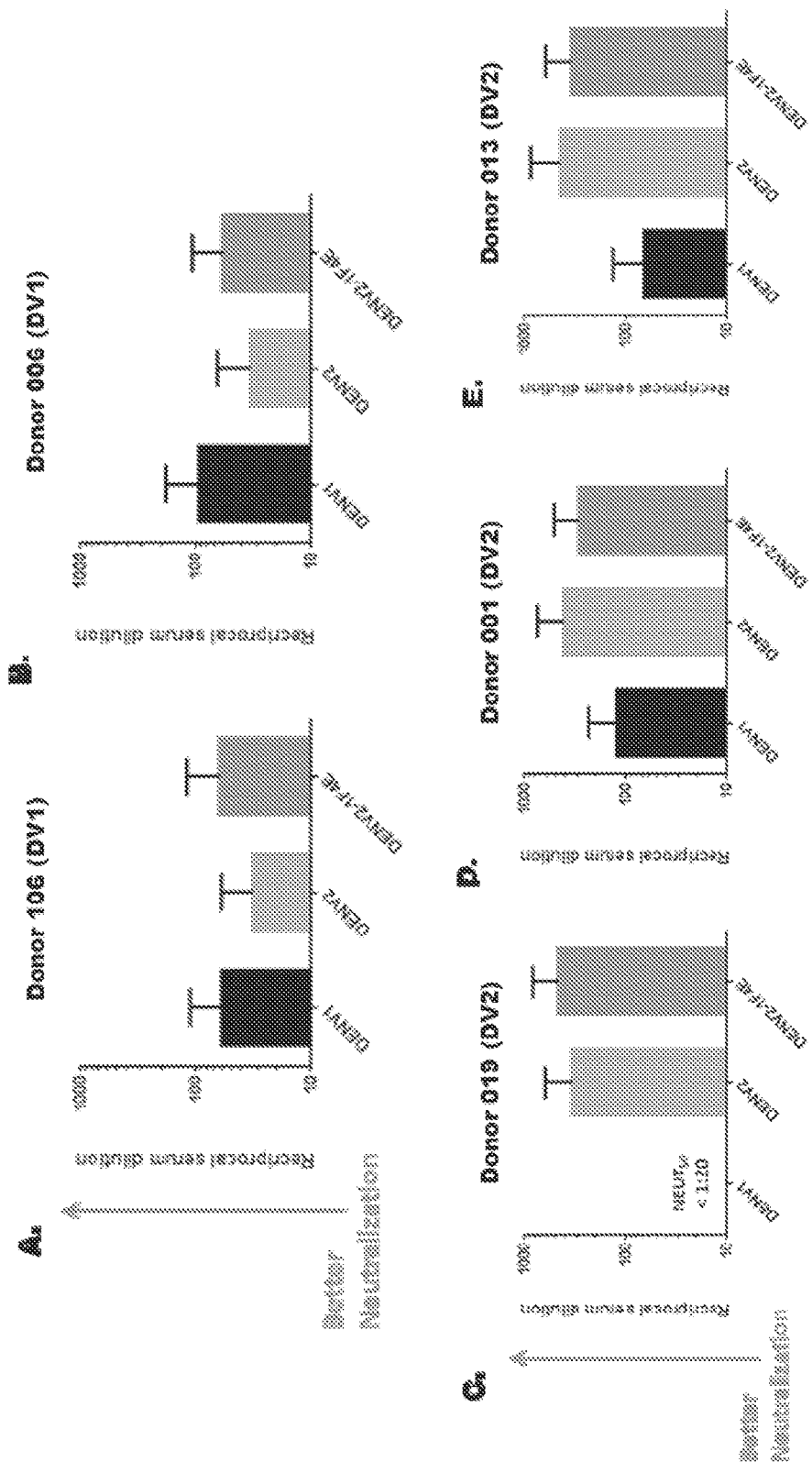
FIG. 11. Polyclonal DENV1 and DENV2 serum neutralization. (A and B) Sera collected from human donors recovered from primary DENV1 infection were assayed against DENV1, DENV2, and DENV2-1F4E on U937-DC-SIGN cells to assess sensitivity to DENV1 humoral immune responses. (C-E) Sera collected from human donors recovered from primary DENV2 infection were assayed against DENV1, DENV2, and DENV2-1F4E on U937-DC-SIGN cells to assess sensitivity to DENV2 humoral immune responses.

In order to assess sensitivity to polyclonal antibody neutralization of our rDENV2/1 virus, donor sera collected from convalescent patients following primary DENV1 infection was used in flow cytometry-based (U937-DC-SIGN) assays. Because of the small focus phenotype of DENV2-1F4E on Vero cells, neutralization assays in this cell type were technically challenging and as such neutralization data for this rDENV is limited to U937-DC-SIGN, as the flow cytometry-based assay is easily performed on even attenuated viruses. As with ELISA binding and 1F4 hmAb neutralization assays, DENV2-1F4E displayed a neutralization phenotype nearly identical to that of WT DENV1 and significantly greater than that of WT DENV2 in U937-DC-SIGN cells (FIG. 11, Panels A-B), indicating that this rDENV2/1 virus had gained sensitivity to neutralization by polyclonal antibody responses generated by natural DENV1 infection in humans. These data along with the hmAb 1F4 data indicate that DENV2-1F4E captured polyclonal determinants of DENV1 type-specific neutralization and demonstrates bivalency in neutralization sensitivity.

In addition to the gain of sensitivity to DENV1 polyclonal neutralization of our rDENV, we were interested in determining the retention and/or loss of DENV2 neutralization sensitivity of DENV2-1F4E. To this end neutralization assays were performed in U937-DC-SIGN (FIG. 11, Panels C-E) with sera collected from convalescent primary DENV2 patients. Significantly, DENV2-1F4E had neutralization titers equal to or exceeding WT DENV2 in all cases. This finding suggests that the determinants of type-specific neutralization for DENV1 and DENV2 are discreet elements on the E glycoprotein, and that determinant AA sequences of the 2 can be combined without altering each other. As such DENV2-1F4E has the potential to be utilized as important reagents for both vaccine diagnostics or to guide the development of new and/or improved vaccine candidates.

rDENV2/1 is Attenuated in a Murine Model of DENV Pathogenesis

Figure 12:
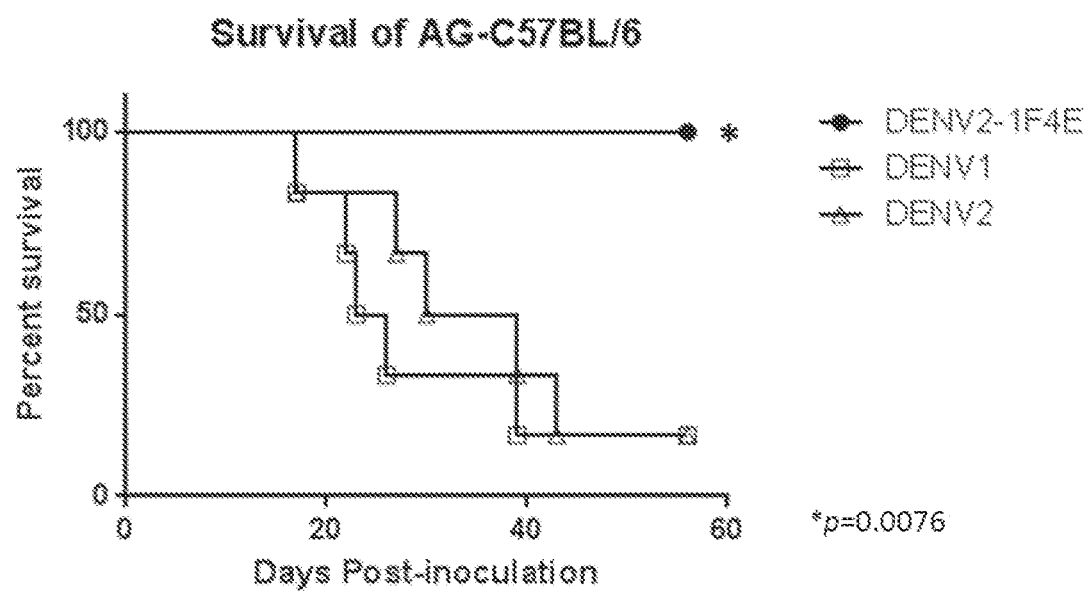
FIG. 12. Murine survival. Interferon α/β/γ deficient mice on a C57BL/6 background were inoculated intraperitoneally with 3.3×10$^6$ ffu DENV1, DENV2, or DENV2-1F4E. Mice were monitored for weight loss and clinical illness for 56 days.

In order to assess the level of attenuation of our chimeric rDENV, we compared lethality of DENV2-1F4E to its parental WT DENV1 and DENV1 in an immunocompromised mouse model of DENV disease. C57BL/6 deficient in both the interferon α/β receptor and the interferon γ receptor were inoculated intraperitoneally with $3.3 \times 10^6$ ffu (C6/36 titer) of DENV1, DENV2, or DENV2-1F4E. Mice were weighed and monitored for 56 dpi until termination of the study. As shown in FIG. 12, while mice inoculated with WT DENV1 and DENV2 displayed a >80% mortality rate, no mice receiving an equivalent dose of DENV2-1F4E succumbed to infection (p=0.0076) demonstrating a high degree of attenuation for this rDENV. These data indicate that chimerization of DENV to generate bivalent viruses introduces a level of in vivo attenuation that may be suitable for vaccine development.

Example 4.

Use of Chimeric Recombinant Dengue Virus to Map the Serotype 2 Neutralizing Human Antibody Response Dengue virus (DENV; DV) is the most significant human arboviral pathogen worldwide with an estimated 390 million infections and 96 million symptomatic cases annually. Nearly half the global population is at risk of disease, yet there are no licensed vaccines or therapeutics to treat or prevent dengue disease. Dengue infection can manifest as dengue fever, a self-limiting febrile illness characterized by severe bone and joint pain, or more severe forms known as dengue hemorrhagic fever and dengue shock syndrome which are punctuated by improper clotting, vascular leakage, and in the most severe instances multiple organ failure that is typically fatal. Dengue virus exists as four distinct serotypes, and infection with one serotype does not confer protection from subsequent infection with others. In fact, immunity to a single dengue serotype is associated with an increased risk of severe disease upon infection with another serotype, a confounding factor for vaccine design. Traditional vaccination strategies have utilized a cocktail of four distinct viruses to elicit equivalent immune responses to each serotype, however none to date have consistently achieved this goal. As such there is a desperate need for diagnostic tools to aid our understanding of the complex immune response to dengue infection, and for new technologies to guide and produce new vaccine designs. This invention report describes the generation of a panel of novel recombinant chimeric dengue viruses containing critical antigenic components of heterologous serotypes that can be used to characterize human antibody responses to multiple serotypes and also to generate new multivalent vaccine candidates capable of eliciting immune responses to multiple serotypes within the context of a single virus inoculum. We believe that this strategy of antigen transplantation is compatible with multiple vaccine platforms for other human and animal pathogens, and importantly, represents a major breakthrough in dengue virus vaccine development.

Generation of rDENV4/2 Virus

To identify amino acids residues that differ between DENV2 and DENV4, amino acid sequences of the envelope domain III (EDIII) region (amino acid positions 296-395) were aligned (FIG. 13, Panel A). Residues differing between DENV2 and DENV4 were highlighted, 40 total, and those residues from DENV4 were replaced with those from DENV2 by making the fewest nucleotide changes as possible. The 40 differing amino acids span the entire EDIII, including surface exposed residues, internal residues, and residues on the edges of the domain, likely which interact with other monomers, and dimers (FIG. 13, Panel B). Generation of recombinant virus utilizes four-fragment cloning strategy used to create parental wild-type viruses. DENV-4 A plasmid cassette contains envelope glycoprotein, with EDIII highlighted in grey (FIG. 13, Panel C). Using DENV-4 B, C, and D plasmid cassettes with recombinant DENV-4 A, DV4-EDIII-DV2 virus can be generated. Of 40 amino acid changes introduced into the recombinant virus, 14 of the amino acids introduce a change of charge (Table 1). Six residues increase negative charge, and eight residues introduce a more positive charge.

Recombinant Virus has Similar Maturation Profile to Parental DENV4

Immunoblotting was performed on virus to measure ratio of E and prM proteins present on virus (FIG. 14). DENV2 shows high levels of prM relative to E, indicating a highly immature virus, due to either incomplete furin processing or prM dissociation. Both DENV4 and DV4-EDIII-DV2 have no detectable prM, suggesting these viruses are highly mature. However, because of significant differences in amount of E protein detected between DENV2 and the 2 DENV4 backboned viruses, we cannot preclude to presence of some prM on the surface of these virions.

Recombinant Virus is Attenuated in Vero Cells, but not Mosquito Cells

Upon examination using a multi-step growth curve, DV4-EDIII-DV2 is has a 2 $\log_{10}$ growth attenuation in Vero cells compared to both DENV2 and DENV4 parental viruses (FIG. 15, Panel A). DV4-EDIII-DV2 forms infectious foci in Vero cells, with a morphology between both parental viruses (FIG. 1, Panel 5B). Despite 1-2 additional days of infection in Vero cells, DV4-EDIII-DV2 foci do not reach the size of parental virus foci.

Despite the growth attenuation in Vero cells, DV4-EDIII-DV2 shows no attenuation in C6/36 cells (FIG. 16, Panel A). As observed in Vero cells, DV4-EDIII-DV2 C6/36 infectious foci display a morphology between both parental viruses. With an additional 1-2 days of infection, these foci reach a comparable size to both wild-type viruses.

Transplantation of DENV2 EDIII, is Sufficient to Transfer 2D22 Binding and Neutralization 2D22 is a human monoclonal antibody (MAb) that is highly type-specific for DENV2 (FIG. 17, Panel A). Previously, an escape mutant was generated by passaging DENV2 in the presence of 2D22 in Vero cells. This escape mutant has one point mutation, R323G, in the middle of EDIII (FIG. 17, Panel B), indicating this region of DENV E may be included in the 2D22 epitope. ELISA binding shows DV4-EDIII-DV2 has gained partial binding to 2D22, above DV4 levels, but not to DV2 levels (FIG. 17, Panel C). Binding to 2J20 (FIG. 17, Panel D) a cross-reactive DENV MAb, shows comparable levels of virus are present in binding assay, and that DV4-EDIII-DV2 morphology is maintained.

Neutralization by 2D22 was analyzed using two cell types and two assays. Vero-81 cells were infected in the presence of 2D22, and the amount of antibody required to neutralize 50% of foci ($FRNT_{50}$) was calculated. DENV2 requires ~0.1 ng/ul of 2D22 to neutralize 50% of virus, whereas DENV4 is not neutralized at the maximum concentration of antibody used, 5 ng/ul (FIG. 17, Panel E). Transplantation of EDIII is sufficient to transfer sensitivity to neutralization by 2D22, as can be seen by the ~0.01 ng/ul $FRNT_{50}$ value. These results are confirmed using the U937+DC-SIGN flow-cytometry based neutralization assay (FIG. 17, Panel F), which measures neutralization by a reduction in the number of cells infected in the presence of antibody. These data further suggest that 2D22 contains EDIII as part of its epitope.

DV4-EDIII-DV2 has Gained Sensitivity to Neutralization by Additional DENV2 MAbs

A panel of 6 additional DENV2 MAbs was used to further characterize DV4-EDIII-DV2 (Table 2). Many of these MAbs do not bind recombinant EDIII (rEDIII), including 2D22, which we have shown contains EDIII as part of its epitope (FIG. 17). It is possible that 2D22 uses a complex epitope, only present in entire E monomers, E dimers, or complete virus structures, explaining the lack of binding to rEDIII alone. It is possible other MAbs in this panel have the same requirements. Additional information such as residues important for binding, determined by either generating escape mutants, or through alanine scanning mutations, is included in the table.

One point mutation was generated for DVC3.7, V382G, which maps to the lateral ridge of EDIII (FIG. 18, Panel A). DV4-EDIII-DV2 is sensitive to neutralization by DVC3.7, similar to DENV2, whereas parental DENV4 is not (FIG. 18, Panel C). One point mutation was generated for DVC10.16, E311K, which maps to the A-strand of EDIII (FIG. 18, Panel B). As seen with DVC3.7, DV4-EDIII-DV2 gains neutralization to DVC10.16, from the parental DENV4, below levels required for DENV2 neutralization. Scanning alanine mutagenesis revealed positions 101 and 108 of the fusion loop in EDII, to be required for DVC13.6 binding (FIG. 18, Panel E). DV4-EDIII-DV2 is neutralized by DVC13.6 (FIG. 18, Panel F). These data suggest that the DVC13.6 DENV2 epitope could span from EDIII into the fusion loop region of EDII. Two additional MAbs neutralize DV4-EDIII-DV2 similar to DENV2 and not DENV4 (FIG. 18, Panels G-H). Surprisingly, 3F9 which binds rEDIII (Table 2), does not bind or neutralize DV4-EDIII-DV2, despite the transplanted domain (FIG. 18, Panel I). This suggests that 3F9's epitope requires EDIII, but perhaps additional residues outside of EDIII, present only in DENV2, and not DV4-EDIII-DV2.

DV4-EDIII-DV2 Loses Neutralization to DENV4 EDIII Specific MAb

DV4-E88 is a mouse DV4 type-specific MAb with a known EDIII epitope and specific residues, 331 and 361, mapped through escape mutants (Table 2 and FIG. 19, Panel A). As expected, DV4-E88 neutralizes DV4 and not DV2. Because EDIII of DENV4 was replaced with that from DENV2, DV4-EDIII-DV2 neutralization by DV4-E88 was lost.

DV4-EDIII-DV2 Gains Neutralization to DENV2 Polyclonal Immune Sera

Figure 22:
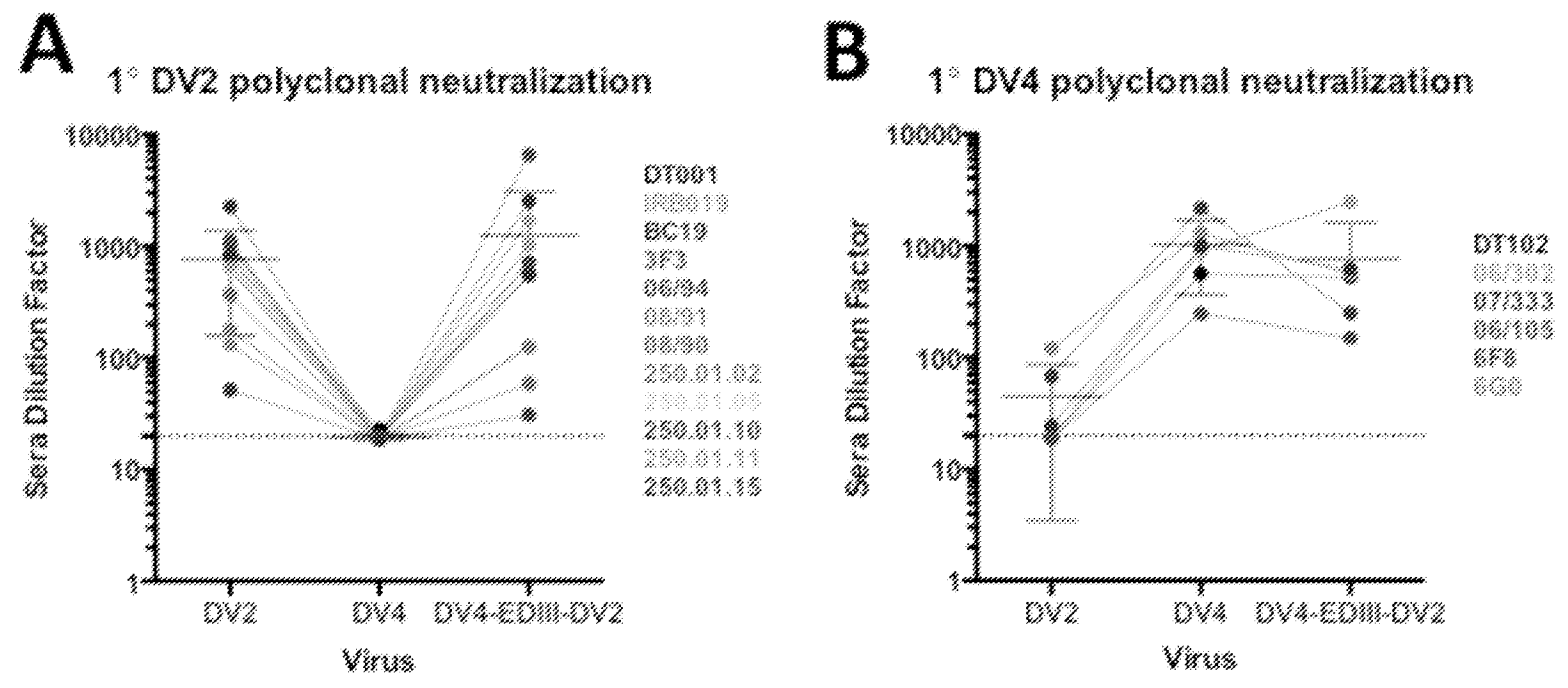

To test if antibodies present in polyclonal immune sera recognize EDIII, twelve DENV2 polyclonal immune sera were tested against DV4-EDIII-DV2 (FIG. 20, Panels A-L). DV4-EDIII-DV2 gains sensitivity to neutralization by DENV2 sera, comparable to that of DENV2. DENV4 is not neutralized by any of the sera at the highest tested concentration. Despite the range in neutralization titers with the different sera (ranging from ~50 to ~3,000) the average DV4-EDIII-DV2 neutralization titer is higher than DENV2 (FIG. 22, Panel A).

DV4-EDIII-DV2 Preserves Neutralization to DENV4 Polyclonal Immune Sera

Figure 21:
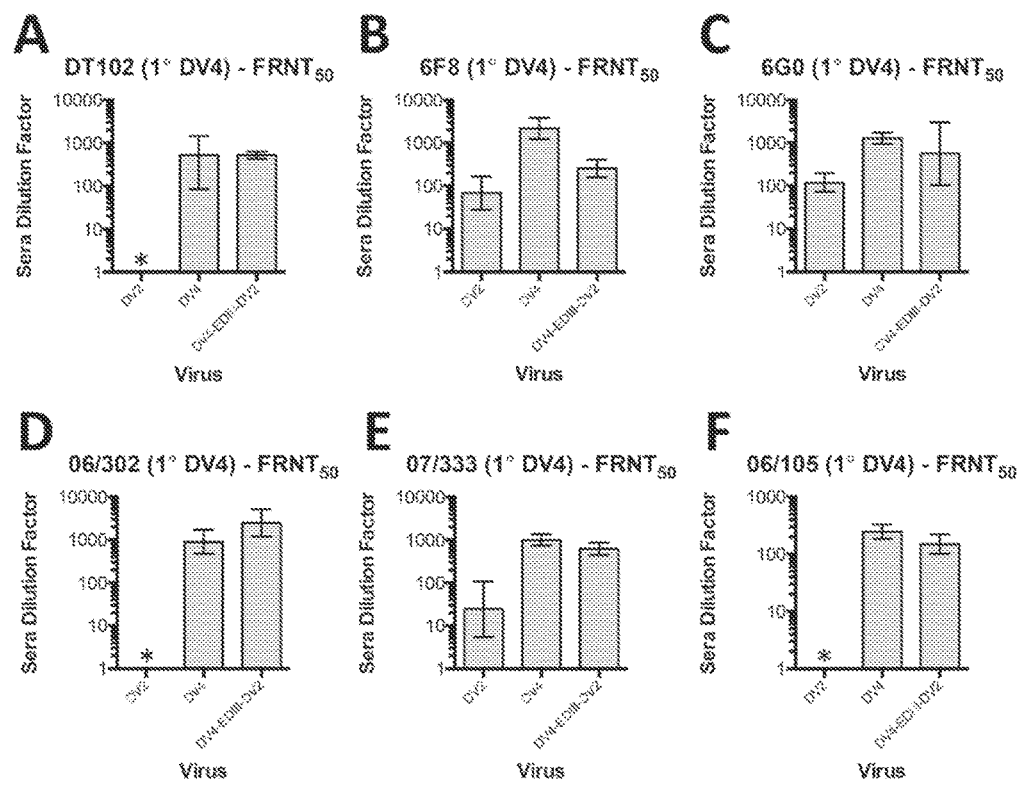

DENV4 polyclonal immune sera neutralizes DV4-EDIII-DV2 with neutralization titers similar to that of DENV4 (FIG. 21, Panels A-F). These data suggest that the major DENV4 neutralizing epitope is distinct from DENV2, and is not disrupted when DENV2 EDIII is introduced into DENV4. As seen with DENV2 polyclonal immune sera, DV4-EDIII-DV2 average neutralization titer is comparable to that of DENV4 (FIG. 22, Panel B).

DV4-EDIII-DV2 does not Gain Neutralization to Heterotypic Polyclonal Immune Sera To test if DV4-EDIII-DV2 is neutralized by heterotypic DENV1 or DENV3 polyclonal immune sera, the same FRNT assay was performed using sera from convalescent DENV1 and DENV3 donors. While in some cases DV4-EDIII-DV2 gains slight sensitivity to neutralization above levels of parental DENV4 neutralization titers, it does not exceed levels of DENV2 neutralization, and is in each case substantially lower than homotypic neutralization (FIG. 23, Panels A-B).

DV4-EDIII-DV2 appears to identify the major DENV2 type-specific neutralizing epitope to be a quaternary epitope containing EDIII. This recombinant virus gains neutralization to DENV2 polyclonal immune sera, without losing sensitivity to DENV4 sera, suggesting DENV4 has a different neutralizing epitope. This virus can be used as a diagnostic tool to probe for either DENV2 or DENV4 antibodies. In particular because of the isolation of the DENV2 EDIII in the heterogenous DENV4 background, relative abundance of EDIII-specific Abs from naturally infected or vaccinated individuals can be assayed. This is significant in light of our finding that EDIII of DENV2 appears to be critical for type-specific neutralizing responses after infection. This virus contains domains from both DENV2 and DENV4, and is sensitive to neutralization by both DENV2 and DENV4 antibodies, suggesting this virus might be useful as a bivalent vaccine capable of eliciting antibody responses against both serotypes. Furthermore, a tetravalent vaccine formulation may be achievable if used in concert with DENV1/3 or DENV3/1 recombinant viruses, demonstrating a significant advance in the dengue vaccine field.

Virus Construction

Recombinant viruses are constructed using a four-fragment cloning strategy, the same strategy used to create wild-type DENV infectious clones. DENV-4 genome is subcloned into four separate DNA plasmids. T7 promoter was introduced into the 5' end of the A fragment, and unique type IIS restriction sites are introduced into the 5' and 3' end of each fragment. These restriction sites ensure plasmids will only be assembled in the correct direction to generate DENV genomic sequence.

The EDIII residues from DENV2 were introduced into DENV4, by replacing nucleotides in DENV4 A fragment, with nucleotides encoding for DENV2 amino acids. The new A fragment with nucleotides from DENV2, was synthesized and inserted into pUC-57 plasmid (BioBasic). The new A plasmid, in addition to DENV4 B, C and D plasmids were grown in E. coli, purified, digested with corresponding type IIS restriction enzymes, ligated using T4 DNA ligase to create full length cDNA dengue viral genome. cDNA was transcribed using T7 polymerase. Recombinant RNA was electroporated into BHK-21 cells and cell culture supernatant containing viable virus was harvested. Virus was then passaged two times on C6/36 cells, centrifuged to removed cellular debris, and stored at $-80°$ C.

Cells

Mosquito Ae. albopictus C6/36 cells were grown in MEM (Gibco) media at $32°$ C. Vero-81 cells were maintained in DMEM at $37°$ C. The human monocyte lymphoma cell line U937, stably expressing DC-SIGN (U937+DC-SIGN) via retroviral transduction was maintained in RPMI-1640 (Gibco) at $37°$ C. and supplemented with 50 mM $\beta$-mercaptoethanol. Media was supplemented FBS (10% for Vero-81 and U937+DC-SIGN cells, 5% for C6/36), which was lowered to 2% to make infection media. All media were additionally supplemented with 100 U/ml penicillin and 100 mg/ml streptomycin. U937+DC-SIGN was additionally supplemented with 0.1 mM nonessential amino acids, and 2 mM glutamine. All cells were incubated in 5% $CO_2$.

Binding ELISA

Equal quantities of virus (as previously titrated by ELISA) were captured using anti-E antibodies. The primary antibodies 2D22 and 2J20 were diluted fourfold starting to generate dilution series Alkaline phosphatase-conjugated secondary antibodies were used to detect binding of primary antibodies with P-nitrophenyl phosphate substrate, and reaction color changes were quantified using spectrophotometry.

DENV Immune Sera

Human DENV immune sera were collected from individuals with confirmed previous natural DENV infections. Additional human immune sera were collected from individuals given DENV vaccines. Non-human primate immune sera were collected following DENV infection.

Virus Titration and Focus Reduction Neutralization Test (FRNT)

One day prior to infections, 24-well plates were seeded with either $5 \times 10^4$ Vero-81 or $1 \times 10^5$ C6/36 cells. Prior to infection, growth media was removed. Virus titrations were performed by serially diluting virus stocks 10-fold, then incubated for 1 hr at $37°$ C. After incubation, virus dilutions were added to cells for 1 hr at $37°$ C., then overlaid with 1 ml 1% methylcellulose in OptiMEM (Gibco), supplemented with 2% FBS, 100 U/ml penicillin and 100 mg/ml streptomycin. After 3-6 days incubation at $37°$ C., overlay was removed, cells were washed with PBS and fixed in 80% methanol. Plates were blocked with 5% instant milk made in PBS, then incubated with anti-E MAb 4G2 and anti-PrM MAb 2H2, both diluted 1:500 in blocking buffer. Plates were then washed, and incubated with HRP-conjugated goat anti-mouse Ab (Sigma), diluted 1:2500 in blocking buffer. Plates were then washed, and foci were developed with TrueBlue HRP substrate (KPL), and foci were counted.

For FRNT assay, either MAbs or sera were diluted four-fold and mixed with ~40 FFUs virus, then incubated for 1 hr at $37°$ C. After incubation, virus and MAb/sera dilutions were added to cells for 1 hr at $37°$ C., then overlay was added and processed as above.

Growth Curves

Either Vero or C6/36 cells were infected at a multiplicity of infection (MOI) of 0.01. Every 24 hrs culture supernatant was harvested, and centrifuged to remove cellular debris. Samples were frozen at $-80°$ C. until use. Fresh media was replaced each day. Viruses were tittered on their propagating cell type as described above.

U937+DC-SIGN Neutralization Assay

As in FRNT assay, virus is diluted in U937+DC-SIGN infection media and mixed with four-fold dilution series of MAb. Virus and MAb mixture were incubated for 1 hr at $37°$ C. Virus and Mab mixture was then added to 5×10⁴ U937+ DC-SIGN cells per well of 96-well round bottom plate and incubated for 2 hr at 37° C. After incubation, cells were centrifuged and washed twice with infection media, then resuspended in growth media. One day post infection, cells were centrifuged to collect, washed with PBS and fixed with 4% paraformaldehyde. Cells were then permeabilized and blocked in 1% normal mouse sera. Cells were stained with 1:400 dilution of anti-E 2H2 directly labeled with Alex Fluor 488. Percentage of positively staining cells was measured Guava easyCyte Flow Cytometer (Millipore).

Immunoblotting

Virus stocks were diluted in PBS, mixed with 4× Laemmli Sample Buffer (Bio-Rad), and heated for 10 minutes at 50° C. Samples were run on 12% PROTEAN TGX Gels (Bio-Rad), transferred to PVDF membrane and blocked in 5% instant milk in PBS+0.05% Tween overnight at 4° C. Membranes were probed with 0.5 ug/ml anti-E 4G2, 0.5 ug/ml anti-PrM 2H12 and 5L20 in blocking buffer for 2 hr at 37° C. After washing HRP-conjugated anti-mouse and anti-human secondary antibodies were diluted 1:10,000 in blocking buffer, and incubated 1 hr at room temperature. Membrane was exposed to chemiluminescent substrate, and developed on film.

Example 5.

Use of Chimeric Recombinant Dengue Viruses to Map the Serotype 2 Neutralizing Human Antibody Response Primary infection with one of the four dengue virus (DENV) serotypes (DENV1-4) results in antibodies that neutralize the infecting serotype, but not other serotypes Our group has previously reported on the isolation of serotype specific, strongly neutralizing monoclonal antibodies (hMAbs) from people exposed to natural DENV infections. We have demonstrated that these hMAbs bind to complex quaternary structure epitopes that are only expressed on intact virus particles. Recently we reported that it is possible to create viable recombinant DENVs in which these complex epitopes have been transplanted between serotypes. By using DENV3/4 chimeras, we observed that the hinge region between domains I/II of the envelope (E) protein contains epitopes that are the main target of type-specific antibodies that neutralize serotypes 3 and 4. In the current study we have used a similar approach to map sites of DENV2 recognized by neutralizing hMAbs and primary DENV2 human immune sera. Our studies have led to the identification of a novel quaternary structure-dependent DENV2 epitope that is distinct from EDI/II hinge region epitopes previously defined for serotypes 3 and 4. Importantly, we use gain and loss of function studies to demonstrate that different locations in the DENV1-4 E glycoprotein encode unique long-lived neutralizing epitopes, which are portable between serotypes. The location of a DENV2 epitope and its relative importance as a target for neutralizing antibodies in people exposed to natural infections and vaccines was examined.

Design and Construction of rDENV4/2 Virus

Residues from DENV2 (right) were moved into DENV4 backbone to generate a recombinant DENV 4/2 virus (rDENV4/2, FIG. 24, Panel A). A reverse genetics system for manipulating the DENV genome was used (FIG. 24, Panel B). Top=DENV2, bottom=DENV4. The DENV genome is divided into four plasmid cassettes which can be individually mutated, ligated together, and electroporated into cells to generate recombinant virus. The DENV4-A cassette contains the envelope gene where mutations are made. Replacing the DENV4 residues with those from DENV 2 creates an rDENV4/2 virus, built entirely on the DENV4 genetic backbone.

A New Method for Serotype Identification by RT-PCR and Confirmation of DENV4 Backbone Recombinant Virus RT-PCT primers were designed for serotype-specific RT-PCR (FIG. 25, Panel A). The primers utilized included a common sense oligonucleotide targeting the highly conserved 3' end NS1 gene and serotype-specific antisense primers target the highly divergent NS2A gene. Viruses were grown in C6/36 cells, culture supernatant was collected and centrifuged to remove any cellular debris. Viral RNA was isolated using QIAGEN QIAmp Viral RNA Miniprep Kit. PCR was run for 35 cycles, and PCR product was analyzed on a 1.5% Ultrapure agarose gel. Control RNA (DV1/DV2/DV3/DV4) and water are run as positive and negative controls (FIG. 25, Panel B). Expected product sizes: DV1=205 bp, DV2=539 bp, DV3=455 bp, DV4=401 bp.

Restriction Fragment Length Polymorphism Distinguishes rDENV4/2 from Parental DENV4

Restriction fragment length polymorphism (RFLP) analysis was used to distinguish rDENV4/2 (bottom) from parental DENV4 (top). Mutations (represented as asterisks) introduced into the DENV4 E genome to generate rDENV4/2 disrupt an XmnI restriction enzyme site present in DENV4 (FIG. 26, Panel A). PCR products were gel purified and digested with XmnI. Digest products were analyzed on a 1.5% Ultrapure agarose gel (FIG. 26, Panel B). Expected product sizes: full length undigested=1031 bp, digested products=931 by and 113 bp.

DENV4 and rDENV4/2 Virions have Similar Maturation Profiles

Viruses were grown in C6/36 cells, and culture supernatants were collected and centrifuged to remove any cellular debris. Samples were run on a 12% SDS-PAGE gel and blots were probed with anti-E (4G2) and anti-PrM (2H12 and 5L20) antibodies (FIG. 27). DENV2 has substantial levels of PrM present, indicating either incomplete Furin processing or PrM dissociation. PrM bands are not detected in either DENV4 or rDENV4/2 samples.

rDENV4/2 has a 2 Log Growth Attenuation in Vero Cells Relative to Parental Viruses.

Vero-81 cells were infected at an MOI=0.01 with DENV2, DENV4 and rDENV4/2. Viral supernatants were collected every 24 hours and subsequently titered on Vero-81 cells (FIG. 28, Panel A). DENV forms infectious foci in Vero-81 cells. DENV2, DENV4, and rDENV4/2 were fixed 5, 4, and 6 days post-infection, respectively (FIG. 28, Panel B). rDENV4/2 exhibited foci that were smaller than both parental viruses.

rDENV4/2 has No Growth Attenuation in C6/36 Cells and Forms Similar Infectious Foci Relative to Parental Viruses C6/36 cells were infected at an MOI=0.01 with DENV2, DENV4 and rDENV4/2. Viral supernatants were collected every 24 hours and subsequently titered on C6/36 cells (FIG. 29, Panel A). DENV forms infectious foci on C6/36 cells. DENV2, DEVN4, and rDENV4/2 fixed 4, 3, and 5 days post-infection, respectively (FIG. 29, Panel B). With additional day(s) of growth, rDENV4/2 foci reach sizes comparable with parental viruses.

FIG. 30. Transfer of Binding and Neutralization of rDENV4/2 by Type-Specific DENV2 Human MAb A summary of the binding of human MAb 2D22, a strongly neutralizing DV2 MAb, that binds to a quaternary epitope is shown in FIG. 30, Panel A. 2D22 shows great specificity for neutralizing DENV2. ELISA assays show a transfer of partial binding of 2D22 to rDENV4/2, above levels of parental DV4 but not to DV2 levels (FIG. 30, Panel B). ELISA binding of the cross-reactive control antibody, 2J20, showed comparable levels of virus present and maintained virus integrity (FIG. 20, Panel C). A Vero-81 based Focus Reduction Neutralization Test (FRNT) was performed using 2D22 and FRNT$_{50}$ (concentration of antibody required to neutralize 50% of infection) values were calculated (FIG. 30, Panel 0). A U937+DC-SIGN based neutralization assay (Neut) was performed using 2D22 and Neut$_{50}$ values were calculated (FIG. 30, Panel E). In both assays (FIG. 30, Panels D-E), rDENV4/2 gained neutralization to 2D22 to levels higher than DV2. DV4 was not neutralized with the maximum concentration of 2D22 in either assay.

rDENV4/2 Gains Neutralization to DENV2 Polyclonal Immune Sera while Preserving Neutralization to DENV4 Polyclonal Sera A Vero-81 FRNT assay showed that rDENV4/2 gained neutralization to DENV2 polyclonal immune sera to levels comparable to parental DENV2 (FIG. 31, Panel A). rDENV4/2 showed no loss to neutralization by DENV4 polyclonal immune sera (FIG. 31, Panel B). rDENV4/2 showed no gain of neutralization to heterotypic DENV1 (FIG. 31, Panel C) and DENV3 (FIG. 31, Panel D) polyclonal immune sera above either parental DENV 2 or immune sera without losing neutralization to DENV4 polyclonal immune sera; rDENV4/2 gains no neutralization to heterotypic polyclonal immune sera; and rDENV4/2 may be developed as a bivalent vaccine to elicit protective antibody responses to both DENV2 and DENV4.

Example 6.

Amino Acid Alignments of Recombinant DENV with Wild-Type DENV Sequences

An amino acid sequence alignment of DV4-EDIII-DV2 with wild-type DENV4 and DENV2 is presented in FIG. 32A. An amino acid alignment of DENV2-1F4E with wild-type DENV 2 and DENV1 is presented in FIG. 32B. Lastly, an amino acid alignment of DENV4 M12, DENV4 M14 and DENV4 M16 with wild-type DENV4 and DENV3 is presented in FIG. 32B.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 1

Summary of amino acid changes in recombinant DV4-EDIII-DV2 virus

| Position | DV2 | DV4 | AA change | |
|---|---|---|---|---|
| 307 | K | S | positive charge → polar uncharged | Of 40aa residues that were |
| 309 | V | D | hydrophobic uncharged → negative charge | changed in recombinant |
| 320 | I | T | hydrophobic uncharged → polar uncharged | virus, 14 introduced a |
| 325 | Q | K | polar uncharged → positive charge | change of charge. Six |
| 329 | D | A | negative charge → hydrophobic uncharged | residues increase negative |
| 331 | S | A | polar uncharged → hydrophobic uncharged | charge (light red = positive |
| 340 | T | R | polar uncharged → positive charge | → uncharged, dark red = |
| 343 | E | N | negative charge → polar uncharged | uncharged → negative), |
| 345 | R | E | positive charge → negative charge | while eight residues |
| 353 | V | S | hydrophobic uncharged → polar uncharged | increase positive charge |
| 358 | T | E | polar uncharged → negative charge | (light blue = negative → |
| 359 | E | N | negative charge → polar uncharged | uncharged, dark blue = |
| 360 | K | T | positive charge → polar uncharged | uncharged → positive). |
| 361 | D | N | negative charge → polar uncharged | Additional residue changes |
| 364 | V | T | hydrophobic uncharged → polar uncharged | replace hydrophobic amino |
| 382 | E | G | negative charge → hydrophobic uncharged | acids with polar amino |
| 383 | P | N | hydrophobic uncharged → polar uncharged | acids, and vice versa. |
| 384 | G | S | hydrophobic uncharged → polar uncharged | |
| 385 | Q | A | polar uncharged → hydrophobic uncharged | |
| 387 | K | T | positive charge → polar uncharged | |
| 389 | N | H | polar uncharged → positive charge | |

DENV4 neutralization titers. Sera from individuals with either nature infection, or experimental vaccination are coded as indicated. Samples with FRNT$_{50}$<20 graphed at sera dilution factor of 19.

In this study, a recombinant DENV virus was generated comprised of envelope residues from two DENV serotypes (DENV2 and DENV4), and in characterizing this virus have identified several key findings: a viable recombinant virus by transplanting regions from one DENV serotype to another can be created; rDENV4/2 growth is attenuated in mammalian cells, but not insect cells; rDENV4/2 has no detectable PrM protein present, indicating it is fully processed and highly mature; binding and neutralization was transferred to the human DENV2 type-specific MAb 2D22 in two different cell types and neutralizing assays; rDENV4/2 gains neutralization to DENV2 polyclonal

TABLE 2

Mabs used to probe surface topology of DV4-EDIII-DV2

| binding specificity | MAb | binds rEDIII | additional notes |
|---|---|---|---|
| DV2 type-specific | 2D22 | − | escape mutant, R323F (EDIII) |
| | 3F9 | + | — |
| | 1L12 | − | — |
| | DVC3.7 | + | EDIII lateral ridge epitope |
| DV subcomplex | DVC10.16 | + | EDIII A-strand epitope |
| DV complex | DVC13.6 | − | scanning alanine mutations = 101 and 108 (fusion loop) |
| | DVC23.13 | − | — |

TABLE 2-continued

Mabs used to probe surface topology of DV4-EDIII-DV2

| binding specificity | MAb | binds rEDIII | additional notes |
|---|---|---|---|
| DV4 type-specific | DV4-E88 | + | mouse MAb, known EDIII epitope, scanning alanine mutations = 331 and 361 (EDIII) |

Additional MAbs used in subsequent experiments.
A subset of DENV2 type-specific MAbs bind recombinant EDIII.
Some MAbs that do not bind rEDIII are suspected to contain EDIII in their epitope.

SEQUENCES

>Parent_WT_DENV3: 115-773 E [Dengue virus 3, SEQ ID NO: 12]
MRCVGIGNRDFVEGLSGATWVDVVLEHGGCVTTMAKNKPTLDIELQKTEA
TQLATLRKLCIEGKITNITTDSRCPTQGEAVLPEEQDQNYVCKHTYVDRG
WGNGCGLFGKGSLVTCAKFQCLEPIEGKVVQYENLKYTVIITVHTGDQHQ
VGNETQ--
GVTAEITPQASTTEAILPEYGTLGLECSPRTGLDFNEMILLTMKNKAWMV
HRQWFFDLPLPWTSGATTETPTWNRKELLVTFKNAHAKKQEVVLGSQEG
AMHTALTGATEIQNSGGTSIFAGHLKCRLMDKLELKGMSYAMCTNTFVL
KKEVSETQHGTILIKVEYKGEDAPCKIPFSTEDGQGKAHNGRLITANPVV
TKKEEPVNIEAEPPFGESNIVIGIGDNALKINWYKKGSSIGKMFEATARG
ARRMAILGDTAWDFGSVGGVLNSLGKMVHQIFGSAYTALFSGVSWVMKIG
IGVLLTWIGLNSKNTSMSFSCIAIGIITLYLGAVVQA >DENV4_M12: 115-775 E (SEQ ID NO: 2)
MRCVGNRDFVEGVSGGAWVDLVLEHGGCVTTMAQGKPTLDFELTKTTA
TQLATLRKLCIEASISNITTATRCPTQGEPYLKEEQDQQYICRRDVVDRG
WGNGCGLFGKGGVVTCAKFSCSGPIEGKVVQIENLEYTVVVTVHNGDTHA
VGNDTSNHGVTATITPRSPSVEVKLPDYGELTLDCEPRSGIDFNEMILLT
MKKKAWMVHRQWFFDLPLPWTSGADTSEVHWNYKERMVTFKVPHAKRQDV
TVLGSQEGAMHSALAGATEIQNSGGTSIFAGHLKCKVRMEKLRIKGMSYT
MCSGKFSIDKEMAETQHGTTVVKVKYEGAGAPCKVPIEIRDVNKEKVVGR
VISSTPLAENTNSVTNIELEPPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA >DENV4_M14: 115-775 E (SEQ ID NO: 3)
MRCVGVGNRDFVEGVSGGAWVDLVLEHGGCVTTMAQGKPTLDFELTKTEA
TQLATLRKLCIEASISNITTATRCPTQGEPYLKEEQDQQYICRRDVVDRG
WGNGCGLFGKGGVVTCAKFSCLEPIEGKVVQYENLEYTVVVTVHNGDTHA
VGNDTSNHGVTATITPRSPSVEVKLPDYGELTLDCEPRSGIDFNEMILLT
MKKKAWMVHRQWFFDLPLPWTSGADTSEVHWNYKERMVTFKVPHAKRQDV
TVLGSQEGAMHSALAGATEIQNSGGTSIFAGHLKCKVRMEKLRIKGMSYT
MCSGKFSIDKEMAETQHGTTVVKVKYEGAGAPCKVPIEIRDVNKEKVVGR
VISSTPLAENTNSVTNIELEPPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA >DENV4_M16: 115-775 E (SEQ ID NO: 4)
MRCVGNRDFVEGVSGGAWVDLVLEHGGCVTTMAQGKPTLDFELTKTEA
TQLRKLCIEASISNITTDTRCPTQGEPYLKEEQDQQYICRRDVVDRG
WGNGCGLFGKGGVVTCAKFSCLEPIEGKVVQYENLEYTVVVTVHNGDQHA
VGNDTSNHGVTATITPRSPSVEVKLPDYGELTLDCEPRSGIDFNEMILLT
MKKKAWMVHRQWFFDLPLPWTSGATTSEPHWNYKERMVTFKVPHAKRQDV
TVLGSQEGAMHSALAGATEIQNSGGTSIFAGHLKCKVRMEKLRIKGMSYT
MCSGKFSIKKEMAETQHGTTVVKVKYEGAGAPCKVPIEIRDVNKEKVVGR
VISSTPLAENTNSPTNIELEPPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA >Parent_WT_DENV4: 115-775 E [Dengue virus 4, SEQ ID NO: 1]
MRCVGVGNRDFVEGVSGGAWVDLVLEHGGCVTTMAQGKPTLDFELTKTTA
KEVALLRTYCIEASISNITTATRCPTQGEPYLKEEQDQQYICRRDVVDRG
WGNGCGLFGKGGVVTCAKFSCSGKITGNLVQIENLEYTVVVTVHNGDTHA
VGNDTSNHGVTATITPRSPSVEVKLPDYGELTLDCEPRSGIDFNEMILMK
MKKKTWLVHKQWFLDLPLPWTAGADTSEVHWNYKERMVTFKVPHAKRQDV
TVLGSQEGAMHSALAGATEVDSGDGNHMFAGHLKCKVRMEKLRIKGMSYT
MCSGKFSIDKEMAETQHGTTVVKVKYEGAGAPCKVPIEIRDVNKEKVVGR
VISSTPLAENTNSVTNIELEPPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA >Parent_WT_DENV2: 115-775 [Dengue virus 2, SEQ ID NO: 13]
MRCIGISNRDFVEGVSGGSWVDIVLEHGSCVTTMAKNKPTLDFELIKTEA
KQPATLRKYCIEAKLTNTTTESRCPTQGEPSLNEEQDKRFICKHSMVDRG
WGNGCGLFGKGGIVTCAMFTCKKNMEGKVVQPENLEYTIVITPHSGEEHA
VGNDTGKHGKEIKITPQSSITEAELTGYGTVTMECSPRTGLDFNEMVLLQ
MEDKAWLVHRQWFLDLPLPWLPGADTQESNWIQKETLVTFKNPHAKKQDV
VVLGSQEGAMHTALTGATEIQMSSGNLLFTGHLKCRLRMDKLQLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA >DV4-EDIII-DV2: 115-775 [Dengue virus 4/2, SEQ ID NO: 5]
MRCVGVGNRDFVEGVSGGAWVDLVLEHGGCVTTMAQGKPTLDFELTKTTA
KEVALLRTYCIEASISNITTATRCPTQGEPYLKEEQDQQYICRRDVVDRG
WGNGCGLFGKGGVVTCAKFSCSGKITGNLVQIENLEYTVVVTVHNGDTHA
VGNDTSNHGVTATITPRSPSVEVKLPDYGELTLDCEPRSGIDFNEMILMK
MKKKTWLVHKQWFLDLPLPWTAGADTSEVHWNYKERMVTFKVPHAKRQDV
TVLGSQEGAMHSALAGATEVDSGDGNHMFAGHLKCKVRMEKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA >Parent_WT_DENV1: 115-775 E [Dengue virus 1, SEQ ID NO: 14]
MRCVGIGNRDFVEGLSGATWVDVVLEHGSCVTTMAKDKPTLDIELLKTEV
TNPAVLRKLCIEAKISNTTTDSRCPTQGEATLVEEQDTNFVCRRTFVDRG
WGNGCGLFGKGSLITCAKFKCVTKLEGKIVQYENLKYSIVIVTVHTGDQHQ
VGNETTEHGTTATITPQAPTSEIQLTDYGALTLDCSPRTGLDFNEMVLLT
MEKKSWLVHKQWFLDLPLPWTSGASTSQETWNRQDLLVTFKTAHAKKQEV
VVLGSQEGAMHTALTGATEIQTSGTTTIFAGHLKCRLKMDKLTLKGMSYV
MCTGSFKLEKEVAETQHGTVLVQVKYEGTDAPCKIPFSSQDEKGVTQNGR
LITANPIVTDKEKPVNIEAEPPFGESYIVVGAGEKALKLSWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA >DENV2-1F4E: 115-775
MRCIGISNRDFVEGVSGGSWVDIVLEHGSCVTTMAKNKPTLDFELFKTEV
TNPAVLRKYCIEAKLTNTTTESRCPTQGEPSLNEEQDKRFICKHSMVDRG
WGNGCGLFGKGGIVTCAMFTCKKNMEGKVVQPENLKYSIVITVHSGEEHA
VGNDTTEHGTTATITPQAPTSEIQLTDYGALTLECSPRTGLDFNEMVLLQ
MEDKAWLVHRQWFLDLPLPWLPGADTQESNWIQKETLVTFKNPHAKKQDV
VVLGSQEGAMHTALTGATEIQTSGTTTLFTGHLKCRLKMDKLQLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ ID NO: 6)

DENV1/4 (5H2)
MRCVGIGNRDFVEGLSGATWVDVVLEHGSCVTTMAKDKPTLDIELLKTEV
TNPAVLRKLCIEAKISNTTTDSRCPTQGEATLVEEQDTNFVCRRTFVDRG
WGNGCGLFGKGSLITCAKFKCVTKLEGKIVQYENLKYSIVIVTVHTGDQHQ
VGNEATEHGVTAMITPQSPSVEVKLPDYGELTLDCSPRTGLDFNEMVLLT
MKKKSWLVHKQWFLDLPLPWTSGASTSQETWNRQDLLVTFKTAHAKKQEV
VVLGSQEGAMHTALTGATEIQTSGTTTIFAGHLKCRLKMDKLRLKGMSYV
MCTGSFKLEKEVAETQHGTVLVQVKYEGTDAPCKIPFSSQDEKGVTQNGR
LITANPIVTDKEKPVNIEAEPPFGESYIVVGAGEKALKLSWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ ID NO: 15)

DENV2/4 (5H2)
MRCIGISNRDFVEGVSGGSWVDIVLEHGSCVTTMAKNKPTLDFELIKTEA
KQPATLRKYCIEAKLTNTTTESRCPTQGEPSLNEEQDKRFICKHSMVDRG
WGNGCGLFGKGGIVTCAMFTCKKNMEGKVVQPENLEYTIVITPHSGEEHA
VGNDAGKHGVTAMITPQSSSVEVKLPDYGEVTMECSPRTGLDFNEMVLLQ
MEDKAWLVHRQWFLDLPLPWLPGADTQESNWIQKETLVTFKNPHAKKQDV
VVLGSQEGAMHTALTGATEIQTSGTTTLFTGHLKCRLRMDKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ

ID NO: 16)

DENV2-1F4E (Strain 16803)
MRCIGISNRDFVEGVSGGSWVDIVLEHGSCVTTMAKNKPTLDFELFKTEV
TNPAVLRKYCIEAKLTNTTTESRCPTQGEPSLNEEQDKRFVCKHSMVDRG
WGNGCGLFGKGGIVTCAMFTCKKNMEGKVVQPENLKYSVIVTVHSGEEHA
VGNDTTEHGTTATVTPQAPTSEIQLTDYGALTLECSPRTGLDFNEMVLLQ
MENKAWLVHRQWFLDLPLPWLPGADTQGSNWIQKETLVTFKNPHAKKQDV
VVLGSQEGAMHTALTGATEIQTSGTTTLFTGHLKCRLRMDKLQLKGMSYS
MCTGKFKVVKEIAETQHGTIVIRVQYEGDGSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ
ID NO: 17)

The following changes could also be made to
generate 2 viruses with smaller regions of DENV1
transplanted into DENV2:
1. N52Q, V55T, S138T, V139I
2. A168S, P169S, A180T, L181V, L183M (in addition
to those listed in #1)

DENV4-1F4E
MRCVGVGNRDFVEGVSGGAWVDLVLEHGGCVTTMAQGKPTLDFELFKTTV
TNPAVLRTYCIEASISNITTATRCPTQGEPYLKEEQDQQYICRRDVVDRG
WGNGCGLFGKGGVVTCAKFSCSGKITGNLVQIENLKYSVIVTVHNGDTHA
VGNDTTEHGTTATITPRAPTSEIQLTDYGALTLDCEPRSGIDFNEMILMK
MKKKTWLVHKQWFLDLPLPWTAGADTSEVHWNYKERMVTFKVPHAKRQDV
TVLGSQEGAMHSALAGATEVDTGGTTTMFAGHLKCKVRMEKLRIKGMSYT
MCSGKFSIDKEMAETQHGTTVVKVKYEGAGAPCKVPIEIRDVNKEKVVGR
VISSTPLAENTNSVTNIELEPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 18)

The following changes could also be made to
generate 2 viruses with smaller regions of DENV1
transplanted into DENV2:
1. N52E, P53V, V55L, S138T
2. A168S, A180E (in addition to those listed in #1)

DENV1-3M14
MRCVGIGNRDFVEGLSGATWVDVVLEHGSCVTTMAKDKPTLDIELLKTEV
TNPAVLRKLCIEAKISNTTTDSRCPTQGEATLVEEQDTNFVCRRTFVDRG
WGNGCGLFGKGSLITCAKFKCLEPIEGKVVQYENLKYSVIVTVHTGDQHQ
VGNETTEHGTIATITPQAPTSEIQLTDYGALTLDCSPRTGLDFNEMILLT
MKNKAWMVHRQWFFDLPLPWTSGASTSQETWNRQDLLVTFKTAHAKKQEV
VVLGSQEGAMHTALTGATEIQNSGGTSIFAGHLKCRLKMDKLTLKGMSYV
MCTGSFKLEKEVAETQHGTVLVQVKYEGTDAPCKIPFSSQDEKGVTQNGR
LITANPIVTDKEKPVNIEAEPPFGESYIVVGAGEKALKLSWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ
ID NO: 19)

The following changes could also be made to
generate a virus with a larger region of DENV3
transplanted into DENV1 (designated DENV1-3M16):
1. S225T, E229P, E307K DENV2/3 M12 (Strain 16803)
MRCIGISNRDFVEGVSGGSWVDIVLEHGSCVTTMAKNKPTLDFELIKTEA
TQLATLRKLCIEAKLTNTTTESRCPTQGEPSLNEEQDKRFVCKHSMVDRG
WGNGCGLFGKGGIVTCAMFTCKEPIEGKVVQPENLEYTIVVTPHSGEEHA
VGNDTGKHGKEIKVTPQSSITEAELTGYGTVTMECSPRTGLDFNEMVLLT
MKNKAWMVHRQWFFDLPLPWTSTADTQGPNWIQKETLVTFKNPHAKKQDV
VVLGSQEGAMHTALTGATEIQNSGGTSIFAGHLKCRLRMDKLQLKGMSYS
MCTGKFKVVKEIAETQHGTIVIRVQYEGDGSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGIVTLYLGVMVQA (SEQ
ID NO: 20)

The following changes could also be made to
generate 2 viruses with a larger region of DENV3
transplanted into DENV2 (designated DENV2-M14(#1)
and DENV2-M16(#2)):
1. K122L, K123E, P132Y
2. E71D, E148Q, D225T, S229P, V307K (in addition
to those listed in #1)

DENV3/4 (5H2)
MRCVGIGNRDFVEGLSGATWVDVVLEHGGCVTTMAKNKPTLDIELQKTEA
TQLATLRKLCIEGKITNITTDSRCPTQGEAVLPEEQDQNYVCKHTYVDRG
WGNGCGLFGKGSLVTCAKFQCLEPIEGKVVQYENLKYTIITVHTGDQHQ
VGNEASNQGVTAMITPQSSSVEVKLPDYGELGLECSPRTGLDFNEMILLT
MKNKAWMVHRQWFFDLPLPWTSGATTETPTWNRKELLVTFKNAHAKKQEV
VVLGSQEGAMHTALTGATEIQNSGGTSIFAGHLKCRLKMDKLRLKGMSYA
MCTNTFVLKKEVSETQHGTILIKVEYKGEDAPCKIPFSTEDGQGKAHNGR
LITANPVVTKKEEPVNIEAEPPFGESNIVIGIGDNALKINWYKKGSSIGK
MFEATARGARRMAILGDTAWDFGSVGGVLNSLGKMVHQIFGSAYTALFSG
VSWVMKIGIGVLLTWIGLNSKNTSMSFSCIAIGIITLYLGAVVQA (SEQ
ID NO: 21)

DV4-EDIII-DV2
MRCVGVGNRDFVEGVSGGAWVDLVLEHGGCVTTMAQGKPTLDFELTKTTA
KEVALLRTYCIEASISNITTATRCPTQGEPYLKEEQDQQYICRRDVVDRG
WGNGCGLFGKGGVVTCAKFSCSGKITGNLVQIENLEYTVVVTVHNGDTHA
VGNDTSNHGVTATITPRSPSVEVKLPDYGELTLDCEPRSGIDFNEMILMK
MKKKTWLVHKQWFLDLPLPWTAGADTSEVHWNYKERMVTFKVPHAKRQDV
TVLGSQEGAMHSALAGATEVDSGDGNHMFAGHLKCKVRMEKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 22)

The following changes could also be made to
generate 2 viruses with a larger region of DENV2
transplanted into DENV4:
1. Y81S, K83S, V242N, R247K
2. I68T, A71E, T72S, R93K, R94H, D95S, V96M, V113I
(in addition to those listed in #1)

DV1-EDIII-DV2
MRCVGIGNRDFVEGLSGATWVDVVLEHGSCVTTMAKDKPTLDIELLKTEV
TNPAVLRKLCIEAKISNTTTDSRCPTQGEATLVEEQDTNFVCRRTFVDRG
WGNGCGLFGKGSLITCAKFKCVTKLEGKIVQYENLKYSVIVTVHTGDQHQ
VGNETTEHGTTATITPQAPTSEIQLTDYGALTLDCSPRTGLDFNEMVLLT
MEKKSWLVHKQWFLDLPLPWTSGASTSQETWNRQDLLVTFKTAHAKKQEV
VVLGSQEGAMHTALTGATEIQTSGTTTIFAGHLKCRLKMDKLTLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ
ID NO: 23)

The following changes could also be made to
generate 2 viruses with a larger region of DENV2
transplanted into DENV1:
1. I68T, D71E, A80P, T81S, V83N, T242N, A243P,
E249D
2. R93K, R94H, T95S, F96M, SI12G, L113I, I114V (in
addition to those listed in #1)

DV3-EDIII-DV2
MRCVGIGNRDFVEGLSGATWVDVVLEHGGCVTTMAKNKPTLDIELQKTEA
TQLATLRKLCIEGKITNITTDSRCPTQGEAVLPEEQDQNYVCKHTYVDRG
WGNGCGLFGKGSLVTCAKFQCLEPIEGKVVQYENLKYTIITVHTGDQHQ
VGNETQGVTAEITPQASTTEAILPEYGTLGLECSPRTGLDFNEMILLTMK
NKAWMVHRQWFFDLPLPWTSGATTETPTWNRKELLVTFKNAHAKKQEVVV
LGSQEGAMHTALTGATEIQNSGGTSIFAGHLKCRLKMDKLELKGMSYSMC
TGKFKIVKEIAETQHGTIVIRVQYEGDGSPCKIPFEITDLEKRHVLGRLI
TVNPIVTEKDSPVNIEAEPPFGDSYIIIGVEPGQLKLNWYKKGSSIGKMF
EATARGARRMAILGDTAWDFGSVGGVLNSLGKMVHQIFGSAYTALFSGVS
WVMKIGIGVLLTWIGLNSKNTSMSFSCIAIGIITLYLGAVVQA (SEQ
ID NO: 24)

The following changes could also be made to
generate 2 viruses with a larger region of DENV2
transplanted into DENV3:
1. D71E, A80P, V81S, P83N, A243P, E249D
2. I68T, T95S, Y96M, SI12G, L113I (in addition to
those listed in #1)

DENV2/1/3 (Strain 16803)
MRCIGISNRDFVEGVSGGSWVDIVLEHGSCVTTMAKNKPTLDFELFKTEV
TQLATLRKLCIEAKLTNTTTESRCPTQGEPSLNEEQDKRFVCKHSMVDRG
WGNGCGLFGKGGIVTCAMFTCKKPIEGKVVQPENLKYTIIVTVHSGEEHA
VGNDTTEHGTTATVTPQSSTSEIQLTDYGTVTMECSPRTGLDFNEMILLT
MKNKAWMVHRQWFFDLPLPWTSGADTQGSNWIQKETLVTFKNPHAKKQDV
VVLGSQEGAMHTALTGATEIQTSSTTTIFAGHLKCRLRMDKLQLKGMSYS
MCTGKFKVVKEIAETQHGTIVRVQYEGDSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ
ID NO: 25)

Note: AA #50 could be a V or A, AA #52 could be a
Q or N, AA #55 could be a T or V, AA #272 could be
a T or N, AA #275 could be a T or G, AA #276 could
be a T or N, AA #277 could be a T or L The following changes could also be made to
generate viruses with larger regions of DENV1
and/or DENV3 transplanted into DENV2:
1. Q52N, T55V, T138S, I139V
2. S168A, S169P, TI80A, V181L, MI83L(in addition
to those listed in #1)
3. K122L, K123E, P132Y
4. E71D, E148Q, D225T, S227P, V307K (in addition
to those listed in #3)
5. Any and all combinations of 1, 2, 3, 4 and the
original sequence (i.e., 1 + 3, 1 + 4, 2 + 3,
2 + 4)

DENV2/1/4
MRCIGISNRDFVEGVSGGSWVDIVLEHGSCVTTMAKNKPTLDFELFKTEV
TQPATLRKYCIEAKLTNTTTESRCPTQGEPSLNEEQDKRFVCKHSMVDRG
WGNGCGLFGKGGIVTCAMFTCKKNMEGKVVQPENLKYTIIVTVHSGEEHA
VGNDATEHGVTAMVTPQSSTVEVKLPDYGEVTMECSPRTGLDFNEMVLLQ
MENKAWLVHRQWFLDLPLPWLPGADTQGSNWIQKETLVTFKNPHAKKQDV
VVLGSQEGAMHTALTGATEIQTSGTTTLFTGHLKCRLRMDKLRLKGMSYS
MCTGKFKVVKEIAETQHGTIVIRVQYEGDGSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ
ID NO: 26)

Note: AA #160 could be a T or V, AA #163 could be
a T or M, AA #168 could be a S or A, AA #170 could
be a T or S, AA #171 could be a S or V, AA #173
could be a V or I, AA #174 could be a Q or K, AA
176 could be a P or T, AA #180 could be a E or A The following changes could also be made to
generate viruses with larger regions of DENV1
transplanted into DENV2:
1. Q52N, T55V, T138S, I139V
2. S168A, S169P, T180A, V181L, M183L (in addition
to those listed in #1)

DENV2/3/4 (Strain 16803)
MRCIGISNRDFVEGVSGGSWVDIVLEHGSCVTTMAKNKPTLDFELIKTEA
TQLATLRKLCIEAKLTNTTTESRCPTQGEPSLNEEQDKRFVCKHSMVDRG
WGNGCGLFGKGGIVTCAMFTCKEPIEGKVVQPENLEYTIVVTPHSGEEHA
VGNDAGKHGVTAMVTPQSSSVEVKLPDYGEVTMECSPRTGLDFNEMVLLT
MKNKAWMVHRQWFFDLPLPWTSTADTQGPNWIQKETLVTFKNPHAKKQDV
VVLGSQEGAMHTALTGATEIQNSGGTSIFAGHLKCRLRMDKLRLKGMSYS
MCTGKFKVVKEIAETQHGTIVIRVQYEGDGSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGIVTLYLGVMVQA (SEQ
ID NO: 27)

The following changes could also be made to
generate 2 viruses with a larger region of DENV3
transplanted into DENV2:
1. K122L, K123E, P132Y
2. E71D, E148Q, D225S, S229P, V307K (in addition
to those listed in #1)

DENV2/11314 (Strain 16803)
MRCIGISNRDFVEGVSGGSWVDIVLEHGSCVTTMAKNKPTLDFELFKTEV
TQLATLRKLCIEAKLTNTTTESRCPTQGEPSLNEEQDKRFVCKHSMVDRG
WGNGCGLFGKGGIVTCAMFTCKKPIEGKVVQPENLKYTIIVTVHSGEEHA
VGNDATEHGVTAMVTPQASSVEVKLPDYGEVTMECSPRTGLDFNEMILLT
MKNKAWMVHRQWFFDLPLPWTSGADTQGSNWIQKETLVTFKNPHAKKQDV
VVLGSQEGAMHTALTGATEIQTSSTTTIFAGHLKCRLRMDKLRLKGMSYS
MCTGKFKVVKEIAETQHGTIVIRVQYEGDSPCKIPFEIMDLEKRHVLGR
LITVNPIVTEKDSPVNIEAEPPFGDSYIIIGVDPGQLKLNWFKKGSSIGQ
MFETTMRGAKRMAILGDTAWDFGSLGGVFTSIGKALHQVFGAIYGAAFSG
VSWTMKILIGVIITWIGMNSRSTSLSVSLVLVGVVTLYLGAVVQA (SEQ
ID NO: 28)

Note: AA #50 could be a V or A, AA #52 could be a
Q or N, AA #55 could be a T or V, AA #160 could be
a T or V, AA #163 could be a T or M, AA #168 could
be a S or A, AA #170 could be a T or S, AA #171
could be a S or V, AA #173 could be a V or I, AA
174 could be a Q or K, AA #176 could be a P or T,
AA #180 a E or A, AA #272 could be a T or N, AA
275 could be a T or G, AA #276 could be a T or N,
AA #277 could be a T or L The following changes could also be made to
generate viruses with larger regions of DENV1
and/or DENV3 transplanted into DENV2:
1. Q52N, T55V, T1385, I139V
2. S168A, S169P, T180A, V181L, M183L (in addition
to those listed in #1)
3. K122L, K123E, P132Y
4. E71D, E148Q, D225T, S227P, V307K (in addition
to those listed in #3)
5. Any and all combinations of 1, 2, 3, 4 and the
original sequence DENV1/3/4
MRCVGIGNRDFVEGLSGATWVDVVLEHGSCVTTMAKDKPTLDIELLKTEA
TQLATLRKLCIEAKISNTTTDSRCPTQGEATLVEEQDTNFVCRRTFVDRG
WGNGCGLFGKGSLITCAKFKCVTKIEGKVVQYENLKYSIVITVHTGDQHQ
VGNEATEHGVTAMITPQSPSVEVKLPDYGELTLDCSPRTGLDFNEMILLT
MKNKAWMVHRQWFLDLPLPWTSGASTSQETWNRQDLLVTFKTAHAKKQDV
VVLGSQEGAMHTALTGATEIQNSGGTSIFAGHLKCRLKMDKLRLKGMSYV
MCTGSFKLEKEVAETQHGTVLVQVKYEGTDAPCKIPFSSQDEKGVTQNGR
LITANPIVTDKEKPVNIEAEPPFGESYIVVGAGEKALKLSWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ
ID NO: 29)

Note: AA #50 could be a V or A, AA #52 could be a
Q or N, AA #55 could be a T or V, AA #272 could be
a T or N, AA #275 could be a T or G, AA #276 could
be a T or N, AA #277 could be a T or L The following changes could also be made to
generate viruses with a larger region of DENV3
transplanted into DENV1:
1. V122L, T123E, K124P, L214F
2. S225T, E229P, E307K (in addition to those
listed in #1)

DENV1/2/3
MRCVGIGNRDFVEGLSGATWVDVVLEHGSCVTTMAKDKPTLDIELLKTEA
TQLATLRKLCIEAKISNTTTDSRCPTQGEATLVEEQDTNFVCRRTFVDRG
WGNGCGLFGKGSLITCAKFKCVTKIEGKVVQYENLKYSIVITVHTGDQHQ
VGNETTEHGTTATITPQAPTSEIQLTDYGALTLDCSPRTGLDFNEMILLT
MKNKAWMVHRQWFLDLPLPWTSGASTSQETWNRQDLLVTFKTAHAKKQEV
VVLGSQEGAMHTALTGATEIQNSGGTSIFAGHLKCRLKMDKLTLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK

SEQUENCES

MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ
ID NO: 30)

Note: AA #50 could be a V or A, AA #52 could be a
Q or N, AA #55 could be a T or V, AA #272 could be
a T or N, AA #275 could be a T or G, AA #276 could
be a T or N, AA #277 could be a T or L The following changes could also be made to
generate viruses with larger transplanted regions
of DENV2 and/or DENV3 into DENV1:
1. I68T, D71E, A80P, T81S, V83N, T242N, A243P,
E249D
2. R93K, R94H, T95S, F96M, S112G, L113I, I114V (in
addition to those listed in #1)
3. V122L, T123E, K124P, L214F
4. S225T, E229P, E307K (in addition to those
listed in #3)
5. Any and all combinations of 1, 2, 3, 4 and the
original sequence DENV1/2/4
MRCVGIGNRDFVEGLSGATWVDVVLEHGSCVTTMAKDKPTLDIELLKTEV
INPAVLRKLCIEAKISNTTTDSRCPTQGEATLVEEQDTNFVCRRTFVDRG
WGNGCGLFGKGSLITCAKFKCVTKLEGKIVQYENLKYSVIVTVHTGDQHQ
VGNEATEHGVTAMITPQSPSVEVKLPDYGELTLDCSPRTGLDFNEMVLLT
MEKKSWLVHKQWFLDLPLPWTSGASTSQETWNRQDLLVTFKTAHAKKQEV
VVLGSQEGAMHTALTGATEIQTSGTTTIFAGHLKCRLKMDKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFEATARGARRMAILGDTAWDFGSIGGVFTSVGKLIHQIFGTAYGVLFSG
VSWTMKIGIGILLTWLGLNSRSTSLSMTCIAVGMVTLYLGVMVQA (SEQ
ID NO: 31)

Note: AA #160 could be a T or V, AA #163 could be
a T or M, AA #168 could be a S or A, AA #170 could
be a T or S, AA #171 could be a S or V, AA #173
could be a V or I, AA #174 could be a Q or K, AA
176 could be a P or T, AA #180 could be a E or A The following changes could also be made to
generate 2 viruses with a larger region of DENV2
transplanted into DENV1:
1. I68T, D71E, A80P, T81S, V83N, T242N, A243P,
E249D
2. R93K, R94H, T95S, F96M, S112G, L113I, I114V (in
addition to those listed in #1)

DENV1/2/3/4
MRCVGIGNRDFVEGLSGATWVDVVLEHGSCVTTMAKDKPTLDIELLKTEA
TQLATLRKLCIEAKISNTTTDSRCPTQGEATLVEEQDTNFVCRRTFVDRG
WGNGCGLFGKGSLITCAKFKCVTKIEGKVVQYENLKYSVIVTVHTGDQHQ
VGNEATEHGVTAMITPQSPSVEVKLPDYGELTLDCSPRTGLDFNEMILLT
MKNKAWMVHRQWFLDLPLPWTSGASTSQETWNRQDLLVTFKTAHAKKQEV
VVLGSQEGAMHTALTGATEIQNSGGTSIFAGHLKCRLKMDKLRLKGMSYS
MCTGKFKIVICEIAETQHGTIVIRVQYEGDGSPCKIPFEITDLEKRHVLG
RLITVNPIVTEKDSPVNIEAEPPFGDSYIIIGVEPGQLKLNWFKKGSSIG
KMFEATARGARRMAILGDTAWDFGSIGGVFTSVGKLIHQIFGTAYGVLFS
GVSWTMKIGIGILLTWLGLNSRSTSLSMTCIAVGMVTLYLGVMVQA
(SEQ ID NO: 32)

Note: AA #50 could be a V or A, AA #52 could be a
Q or N, AA #55 could be a T or V, AA #160 could be
a T or V, AA #163 could be a T or M, AA #168 could
be a S or A, AA #170 could be a T or S, AA #171
could be a S or V, AA #173 could be a V or I, AA
174 could be a Q or K, AA #176 could be a P or T,
AA #180 could be a E or A, AA #272 could be a T or
N, #275 could be a T or G, #276 could be a T or N,
277 could be a T or L The following changes could also be made to
generate 2 viruses with a larger region of DENV2
and/or DENV3 transplanted into DENV1:
1. I68T, D71E, A80P, T81S, V83N, T242N, A243P,
E249D
2. R93K, R94H, T95S, F96M, S112G, L113I, I114V (in
addition to those listed in #1)
3. V122L, T123E, K124P, L214F
4. S225T, E229P, E307K (in addition to those
listed in #3)
5. Any and all combinations of 1, 2, 3, 4 and the
original sequence DENV3/1/4
MRCVGIGNRDFVEGLSGATWVDVVLEHGGCVTTMAKNKPTLDIELFKTEV
TQLATLRKLCIEGKITNITTDSRCPTQGEAVLPEEQDQNYVCKHTYVDRG
WGNGCGLFGKGSLVTCAKFQCLEPIEGKVVQYENLKYSVIITVHTGDQHQ
VGNEATEHGVTAMITPQSSSVEVKLPDYGELGLECSPRTGLDFNEMILLT
MKNKAWMVHRQWFFDLPLPWTSGATTETPTWNRKELLVTFKNAHAKKQEV
VVLGSQEGAMHTALTGATEIQNSGTTSIFAGHLKCRLKMDKLRLKGMSYA
MCTNTFVLKKEVSETQHGTILIKVEYKGEDAPCKIPFSTEDGQGKAHNGR
LITANPVVTKKEEPVNIEAEPPFGESNIVIGIGDNALKINWYKKGSSIGK
MFEATARGARRMAILGDTAWDFGSVGGVLNSLGKMVHQIFGSAYTALFSG
VSWVMKIGIGVLLTWIGLNSKNTSMSFSCIAIGIITLYLGAVVQA (SEQ
ID NO: 33)

Note: AA #50 could be a V or A, AA #52 could be a
Q or N, AA #55 could be a T or V, AA #160 could be
a T or V, AA #163 could be a T or M, AA #168 could
be a S or A, AA #170 could be a T or S, AA #171
could be a S or A, AA #173 could be a V or I, AA
174 could be a Q or K, AA #176 could be a P or T,
AA #180 could be a E or A, AA #272 could be a T or
N, AA #275 could be a T or G, AA #276 could be a T
or N, AA #277 could be a T or L The following changes could also be made to
generate viruses with larger regions of DENV1
transplanted into DENV3:
1. S169P, T180A
2. Q52N, L53P, T55V (in addition to those listed
in #1)

DENV3/1/2
MRCVGIGNRDFVEGLSGATWVDVVLEHGGCVTTMAKNKPTLDIELFKTEV
TQLATLRKLCIEGKITNITTDSRCPTQGEAVLPEEQDQNYVCKHTYVDRG
WGNGCGLFGKGSLVTCAKFQCLEPIEGKVVQYENLKYTVIVTVHTGDQHQ
VGNETTEHGVTAIITPQASTSEIQLTDYGTLGLECSPRTGLDFNEMILLT
MKNKAWMVHRQWFFDLPLPWTSGATTETPTWNRKELLVTFKNAHAKKQEV
VVLGSQEGAMHTALTGATEIQTSGTTTIFAGHLKCRLKMDKLELKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWYKKGSSIGK
MFEATARGARRMAILGDTAWDFGSVGGVLNSLGKMVHQIFGSAYTALFSG
VSWVMKIGIGVLLTWIGLNSKNTSMSFSCIAIGHTLYLGAVVQA (SEQ
ID NO: 34)

Note: AA #50 could be a V or A, AA #52 could be a
Q or N, AA #55 could be a T or V, AA #272 a T or
N, AA #275 could be a T or G, AA #276 could be a T
or N, AA #277 could be a T or L The following changes could also be made to
generate 2 viruses with a larger region of DENV2
and/or DENV1 transplanted into DENV3:
1. D71E, A80P, V81S, P83N, A243P, E249D
2. I68T, T95S, Y96M, S112G, L113I (in addition to
those listed in #1)
3. S169P, T180A
4. Q52N, L53P, T55V (in addition to those listed
in #3)
5. Any and all combinations of 1, 2, 3, 4 and the
original sequence DENV3/2/4
MRCVGIGNRDFVEGLSGATWVDVVLEHGGCVTTMAKNKPTLDIELQKTEA
TQLATLRKLCIEGKITNITTDSRCPTQGEAVLPEEQDQNYVCKHTYVDRG

SEQUENCES

WGNGCGLFGKGSLVTCAKFQCLEPIEGKVVQYENLKYTVIITVHTGDQHQ
VGNEAQGVTAMITPQSSSVEVKLPDYGELGLECSPRTGLDFNEMILLTMK
NKAWMVHRQWFFDLPLPWTSGATTETPTWNRKELLVTFKNAHAKKQEVVV
LGSQEGAMHTALTGATEIQNSGGTSIFAGHLKCRLKMDKLRLKGMSYSMC
TGKFKIVKEIAETQHGTIVIRVQYEGDGSPCKIPFEITDLEKRHVLGRLI
TVNPIVTEKDSPVNIEAEPPFGDSYIIIGVEPGQLKLNWYKKGSSIGKMF
EATARGARRMAILGDTAWDFGSVGGVLNSLGKMVHQIFGSAYTALFSGVS
WVMKIGIGVLLTWIGLNSKNTSMSFSCIAIGIITLYLGAVVQA (SEQ
ID NO: 35)

The following changes could also be made to
generate 2 viruses with a larger region of DENV2
transplanted into DENV3:
1. D71E, A80P, V81S, P83N, A243P, E249D
2. I68T, T95S, Y96M, S112G, L113I (in addition to
those listed in #1)

DENV3/1/2/4
MRCVGIGNRDFVEGLSGATWVDVVLEHGGCVTTMAKNKPTLDIELFKTEV
TQLATLRKLCIEGKITNITTDSRCPTQGEAVLPEEQDQNYVCKHTYVDRG
WGNGCGLFGKGSLVTCAKFQCLEPIEGKVVQYENLKYTVIVTVHTGDQHQ
VGNEATEHGVTAMITPQSSSVEVKLPDYGELGLECSPRTGLDFNEMILLT
MKNKAWMVHRQWFFDLPLPWTSGATTETPTWNRKELLVTFKNAHAKKQEV
VVLGSQEGAMHTALTGATEIQTSGTTTIFAGHLKCRLKMDKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWYKKGSSIGK
MFEATARGARRMAILGDTAWDFGSVGGVLNSLGKMVHQIFGSAYTALFSG
VSWVMKIGIGVLLTWIGLNSKNTSMSFSCIAIGIITLYLGAVVQA (SEQ
ID NO: 36)

Note: AA #50 could be a V or A, AA #52 could be a
Q or N, AA #55 could be a T or V, AA #160 could be
a T or V, AA #163 could be a T or M, AA #168 could
be a S or A, AA #170 could be a T or S, AA #171
could be a S or V, AA #173 could be a V or I, AA
174 could be a Q or K, AA #176 could be a P or T,
AA #180 could be a E or A, AA #272 could be a T or
N, AA #275 could be a T or G, AA #276 could be a T
or N, AA #277 could be a T or L The following changes could also be made to
generate 2 viruses with a larger region of DENV2
and/or DENV1 transplanted into DENV3:
1. D71E, A80P, V81S, P83N, A243P, E249D
2. I68T, T95S, Y96M, S112G, L113I (in addition to
those listed in #1)
3. S169P, T180A
4. Q52N, L53P, T55V (in addition to those listed
in #3)
5. Any and all combinations of 1, 2, 3, 4 and the
original sequence DENV4/1/3
MRCVGVGNRDFVEGVSGGAWVDLVLEHGGCVTTMAQGKPTLDFELFKTTV
TQLATLRKLCIEASISNITTATRCPTQGEPYLKEEQDQQYICRRDVVDRG
WGNGCGLFGKGGVVTCAKFSCSGPIEGKVVQIENLKYTVIVTVHNGDTHA
VGNDTTEHGTTATITPRSPTSEIQLTDYGELTLDCEPRSGIDFNEMILLT
MKKKAWMVHRQWFFDLPLPWTSGADTSEVHWNYKERMVTFKVPHAKRQDV
TVLGSQEGAMHSALAGATEIQNSGGTSIFAGHLKCKVRMEKLRIKGMSYT
MCSGKFSIDKEMAETQHGTTVVKVKYEGAGAPCKVPIEIRDVNKEKVVGR
VISSTPLAENTNSVTNIELEPPFGDSYIVIGVGNSALTLHWFRKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 37)

Note: AA #50 could be a V or A, AA #52 could be a
Q or N, AA #55 could be a T or V, AA #160 could be
a T or V, #163 could be a T or M, AA #168 could be
a S or A, AA #170 could be a T or S, AA #171 could
be a S or V, AA #173 could be a V or I, AA #174
could be a Q or K, AA #176 could be a P or T, AA
180 could be a E or A, AA #272 could be a T or N,
AA #275 could be a T or G, AA #276 could be a T or
N, AA #277 could be a T or L The following changes could also be made to
generate viruses with a larger region of DENV1
and/or DENV3 transplanted into DENV4:
1. T49E, S122L, G123E, I132Y
2. A71D, T148Q, D225T, V229P, D307K, K321Q, V362P
(in addition to those listed in #1)
3. S168A, E180A
4. E52N, V53P, L55V, T138S (in addition to those
listed in #3)
5. Any and all combinations of 1, 2, 3, 4 and the
original sequence DENV4/1/2
MRCVGVGNRDFVEGVSGGAWVDLVLEHGGCVTTMAQGKPTLDFELFKTTV
TEVALLRTYCIEASISNITTATRCPTQGEPYLKEEQDQQYICRRDVVDRG
WGNGCGLFGKGGVVTCAKFSCSGKITGNLVQIENLKYTVIVTVHNGDTHA
VGNDTTEHGTTATITPRSPTSEIQLTDYGELTLDCEPRSGIDFNEMILMK
MKKKTWLVHKQWFLDLPLPWTAGADTSEVHWNYKERMVTFKVPHAKRQDV
TVLGSQEGAMHSALAGATEVDSGGTTTMFAGHLKCKVRMEKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 38)

Note: AA #160 could be a T or V, AA #163 could be
a T or M, AA #168 could be a S or A, AA #170 could
be a T or S, AA #171 could be a S or V, AA #173
could be a V or I, AA #174 could be a Q or K, AA
176 could be a P or T, AA #180 could be a E or A The following changes could also be made to
generate 2 viruses with a larger region of DENV1
and/or DENV2 transplanted into DENV4:
1. Y81S, K83S, V242N, R247K
2. I68T, A71E, T72S, R93K, R94H, D95S, V96M, V113I
(in addition to those listed in #1)
3. S168A, E180A
4. E52N, V53P, L55V, T138S (in addition to those
listed in #3)
5. Any and all combinations of 1, 2, 3, 4 and the
original sequence DENV4/2/3
MRCVGVGNRDFVEGVSGGAWVDLVLEHGGCVTTMAQGKPTLDFELTKTTA
TQLATLRKLCIEASISNITTATRCPTQGEPYLKEEQDQQYICRRDVVDRG
WGNGCGLFGKGGVVTCAKFSCSGPIEGKVVQIENLEYTVVVTVHNGDTHA
VGNDTSNHGVTATITPRSPSVEVKLPDYGELTLDCEPRSGIDFNEMILLT
MKKKAWMVHRQWFFDLPLPWTSGADTSEVHWNYKERMVTFKVPHAKRQDV
TVLGSQEGAMHSALAGATEIQNSGGTSIFAGHLKCKVRMEKLRLKGMSYS
MCTGKFKIVKEIAETQHGTIVIRVQYEGDGSPCKIPFEITDLEKRHVLGR
LITVNPIVTEKDSPVNIEAEPPFGDSYIIIGVEPGQLKLNWFKKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 39)

The following changes could also be made to
generate 2 viruses with a larger region of DENV2
and/or DENV3 transplanted into DENV4:
1. Y81S, K83S, V242N, R247K
2. I68T, A71E, T72S, R93K, R94H, D95S, V96M, V113I
(in addition to those listed in #1)
3. T49E, S122L, G123E, I132Y
4. A71D, T148Q, D225T, V229P, D307K, K321Q, V362P
(in addition to those listed in #3)
5. Any and all combinations of 1, 2, 3, 4 and the
original sequence DENV4/1/2/3
MRCVGVGNRDFVEGVSGGAWVDLVLEHGGCVTTMAQGKPTLDFELFKTTV
TQLATLRKLCIEASISNITTATRCPTQGEPYLKEEQDQQYICRRDVVDRG
WGNGCGLFGKGGVVTCAKFSCSGPIEGKVVQIENLKYTVIVTVHNGDTHA
VGNDTTEHGTTATITPRSPSVEVKLTDYGELTLDCEPRSGIDFNEMILLT
MKKKAWMVHRQWFFDLPLPWTSGADTSEVHWNYKERMVTFKVPHAKRQDV
TVLGSQEGAMHSALAGATEIQNSGGTSIFAGHLKCKVRMEKLRLKGMSYS
MCTGKFKIVKEIAETQHGTIVIRVQYEGDGSPCKIPFEITDLEKRHVLGR

SEQUENCES

LITVNPIVTEKDSPVNIEAEPPFGDSYIIIGVEPGQLKLNWFKKGSSIGK
MFESTYRGAKRMAILGETAWDFGSVGGLFTSLGKAVHQVFGSVYTTMFGG
VSWMIRILIGFLVLWIGTNSRNTSMAMTCIAVGGITLFLGFTVQA (SEQ
ID NO: 40)

Note: AA #50 could be a V or A, AA #52 could be a
Q or N, AA #55 could be a T or V, AA #160 could be
a T or V, AA #163 could be a T or M, AA #168 could
be a S or A, AA #170 could be a T or S, AA #171
could be a S or V, AA #173 could be a Von, AA #174
could be a Q or K, AA #176 could be a P or T, AA
180 could be a E or A, AA #272 could be a T or N,
275 could be a T or G, #276 could be a T or N,
277 could be a T or L

SEQUENCES

The following changes could also be made to
generate 2 viruses with a larger region of DENV1,
DENV2, and/or DENV3 transplanted into DENV4:
1. Y81S, K83S, V242N, R247K
2. I68T, A71E, T72S, R93K, R94H, D95S, V96M, V113
(in addition to those listed in #1)
3. T49E, S122L, G123E, I132Y
4. A71D, T148Q, D225T, V229P, D307K, K321Q, V362P
(in addition to those listed in #3)
5. S168A, E180A
6. E52N, V53P, L55V, T138S
7. Any and all combinations of 1, 2, 3, 4, 5, 6
and the original sequence

What is claimed is:

1. A chimeric dengue virus E glycoprotein comprising a dengue virus E glycoprotein backbone that comprises amino acid substitutions that introduce a protein domain from a dengue virus serotype that is different from the dengue virus serotype of dengue virus E glycoprotein backbone, wherein the dengue virus E glycoprotein backbone is from dengue virus serotype 4 and the protein domain is from dengue virus serotype 2, wherein the glycoprotein comprises the amino acid sequence:

```
                                               (SEQ ID NO: 1)
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRIKGMSYT

MCSGKFSIDKEMAETQHGTTVVKVKYEGAGAPCKVPIEIRDVNKEKVVGR

VISSTPLAENTNSVTNIELEPPFGDSYIVIGVGNSALTLHWFRKGSSIGK

MFESTYRGAKRMAILGETAWDFGSVGGLFTSLGKAVHQVFGSVYTTMFGG

VSWMIRILIGFLVLWIGTNSRNTSMAMTCIAVGGITLFLGFTVQA,
``` wherein said amino acid sequence comprises the following amino acid substitutions:

T300S, S303T, S307K, D309V, M312I, T320I, V322I, K323R, K325Q, A329D, A331S, V335I, I337F, R340T, V342L, N343E, E345R, K346H, V348L, V351L, S353T, S354V, T355N, L357I, A358V, E359T, N360E, T361K, N362D, V364P, T365V, L369A, V379I, G383E, N384P, S385G. A386Q, T388K, H390N, and R393K.

2. A chimeric dengue virus E glycoprotein comprising a dengue virus E glycoprotein backbone that comprises amino acid substitutions that introduce a protein domain from a dengue virus serotype that is different from the dengue virus serotype of the dengue virus E glycoprotein backbone, wherein the dengue virus E glycoprotein backbone is from dengue virus serotype 4 and the protein domain is from dengue virus serotype 2, wherein the glycoprotein comprises the amino acid sequence:

(SEQ ID NO: 5)
MRCVGVGNRDFVEGVSGGAWVDLVLEHGGCVTTMAQGKPTLDFELTKTTA

KEVALLRTYCIEASISNITTATRCPTQGEPYLKEEQDQQYICRRDVVDRG

WGNGCGLFGKGGVVTCAKFSCSGKITGNLVQIENLEYTVVVTVHNGDTHA

VGNDTSNHGVTATITPRSPSVEVKLPDYGELTLDCEPRSGIDFNEMILMK

MKKKTWLVHKQWFLDLPLPWTAGADTSEVHWNYKERMVTFKVPHAKRQDV

TVLGSQEGAMHSALAGATEVDSGDGNHMFAGHLKCKVRMEKLRLKGMSYS

MCTGKEKIVIKEIAETQHGTIVIMYEGDGSPCKIPFEITDLEKRHVLGRL

ITVNPIVTEKDSPVNIEAEPPFGDSYIIIGVEPGQLKLNWFKKGSSIGKM

FESTYRGAKRMAILGETAWDFGSVGGLFTSLGKAVHQVFGSVYTTMFGGV

SWMIRILIGFLVLWIGTNSRNTSMAMTCIAVGGITLFLGFTVQA.

3. A flavivirus particle or virus like particle (VLP) comprising the E glycoprotein of claim 1.

4. A population of flavivirus particles comprising the flavivirus particle of claim 3.

5. A composition comprising the E glycoprotein of claim 1 in a pharmaceutically acceptable carrier.

6. A composition comprising the population of claim 4 in a pharmaceutically acceptable carrier.

7. A composition comprising the flavivirus particle and/or VLP of claim 3 in a pharmaceutically acceptable carrier.

8. A method of producing an immune response to a dengue virus in a subject, comprising administering to the subject an effective amount of the E glycoprotein of claim 1.

9. A flavivirus particle or virus like particle (VLP) comprising the E glycoprotein of claim 2.

10. A population of flavivirus particles comprising the flavivirus particle of claim 9.

11. A composition comprising the E glycoprotein of claim 2 in a pharmaceutically acceptable carrier.

12. A composition comprising the population of claim 10 in a pharmaceutically acceptable carrier.

13. A composition comprising the flavivirus particle and/or VLP of claim 9 in a pharmaceutically acceptable carrier.

14. A method of producing an immune response to a dengue virus in a subject, comprising administering to the subject an effective amount of the E glycoprotein of claim 2.

* * * * *